US006942866B2

(12) United States Patent  (10) Patent No.: US 6,942,866 B2
Birkett  (45) Date of Patent: Sep. 13, 2005

(54) MALARIA IMMUNOGEN AND VACCINE

(75) Inventor: Ashley J. Birkett, Escondido, CA (US)

(73) Assignee: Apovia, Inc., San Diego, CA (US)

( * ) Notice: Subject to any disclaimer, the term of this patent is extended or adjusted under 35 U.S.C. 154(b) by 0 days.

(21) Appl. No.: 09/931,325

(22) Filed: Aug. 15, 2001

(65) Prior Publication Data

US 2003/0054337 A1 Mar. 20, 2003

Related U.S. Application Data

(60) Provisional application No. 60/225,813, filed on Aug. 16, 2000.

(51) Int. Cl.$^7$ .................. A61K 39/00; A61K 39/29; A61K 39/295; A61K 39/015; C07K 14/02

(52) U.S. Cl. .................. 424/268.1; 424/184.1; 424/204.1; 424/227.1; 424/272.1; 530/350; 530/403

(58) Field of Search .................. 424/184.1, 185.1, 424/189.1, 193.1, 199.1, 204.1, 227.1, 264.1, 272.1; 435/5, 6, 69.1, 320.1; 514/2, 12, 16, 17, 18, 14, 49; 530/300, 324, 326, 327, 350, 402, 403; 536/23.1, 23.5, 23.7, 23.72

(56) References Cited

U.S. PATENT DOCUMENTS

| 4,818,527 A | 4/1989 | Thornton et al. ............. 424/88 |
| 4,882,145 A | 11/1989 | Thornton et al. ............. 424/88 |
| 4,886,782 A | 12/1989 | Good et al. .................... 514/12 |
| 5,143,726 A | 9/1992 | Thornton et al. ............. 424/88 |
| 5,614,194 A | 3/1997 | Colman et al. .......... 424/191.1 |
| 5,928,902 A | 7/1999 | De Wilde et al. .......... 435/69.3 |
| 6,231,864 B1 * | 5/2001 | Birkett .................... 424/189.1 |

FOREIGN PATENT DOCUMENTS

| DE | 3741183 A1 * | 9/1988 |
| WO | WO 98/31382 * | 7/1998 |
| WO | WO 99/40934 | 8/1999 |
| WO | WO 00/32625 | 6/2000 |
| WO | WO 01/27281 | 4/2001 |
| WO | WO 01/98333 | 12/2001 |
| WO | WO 02/13765 | 2/2002 |
| WO | WO 02/14478 | 2/2002 |

OTHER PUBLICATIONS

Kratz et al., "Native display of complete foreign protein domains on the surface of hepatitis B virus capsids," Proc. Natl. Acad. Sci. USA, vol. 96, pp. 1915–1920 (1999).*
Nardin et al., "Conserved Repetitive Epitope Recognized by CD4= Clones from a Malaria–Immunized Volunteer," Science, vol. 246, pp. 1603–1606 (1989).*
Metzger et al., "Proline–138 is essential for the assembly of hepatitis B virus core protein," Journal of General Virology, vol. 79, pp. 587–590 (1998).*

Schodel et al., "Immunity to MAlaria Elicited by Hybrid Hepatits B Virus COre PArticles Carrying Circumsporozoite Protien Epitopes," Journal of Experimental Medecine, vol. 180, pp. 1037–1046 (1994).*
Pumpens et al., "Hepatitis B Core Particles as Epitope Carriers, " Intervirology, vol. 38, pp. 63–74 (1995).*
Marlar, T., et al., Trans R. Soc. Trop. Med. Hyg., (1995) 89(3): p. 307–308.
Garg et al., Trans. R. Soc Trop. Med. Hyg., (1995) 89(6): p. 656–657.
Baird et al., Am. J. Trop. Med. Hyg.,(1991) 44(5): p. 547–552.
Baird et al., Trans R Soc Trop Med Hyg, (1996) 90(4): p. 409–411.
Baird et al., J. Infect. Dis., (1995) 171(6): p. 1678–1682.
Murphy et al., Lancet, (1993) 341(8837): p. 96–100.
Schwartz et al., [letter]. N. Engl. J. Med., (1991) 324(13): p. 927.
Rieckmann et al., Lancet, (1989) 2(8673): p. 1183–1184.
Charoenlarp et al., Southeast Asian J. Trop. Med. Public Health, (1973) 4(1): p. 135–137.
Krotoski, [letter]. N. Engl. J. Med., (1980) 303(10): p. 587.
Schuurkamp et al., Trans. R. Soc. Trop. Med. Hyg., (1992) 86(2): p. 121–122.
Good, et al., Anu. Rev. Immunol., (1998) 16: p. 57–87.
Clyde et al., Am. J. Med. Sci., (1973) 266(6): p. 398–403.
Rieckmann et al., Trans. R. Soc. Trop. Med. Hyg., (1974) 68(3): p. 258–259.
Zavala et al., Science, (1985) 228(4706): p. 1436–40.
Nussenzweig et al., Ciba Found. Symp., (1986) 119: p. 150–163.
Etlinger et al., Immunology, (1988) 64(3): p. 551–558.
Etlinger et al., J. Immunol., (1988) 140(2): p. 626–633.
Herrington et al., Nature, (1987) 328(6127): p. 257–259.
Ballou et al., Lancet, (1987) 1(8545): p. 1277–1281.
Good et al., Science, (1987) 235(4792): p. 1059–62.
Calvo–Calle et al., J. Immunol., (1993) 150(4): p. 1403–1412.
Moreno et al., Int. Immunol., (1991) 3(10): p. 997–1003.
Stoute et al., N. Engl. J. Med., (1997) 336(2): p. 86–91.
Stoute et al., J.Infect Dis. (Oct. 1998) 178(4): 1139–44.
Milich et al., Science, (1986) 234(4782): p. 1398–1401.
Herrington et al., Am J Trop Med Hyg. (1991) 45(6): p. 695–701.

(Continued)

Primary Examiner—James Housel
Assistant Examiner—Zachariah Lucas
(74) Attorney, Agent, or Firm—Welsh & Katz, Ltd.

(57) ABSTRACT

A chimeric, carboxy-terminal truncated hepatitis B virus nucleocapsid protein (HBc) is disclosed that contains an immunogen for inducing the production of antibodies to malarial proteins. An immunogenic malarial epitope is expressed between residues 78 and 79 of the HBc immunogenic loop sequence. The chimer preferably contains a malaria-specific T cell epitope and is preferably engineered for both enhanced stability of self-assembled particles and enhanced yield of those chimeric particles. Methods of making and using the chimers are also disclosed.

50 Claims, 8 Drawing Sheets

OTHER PUBLICATIONS

Schodel et al., *Behring Inst. Mitt.* (1997) (98): p. 114–119.
Hoffman et al., *Nat. Med.* (1997) 3(1):80–83.
Conway et al., *Nature,* (1997) 386:91–94.
Bottcher et al., *Nature,* (1997) 386:88–91.
Zheng et al., *J. Biol. Chem.,* (1992) 267(13):9422–9429.
Birnbaum et al., *J.Virol.* (1990) 64, 3319–3330.
Clarke et al., F. Brown et al. eds. *Vaccines* (1991) 91, Cold Spring Harbor Laboratory, Cold Spring Harbor, New York, pp. 313–318.
Seifer et al., *Intervirology* (1995) 38:47–62.
Gallina et al., *J. Virol.* (1989) 63:4645–4652.
Inada et al., *Virus Res.,* (1989) 14:27–48.
Maassen et al., *Arch. Virol.* (1994) 135:131–142.
Schodel et al., *Infect. Immunol.* (1994) 62:1669–1676.
Ulrich et al., *Adv. Virus Res.* vol. 50 (1998) Academic Press pp. 141–182.
Qari et al., *Lancet* (1993) 341(8848):780–783.
Moreno et al., *J. Immunol.* (1993) 151(1): 489–499.
Hoffman et al., *Malaria Vaccine Development,* Chapter 3: Attacking the Infected Hepatocyte, 1996 American Society for Microbiology, Washington, D.C.
Calvo–Calle et al., *J. Immunol.* (1997) 159(3): p. 1362–1373.
Coatney et al. (1962) 9:290–293.
Krüger et al., *Biol. Chem.* (1999) 380:275–276.
Nardin et al., *J. Exp. Med.* (1982) 156:20–30.
Poster presented by J. Haron at the Center for Advanced Technology and Medicine (CABM) Symposium, Rutgers University Medical Center on Oct. 13–14, 1999.
Isaguliants et al., *Immunol. Ltr.* (1994) 42:173–178.
Schodel et al., *J. Biotechnol.* (1996) 44:91–96.
Wynne et al., *Mol. Cell* (Jun. 1999) 3:771–780.
Carl R. Noller., *Chemistry of Organic Compounds.* 35–, 1952.
Lyons et al.., *J. Infection and Immunity,* 70(12):6860–6870(Dec. 2002).
Sällberg et al., *Invervirology,* 45:350–361 (2002).
Palenzuela et al., *Biotecnologia Aplicada,* vol. 18(3):137–142 (2002.
Milich et al., *Vaccine,* 20:771–788 (2002).
Lazdina et al., *Journal of General Virology,* 84:139–146 (2003).

\* cited by examiner

FIG. 1 pKK223-3    TTCACACAGGAAACAGAATTCCCGGGATCCGTCGACCTGCAGCCAAGCTT
            <u>HindIII</u>

SEQ ID NO:180 pKK223-3N   TTCACATAAGGAGGAAAAAA<u>Accatgg</u>GATCCG--------AAGCTT
                                  NcoI

SEQ ID NO:181

FIG. 2A

Cloning Step 1

```
  I   N   A   N   P   N   A   N   P   N   A   N   P   N   A   N   P   E   L
A ATT AAC GCT AAT CCG AAT GCT AAT CCG AAC GCT AAT CCG AAT GCT AAT CCG GAG CT
  TTG CGA TTA GGC TTA GGC TTG CGA TTA GGC TTA GGC TTG CGA TTA GGC TTA GGC C
```

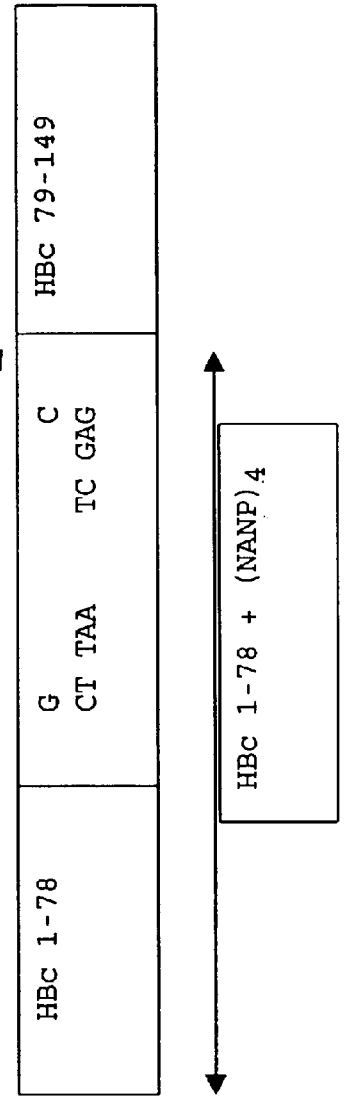

HBc 79-149

G       C
CT TAA  TC GAG

HBc 1-78

HBc 1-78 + (NANP)₄

Cloning Step 2 -

```
  I   E   Y   L   N   K   I   Q   N   S   L   S   T   E   W   S   P   C   S   V   T   *
A ATT GAA TAT CTG AAC AAA ATC CAG AAC TCT CTG TCC ACC GAA TGG TCT CCG TGC TCC GTT ACC TAA AAG CT
  CTT ATA GAC TTG TTT TAG GTC TTG AGA GAC AGG TGG CTT ACC AGA GGC ACG AGG CAA TGG ATT T
```

HBc79–149 + PF/CS326-345

Cloning Step 3

FIG. 6A

```
Ground Squirrel    mylfhlclvf acvpcptvga sklclgwlwd

1
HBc AYW            mdidpykefg atvellsflp sdffpsvrdl ldtasalyre
HBc ADW            mdidpykefg atvellsflp sdffpsvrdl ldtasalyre
HBc ADW2           mdidpykefg atvellsflp sdffpsvrdl ldtasalyre
HBc ADYW           mdidpykefg atvellsflp sdffpsvrdl ldtaaalyrd
Woodchuck          mdidpykefg ssyqlnflp  ldffpdlnal vdtatalyee
Ground Squirrel    mdidpykefg ssyqlnflp  ldffpdlnal vdtaaalyee 41
HBc AYW            alespehcsp hhtalrqail cwgelmtlat wvgvnledpa
HBc ADW            alespehcsp hhtalrqail cwgelmtlat wvgnnlqdpa
HBc ADW2           alespehcsp hhtalrqail cwgelmtlat wvgnnledpa
HBc ADYW           alespehcsp hhtalrqail cwgdlmtlat wvgtnledpa
Woodchuck          eltgrehcsp hhtairqalv cwdeltklia wmssnitseq
Ground Squirrel    eltgrehcsp hhtairqalv cweeltrlit wmsentteev
```

FIG. 6B

```
            81
HBc AYW          srdlvvsyvn  tnmglkfrql  lwfhiscltf  gretvieylv
HBc ADW          srdlvvnyvn  tnmglkirql  lwfhiscltf  gretvleylv
HBc ADW2         srdlvvnyvn  tnvglkirql  lwfhiscltf  gretvleylv
HBc ADYW         srdlvvsyvn  tnvglkfrql  lwfhiscltf  gretvleylv
Woodchuck        vrtiivnhvn  dtwglkvrqs  lwfhlscltf  gqhtvqeflv
Ground Squirrel  rriivdhvnn  twglkvrqtl  wfhlscltfg  qhtvqeflvs 121
HBc AYW          sfgvwirtpp  ayrppnapil  stlpettvvr  rrgrsprrrt
HBc ADW          sfgvwirtpp  ayrppnapil  stlpettvvr  rrdrgrsprr
HBc ADW2         sfgvwirtpp  ayrppnapil  stlpettvvr  rrdrgrsprr
HBc ADYW         sfgvwirtpp  ayrppnapil  stlpettvvr  rrgrsprrrt
Woodchuck        sfgvwirtpa  pyrppnapil  stlpehtvir  rrggarasrs
Ground Squirrel  fgvwirtpap  yrppnapils  tlpehtvirr  rggsraarsp 161
HBc AYW          psprrrsqs   prrrrsqsre  sqc
HBc ADW          rtpsprrrs   qsprrirsqs  resqc
HBc ADW2         rtpsprrrps  qsprrrsqs   resqc
HBc ADYW         psprrrsqs   prrrrsqsre  sqc
Woodchuck        prrrtpsprr  rrsqsprrrr  sqc
Ground Squirrel  rrrtpsprrr  rsqsprrrrs  qspasnc
```

MALARIA IMMUNOGEN AND VACCINE

CROSS-REFERENCE TO RELATED APPLICATION

This is a continuation-in-part of application Ser. No. 60/225,813, filed Aug. 16, 2000, whose disclosures are incorporated herein by reference.

TECHNICAL FIELD

The present invention relates to the intersection of the fields of immunology and protein engineering, and particularly to an immunogen and vaccine useful in prevention of malaria infection by P. falciparum or P. vivax.

BACKGROUND OF THE INVENTION

Malaria is by far the world's most important tropical parasitic disease, killing more people than any other communicable disease, with the exception of tuberculosis. The causative agents in humans are four species of Plasmodium protozoa: P. falciparum, P. vivax, P. ovale and P. malariae. Although P. falciparum accounts for the majority of infections and is responsible for the vast majority of deaths attributable to malaria, P. vivax causes a recurring chronic debilitating disease for which a vaccine is necessary.

Malaria infection begins when a female Anopheles mosquito infected with one of the four Plasmodium species infectious for humans bites a person. The mosquito's saliva carries the malarial sporozoites into the blood. Approximately 30 minutes later these sporozoites enter the liver. Once in the liver, the sporozoites divide over the course of about 5 days, forming a schizont. A schizont may contain up to 30,000 merozoites, which spill into the bloodstream when the schizont ruptures. Within seconds, merozoites infect red blood cells (RBCs) and again replicate asexually, with each schizont producing up to 36 merozoites.

Each time a RBC bursts and liberates progeny, other blood cells are infected. The cycle can continue until the person dies of anemia and/or other complications. A few of the merozoites in RBCs differentiate into gametocytes, a sexual form, which, if ingested by a mosquito, are liberated from the RBCs in the mosquito stomach and subsequently mate. The progeny, sporozoites, accumulate in the saliva and the process starts again when the mosquito feeds [See, Hoffman et al., (1996) "Attacking the Infected Hepatocyte", in *Malaria Vaccine Development* (ed. S. L. Hoffman), p. 35. ASM Press, Washington, D.C., for review).

P. vivax malaria is most prevalent in Latin America (where it is as or more prevalent than P. falciparum) and Asia. Although rarely fatal, P. vivax malaria has a dormant liver phase that is associated with relapses that show variability in duration, depending on the strain.

Presently, there is not an effective vaccine against any form of malaria. For many years, chloroquine was a cheap and effective therapeutic for treating malaria. But in recent years, chloroquine resistance has increased dramatically for P. falciparum. In the past 10 years, P. vivax has also developed chloroquine resistance with cases being reported in south-east Asia, the south-west Pacific; Burma [Marlar, T., et al., Trans. R. Soc. Trop. Med. Hyg., 1995. 89(3): p. 307–308] perhaps India [Garg et al., Trans. R. Soc Trop. Med. Hyg., 1995. 89(6): p. 656–657],Indonesia [Baird et al., Am. J. Trop. Med. Hyg., 1991, 44(5): p. 547–552; Baird et al., Trans R Soc Trop Med Hyg, 1996, 90(4): p. 409–411; Baird et al., J. Infect. Dis., (1995) 171(6): p. 1678–1682; Murphy et al., Lancet, (1993) 341(8837): p. 96–100; and Schwartz et al., [letter]. N. Engl. J. Med., (1991) 324(13): p. 927] and Papua New Guinea [Rieckmann et al., Lancet, (1989) 2(8673): p. 1183–1184].

Primaquine is the only antimalarial drug that is effective against hyponozoites, which are associated with the dormant phase in the liver responsible for relapses. Different P. vivax strains show differential patterns of relapse; for example, a Korean P. vivax strain has been shown to be 100 percent radically cured by a given primaquine regime (WHO, 1967), whereas the same regime is only 70 percent effective with the Chesson strain [Coatney et al., J. Natl. Malaria Soc., 1962. 9: p. 285–292]. To complicate treatment with primaquine further, reports in the 1970s highlighted primaquine-resistant P. vivax in south-east Asia [Charoenlarp et al., Southeast Asian J. Trop. Med. Public Health, (1973) 4(1): p. 135–137 and Krotoski, [letter]. N. Engl. J. Med., (1980) 303(10): p. 587]; observations have steadily increased in other locations in recent years [Schuurkamp et al., Trans. R. Soc. Trop. Med. Hyg., (1992) 86(2): p. 121–122] suggesting that widespread resistance to primaquine is emerging.

Clearly, the most effective approach to combating malaria is an effective vaccine. As with smallpox, and potentially polio in the near future, a coordinated worldwide vaccination program can result in eradication of communicable human diseases. This may also be achievable for malaria if an effective vaccine can be developed.

There are three recognized anti-parasitic approaches to malaria vaccine development. These are proposed to function by interrupting the parasite's lifecycle at three different stages.

The first and most attractive approach is the pre-erythrocytic vaccine, which aims to block sporozoite entry into the hepatocyte and/or release of merozoites into the blood stream. Immediately following infection, sporozoites migrate to the liver and begin the exoerythrocytic stage of their lifecycle. Successful blocking of hepatocyte entry, or the destruction of infected hepatocytes prior to liberation of merozoites, would prevent the disease, the passage of the parasite on to feeding mosquitoes, and merozoite release and subsequent invasion of red blood cells.

A second approach is to develop an 'antidisease' vaccine. The target is the red blood cell stage of the infection, during which the parasite grows at an exponential rate. Also known as 'asexual blood stage' vaccines, the merozoite surface protein 1 (MSP-1) and apical membrane antigen 1 (AMA-1) protein have emerged as the two most promising vaccine candidates for intervening at this stage of the disease (See, Good, et al., Anu. Rev. Immunol., (1998) 16: p. 57–87,, for review). This stage is thought to represent a conceptually more difficult target compared with the pre-erythrocytic stage, which is associated with 10–20 sporozoites per mosquito bite, due to the tremendous increase in parasite load once the blood stage is reached.

A third approach, known as the 'transmission-blocking' vaccine, would not stop infection or symptoms in the individual. However, it would prevent infection from spreading to others by blocking the lifecycle in the mosquito by inducing antibodies that the mosquito would ingest from the host with its blood meal. This vaccine approach is more attractive as a long-term global solution to eradication of malaria and less attractive to the immediate needs of travelers and the military forces.

In the 1960s, researchers at New York University (NYU) achieved full protection from malaria infection by injecting animals with small numbers of sporozoites from mosquitoes that had previously been irradiated. Later, researchers at the University of Maryland, NYU and Walter Reed Army Institute showed that percent of a group of human volunteers immunized with irradiated sporozoites later resisted exposure to virulent sporozoites [Clyde et al., Am. J. Med. Sci., (1973) 266(6): p. 398–403 and Rieckmann et al., Trans. R. Soc. Trop. Med. Hyg., (1974) 68(3): p. 258–259]. This work confirmed that protective immunity to the sporozoite stage (i.e. the pre-erythrocytic stage) of the malaria parasite could be induced. However, an inability to culture sporozoites in vitro thwarted the possibility of using them as a vaccine.

The strategic development of a synthetic malaria vaccine required the identification of immunodominant, neutralizing malaria epitopes. In 1985, a group at NYU led by Drs. Ruth and Victor Nussenzweig, identified the dominant B cell epitope from the circumsporozoite protein (CS), a major component of the sporozoite surface membrane at the time the parasite enters the bloodstream [Zavala et al., Science, (1985) 228(4706): p. 1436–40]. Antibodies to the repeated epitope were shown to be sporozoite neutralizing by protecting against rodent and human malaria [Nussenzweig et al., Ciba Found. Symp., (1986) 119: p. 150–163]. Antibodies to the CS protein also correlated positively with protection in immunized mice and in naturally infected individuals.

These studies strongly suggest that anti-CS repeat antibodies alone are able to confer protection against malaria infection, provided sufficient antibody titers can be raised. The identification of this epitope therefore enabled, for the first time, the strategic development of synthetic CS-based malaria vaccines. Several malaria vaccine candidates employing different carriers were developed based upon the identification of this epitope. The main focus of malaria vaccine development has been on P. falciparum, and it is widely assumed that information gained from studying P. falciparum extend to other Plasmodium species, including P. vivax. A brief overview of four pre-erythrocytic P. falciparum malaria vaccine candidates is given below.

The (NANP)$_3$ synthetic peptide conjugated to the protein carrier tetanus toxoid (TT) was the first synthetic malaria vaccine to undergo phase I and phase II clinical trials in the late 1980s [Etlinger et al., Immunology, (1988) 64(3): p. 551–558; Etlinger et al., J. Immunol., (1988) 140(2): p. 626–633 and Herrington et al., Nature, (1987) 328(6127): p. 257–259]. TT is widely known to provide powerful T cell help for coupled immunogens. Of the thirty-five vaccinees, the three having the highest titers of anti-sporozoite antibodies were selected for challenge studies. One of the vaccine recipients remained free of parasitaemia at 29 days, whereas the other two did not exhibit asexual stage parasites until 11 days, compared with a mean of 8.5 days for the un-vaccinated control group. Therefore, protection again correlated positively with anti-NANP titers.

The limited effectiveness of this vaccine was attributed to suboptimal levels of anti-NANP antibodies. Attempts to increase dosage were hindered by toxicity of the TT carrier. Further, the lack of parasite-derived determinants capable of priming malaria-specific T cells also likely contributed to the low levels of protection.

Short synthetic peptides often have an in vivo half-life that is too short for them to be effective as prophylactic or therapeutic drugs. Standard approaches for increasing the immunogenicity of peptides is to either couple them to larger carrier proteins, or to assemble them into multimeric structures. In this case, 32 copies of the CS repeat sequence ((NANP)$_{15}$(NVDP))$_2$ were linked and recombinantly fused to a random 32 amino acid fusion protein 20. [Ballou et al., Lancet, (1987) 1(8545): p. 1277–1281.] This vaccine candidate was called FSV-1.

Following immunization, twelve of the fifteen volunteers developed antibodies that reacted with sporozoites. No patients exhibited adverse reactions to the protein, indicating that the NANP (SEQ ID NO: 184) repeat itself is non-toxic. Of the fifteen patients immunized with 3 doses, six were selected to receive a fourth dose and were then challenged with the malaria parasite. Parasitaemia did not develop in the volunteer with the highest titer of CS antibodies, and parasitaemia was delayed in two of the other five vaccinees.

As with the NANP-TT vaccine discussed above, protection correlated positively with anti-NANP titers. This vaccine was deemed partially successful in that it reconfirmed that humans can be protected by CS protein subunit vaccines. However, the level of protection was not sufficient to warrant larger trials of this particular candidate.

A major shortfall of this vaccine was that it did not provide an efficient source of T cell help. The only individuals who would have received T cell help from this vaccine would be those in whom the CS repeat served as both a B and T helper (Th) cell epitope. However, this sequence is known to be a Th epitope for only a limited number of individuals; i.e. it is highly genetically restricted.

Nardin and coworkers at NYU have been able elicit relatively high titers of anti-CS antibody in a diverse range of genetic backgrounds by combining the NANP repeat epitope with the T cell site identified by Berzofsky and Good [Good et al., Science, (1987) 235(4792): p. 1059–62] in a MAP format [Calvo-Calle et al., J. Immunol., (1993) 150(4): p. 1403–1412]. Using their proprietary 'universal' form of the CS T cell epitope, Nardin and co-workers have been able to elicit anti-CS antibodies in all genetic backgrounds tested, suggesting that genetic restriction is alleviated by inclusion of this epitope.

Although MAPs have proven to be excellent research tools, providing valuable insight into immune recognition of the CS protein, there are several intrinsic problems associated with using them in a commercial vaccine. Their commercial utility has yet to be established relative to manufacturing and cost issues. Nevertheless, ongoing human clinical testing of these vaccine candidates will provide very useful information pertaining to the actual anti-NANP titers necessary for protective immunity.

One of the most promising malaria vaccines of recent times utilizes the hepatitis B surface antigen (HBsAg) to deliver CS epitopes, an approach developed by SmithKline Beecham (SKB) that is disclosed in U.S. Pat. No. 5,928,902 that issued on Jul. 27, 1999. That patent inter alia discloses a hybrid protein comprised of all of the C-terminal portion of the CS protein, four or more tandem repeats of the CS immunodominant region and the hepatitis B surface antigen. The CS epitopes include the NANP repeat, in concert with additional CS epitopes, including the T cell site identified by Berzofsky and Good [Good et al., Science, (1987) 235 (4792): p. 1059–62] (but not the universal form developed by Nardin and co-worker [Moreno et al., Int. Immunol., (1991) 3(10): p. 997–1003 and Calvo-Calle et al., J. Immunol., (1997) 159(3): p. 1362–1373]), fused to the hepatitis B surface protein.

This vaccine was recently the subject of human clinical trials [Stoute et al., N. Engl. J. Med., [1997] 336(2): p. 86–91]. When administered with one of three different adjuvants, this vaccine protected 1/7, 2/7 and 6/7 individuals, respectively. Of the seven individuals immunized with vaccine 2 (adjuvant: oil-in-water emulsion), none of the five patients with anti-CS titers (IFA) in the range of 100–12,800 were protected, whereas the two vaccine recipients with antibody titers in the range of 25,600–51,200 were both protected. Again, protection was correlated positively with anti-CS titers. It is interesting to note that the one patient that received vaccine 1, the alum/oil-in-water formulation, remained protected for at least six months.

The preliminary efficacy report for SKB's malaria vaccine candidate (RTS,S) [Stoute et al. (1997) N. Engl. J. Med., 336(2): p. 86–91] although encouraging, was tempered by the lack of long-term protection in follow-up studies [Stoute et al. (October 1998) J. infect Dis., 178(4):1139–44]. It was also apparent that the use of a potent and complex adjuvant (SBAS2) containing the immunostimulants QS-21 and monophosphoryl lipid A (MPL), formulated in an oil-in-water emulsion, was essential to achieve efficacy, because volunteers receiving the vaccine formulated on alum were not protected. Five of six patients, who were initially protected after administration of the RTS,S/SBAS2 formulation, were not protected six months after receiving the third vaccine dose. Similar results were recently reported at the 48$^{th}$ annual meeting of the American Society of Tropical Medicine and Hygiene for a field trial conducted in Africa.

Like HBsAg, the hepatitis B core antigen (HBcAg), is a particulate protein derived from the hepatitis B virus that has been proposed as a carrier for heterologous epitopes. The relative immunogenicity of HBsAg (HBs) has been compared with HBcAg (HBc), and the ability of each to evoke immune responses in different genetic backgrounds [Milich et al., Science, (1986) 234 (4782) p. 1398–1401]. These data emphasize the higher immunogenicity of HBc relative to HBs, and the universal responsiveness to HBc, irrespective of genetic background.

For example, HBc is more than 300 times more immunogenic than HBs in BALB/c mice; and, although both B10.S and B10.M mice are non-responders to HBs, every strain tested is responsive to HBc. These results re-emphasize the suitability of HBc as a vaccine carrier and specifically, its superiority over HBs, hence the selection of HBc as opposed to HBs to carry heterologous epitopes. These facets of HBc are thought to be particularly important in malaria vaccine development, because they address the genetic restriction and inadequate antibody titers that have been largely responsible for the inability to develop an effective vaccine using the neutralizing CS epitopes.

The positive correlation between protection against malaria infection and anti-CS antibody titer has been demonstrated repeatedly over the past 15 years [Etlinger et al., Immunology, (1988) 64(3): p. 551–558; Etlinger et al., J. Immunol., (1988) 140(2): p. 626–633; Ballou et al., Lancet, (1987) 1(8545): p. 1277–1281; Stoute et al., N. Engl. J. Med., (1997) 336(2): p. 86–91 and Herrington et al.,. Am J Trop Med Hyg, (1991) 45(6): p. 695–701]. The evidence that a vaccine eliciting high-titer, long-lived antibody responses in sufficient vaccine recipients can be protective suggests that protection against malaria infection is achievable via anti-sporozoite antibody production.

Using rodent models of malaria, it has been found that malaria CS-repeats fused to the immunodominant loop of HBc were able to protect mice against both P. berghei and, perhaps more impressively, P. yoelii to levels of 90–100 percent [Schodel et al., Behring Inst. Mitt., 1997(98): p. 114–119 and Schodel et al., J. Exp. Med., (1994) 180(3): p. 1037–46]. Further, antibody responses to the P. berghei particle were shown to prime antibody responses effectively over a wide range of genetic backgrounds, confirming the universal priming effects of HBc [Schodel et al., J. Exp. Med., (1994) 180(3): p. 1037–46].

Another advantage of the HBc carrier is the fact that it does not require complex adjuvants for efficacy. This is due to the high inherent immunogenicity of the particle. A comparison of the immunogenicity of HBc-P. berghei particles showed that alum, which is approved for human use, was more effective than either IFA or CFA [Schodel et al., J. Exp. Med., (1994) 180(3): p. 1037–46]. The importance of this observation is highlighted by toxicity problems associated with newer, more complex adjuvants as was recently noted in clinical trials of SKB's candidate malaria vaccine [Stoute et al., N. Engl. J. Med., [1997] 336(2): p. 86–91].

The immunodominant B cell epitope of the CS protein of P. falciparum, which has been more widely studied than P. vivax, is a highly conserved repeated tetrapeptide (NANP) [Zavala et al., Science, (1985) 228(4706): p. 1436–40], and antibodies to this epitope have been shown to be sporozoite-neutralizing in protecting against rodent and human malaria. Immune responsiveness to this epitope has been positively correlated with immunity to malaria in both vaccine recipients and naturally infected individuals. Indeed, a review of clinical trials data for pre-erythrocytic vaccines described previously (HBs-CS, FSV-1, NANP-TT), highlights a strong correlation between antibody titer and protection. Those individuals who have been protected by previous vaccine candidates have been associated with the highest anti-NANP antibody titers, with the possible exception of SKB's candidate vaccine (#3-RTS,S and adjuvant SBAS2 containing MPL and QS-21 in a water-in-oil formulation) where adjuvants appeared to play a critical role in protection, because protection was not long-lived, as noted before.

The family hepadnaviridae are enveloped DNA-containing animal viruses that can cause hepatitis B in humans (HBV). The hepadnavirus family includes hepatitis B viruses of other mammals, e.g., woodchuck (WHV), and ground squirrel (GSHV), and avian viruses found in ducks (DHV) and herons (HeHV). Hepatitis B virus (HBV) used herein refers to a member of the family hepadnaviridae, unless the discussion is referring to a specific example.

The nucleocapsid or core of the mammalian hepatitis B virus (HBV or hepadnavirus) contains a sequence of 183 or 185 amino acid residues, depending on viral subtype, whereas the duck virus capsid contains 262 amino acid residues. Hepatitis B core protein monomers self-assemble into stable aggregates known as hepatitis B core protein particles (HBc particles). Two three-dimensional structures are reported for HBc particles. A first that comprises a minor population contains 90 copies of the HBc subunit protein as dimers or 180 individual monomeric proteins, and a second, major population that contains 120 copies of the HBc subunit protein as dimers or 240 individual monomeric proteins. These particles are referred to as T=4 or T=3 particles, respectively, wherein "T" is the triangulation number. These human HBc particles are about are about 30 or 34 nm in diameter, respectively. Pumpens et al., (1995) Intervirology, 38:63–74; and Metzger et al., (1998) J. Gen. Viol., 79:587–590. See also, Wynne et al., (June 1999) Mol. Cell, 3:771–780.

Conway et al., (1997) Nature, 386:91–94, describe the structure of human HBc particles at 9 Ångstrom resolution, as determined from cryo-electron micrographs. Bottcher et al. (1997), Nature, 386:88–91, describe the polypeptide folding for the human HBc monomers, and provide an approximate numbering scheme for the amino acid residues at which alpha helical regions and their linking loop regions form. Zheng et al. (1992), *J. Biol. Chem.*, 267(13):9422–9429 report that core particle formation is not dependent upon the arginine-rich C-terminal domain, the binding of nucleic acids or the formation of disulfide bonds based on their study of mutant proteins lacking one or more cysteines and others' work with C-terminal-truncated proteins [Birnbaum et al., (1990) *J. Virol.* 64, 3319–3330].

The nucleocapsid or viral core protein (HBc) has been disclosed as an immunogenic carrier moiety that stimulates the T cell response of an immunized host animal. See, for example, U.S. Pat. Nos. 4,818,527, 4,882,145 and 5,143,726. A particularly useful application of this carrier is its ability to present foreign or heterologous B cell epitopes at the site of the immunodominant loop that is present at about residue positions 70–90, and more usually recited as about positions 75 through 85 from the amino-terminus (N-terminus) of the protein. Clarke et al. (1991) F. Brown et al. eds., *Vaccines 91*, Cold Spring Harbor Laboratory, Cold Spring Harbor, N.Y., pp. 313–318.

During viral replication, HBV nucleocapsids associate with the viral RNA pre-genome, the viral reverse transcriptase (Pol), and the terminal protein (derived from Pol) to form replication competent cores. The association between the nucleocapsid and the viral RNA pre-genome is mediated via an arginine-rich domain at the carboxyl-terminus (C-terminus). When expressed in heterologous expression systems, such as *E. coli* where viral RNA pre-genome is absent, the protamine-like C-terminus; i.e., residues at positions 150 through 183, binds *E. coli* RNA.

In an application as a vaccine carrier moiety, it is preferable that the HBV nucleocapsids not bind nucleic acid derived from the host. Birnbaum et al., (1990) *J. Virol.* 64, 3319–3330 showed that the protamine-like C-terminal domain of HBV nucleocapsids could be deleted without interfering with the protein's ability to assemble into virus-like particles. It is thus reported that proteins truncated to about position 144; i.e., containing the HBc sequence from position one through about 144, can self-assemble, whereas deletions beyond residue 139 abrogate capsid assembly [Seifer et al., (1995) Intervirology, 38:47–62].

More recently, Metzger et al., (1998) *J. Gen. Viol.*, 79:587–590 reported that the proline at position 138 (Pro-138 or P138) of the human sequence is required for particle formation. Those authors also reported that assembly capability of particles truncated at the carboxy-terminus to lengths of 142 and 140 residues was affected, with assembly capability being completely lost with truncations resulting in lengths of 139 and 137 residues.

Several groups have shown that truncated particles exhibit reduced stability relative to standard hepatitis B core particles [Gallina et al. (1989) *J. Virol.*, 63:4645–4652; Inada, et al. (1989) *Virus Res.*, 14:27–48], evident by variability in particle sizes and the presence of particle fragments in purified preparations [Maassen et al., (1994) *Arch. Virol.*, 135:131–142]. Thus, prior to the report of Metzger et al., above, Pumpens et al., (1995) *Intervirology*, 38:63–74 summarized the literature reports by stating that the carboxy-terminal border for HBc sequences required for self-assembly was located between amino acid residues 139 and 144, and that the first two or three amino-terminal residues could be replaced by other sequences, but elimination of four or eleven amino-terminal residues resulted in the complete disappearance of chimeric protein in transformed *E. coli* cells.

Recombinantly-produced hybrid particles bearing internal insertions (referred to in the art as HBc chimeric particles or HBc chimers) often appear to have a less ordered structure, when analyzed by electron microscopy, compared to particles that lack heterologous epitopes [Schodel et al., (1994) *J. Exp. Med.*, 180:1037–1046]. In some cases the insertion of heterologous epitopes into C-terminally truncated HBc particles has such a dramatic destabilizing affect that hybrid particles cannot be recovered following heterologous expression [Schodel et al. (1994) *Infect. Immunol.*, 62:1669–1676]. Thus, many chimeric HBc particles are so unstable that they fall apart during purification to such an extent that they are unrecoverable or they show very poor stability characteristics, making them problematic for vaccine development.

Chimeric hepatitis B core particles have been prepared by heterologous expression in a wide variety of organisms, including *E. coli, B. subtilis*, Vaccinia, *Salmonella typhimurium, Saccharomyces cerevisiae*. See, for example Pumpens et al., (1995) *Intervirology*, 38:63–74 , and the citations therein that note the work of several research groups, other than the present inventors.

A structural feature whereby the stability of full-length HBc particles could be retained, while abrogating the nucleic acid binding ability of full-length HBc particles, would be highly beneficial in vaccine development using the hepadnaviral nucleocapsid delivery system. Indeed, Ulrich et al. in their recent review of the use of HBc chimers as carriers for foreign epitopes [*Adv. Virus Res.*, vol. 50 (1998) Academic Press pages 141–182] note three potential problems to be solved for use of those chimers in human vaccines. A first potential problem is the inadvertent transfer of nucleic acids in a chimer vaccine to an immunized host. A second potential problem is interference from preexisting immunity to HBc. A third possible problem relates to the requirement of reproducible preparation of intact chimer particles that can also withstand long-term storage.

Initial evaluation of a particle displaying epitopes from *P. falciparum* [CS-2; Schodel et al., *J. Exp. Med.*, (1994) 180(3): p. 1037–46] was encouraging. However, using that particle as an immunogen in a vaccine in mice, provided antibody titers that were lower than those observed for the *P. berghei* and *P. yoelii* particles.

There are recognized to be two main CS-repeat epitopes associated with *P. vivax* (type-I and type-II), and a third, reported in 1993 and called 'vivax-like', which is identical to the CS-repeat from the monkey parasite (*P. siminovale*) resembling *P. ovale* [Qari et al., *Lancet*, 1993. 341(8848): p. 780–783]. For simplicity, this CS-repeat is referred to herein as *P. vivax* type-III.

The benefits of the inclusion of a universal T (Th) cell epitope derived from the malaria parasite are several-fold. First, the priming of malaria-specific Th cells ensures that, should a vaccine recipient be exposed to malaria, a more rapid and stronger anti-malaria response is activated due to previous priming of malaria specific T-helper cells. Secondly, vaccinees living in malaria endemic regions experience natural 'boosting' every time they are exposed to the parasite, because their immune systems have been primed at both the B and Th cell level. This effect is similar to clinical boosting by re-vaccination, a process that can be difficult to coordinate in developing countries where malaria is endemic.

Although the CS gene is largely invariant, limited sequence variation has been noted to occur mainly in the immunodominant T cell epitopic domains. The fact that genetic mutations always appear to result in amino acid substitutions suggests that pressure at the protein level, possibly immunological pressure, has selected for variation. Typically, the problems associated with amino acid variability of an epitope can only be resolved by the inclusion of multiple variants of the epitope. However, Nardin and coworkers at New York University recently identified a consensus form of the T cell epitope CS 326–345 that appears to bind all class II MHC molecules [Calvo-Calle et al., *J. Immunol.*, (1993) 150(4): p. 1403–1412 and Moreno et al., *J. Immunol.*, (1993) 151(1): p. 489–499].

Studies have shown that this consensus epitope is 'universal', like the T cell help afforded by HBc, and suggests that it primes malaria-specific Th cells in essentially all vaccine recipients. The fact that this epitope of the CS protein was identified by CD4+ T cells of volunteers that were protected against malaria following exposure to irradiated sporozoites, confirms that it is efficiently processed and presented in vivo by antigen presenting cells (APC) when presented in the context of sporozoite [Moreno et al., *Int. Immunol.*, (1991) 3(10): p. 997–1003]. The identification of this epitope was a significant advancement in the task of developing a pre-erythrocytic stage malaria vaccine.

As disclosed hereinafter, the present invention provides a contemplated HBc chimer that provides unexpectedly high titers of antibodies against malaria sporozoites, and in one aspect also provides a solution to the problems of HBc chimer stability as well as the substantial absence of nucleic acid binding ability of the construct. In addition, a contemplated recombinant chimer exhibits minimal, if any, antigenicity toward preexisting anti-HBc antibodies.

BRIEF SUMMARY OF THE INVENTION

The present invention contemplates an immunogen for inducing antibodies to the malaria-causing parasite, *Plasmodium*, and particularly the species *P. falciparum* and *P. vivax*, and a vaccine comprising that immunogen dispersed in a physiologically tolerable diluent. A contemplated immunogen is a recombinant hepatitis B virus core (HBc) protein chimer molecule with a length of about 140 to about 310 amino acid residues that contains four peptide-linked amino acid residue sequence domains from the N-terminus that are denominated Domains I, II, III and IV.

The first domain, Domain I, comprises about 71 to about 85 amino acid residues whose sequence includes at least the sequence of the residues of position 5 through position 75 of HBc.

The second domain, Domain II, comprises about 18 to about 58 amino acid residues peptide-bonded to residue 75 of which (i) a sequence of HBc is present from HBc positions 76 through 85 and (ii) a sequence of 8 to about 48 residues that constitute a B cell epitope of the CS protein of a species of the parasite *Plasmodium* that is peptide-bonded between the HBc residues of positions 78 and 79.

The third domain, Domain III, is an HBc sequence from position 86 through position 135 peptide-bonded to residue 85.

The fourth domain, Domain IV, comprises (i) zero to fourteen residues of a HBc amino acid residue sequence from position 136 through 149 peptide-bonded to the residue of position 135 of Domain III, (ii) zero to three cysteine residues, (iii) fewer than three arginine or lysine residues, or mixtures thereof adjacent to each other, and (iv) up to about 100 amino acid residues in a sequence heterologous to HBc from position 150 to the C-terminus, with the proviso that at least five amino acid residues are present of the amino acid residue sequence from position 136 through 149; i.e., residues of positions 136–140, when (a) zero cysteine residues are present and (b) fewer than about five heterologous amino acid residues are present, thus, Domain IV contains at least 5 residues.

In preferred embodiments, the immunogen is in the form of self-assembled particles and the *Plasmodium* B cell epitope is that of *P. falciparum* or *P. vivax*. It is also preferred that the HBc sequence of Domain I includes the residues of position 1 through position 75 with no additional residues at the N-terminus. It is further preferred that a contemplated immunogen contain one cysteine residue within Domain IV in an amino acid residue sequence heterologous to that of HBc from position 150 to the C-terminus. It is particularly preferred that that heterologous sequence comprise a T cell epitope from the same species of Plasmodium as the B cell epitope.

Another embodiment comprises an inoculum or vaccine that comprises an above HBc chimer particle that is dissolved or dispersed in a pharmaceutically acceptable diluent composition that typically also contains water. When administered in an immunogenic effective amount to an animal such as a mammal or bird, an inoculum induces antibodies that immunoreact specifically with the chimer particle or the conjugated (pendently-linked) hapten. The antibodies so induced also preferably immunoreact specifically with (bind to) an antigen containing the hapten, such as a protein where the hapten is a peptide or a saccharide where the hapten is an oligosaccharide.

The present invention has several benefits and advantages.

A particular benefit of the invention is that its use as a vaccine provides extraordinary antibody titers against the *Plasmodium* species of the B cell epitope.

An advantage of the invention is that those very high antibody titers have been produced with the aid of an adjuvant approved for use in humans.

Another benefit of the invention is that the recombinant immunogen is prepared easily and using well known cell culture techniques.

Another advantage of the invention is that the immunogen is easily prepared using well known recombinant techniques.

Yet another benefit of the invention is that a preferred immunogen exhibits greater stability at elevated temperatures than to other HBc chimers.

Yet another advantage of the invention is that a contemplated immunogen is substantially free of nucleic acids.

Still further benefits and advantages will be apparent to the worker of ordinary skill from the disclosure that follows.

BRIEF DESCRIPTION OF THE DRAWINGS

In the drawings forming a portion of this disclosure:

FIG. 1 shows the modifications made to commercial plasmid vector pKK223-3 in the preparation of plasmid vector pKK223-3N used herein for preparation of recombinant HBc chimers. The modified sequence (SEQ ID NO:180) is shown below the sequence of the commercially available vector (SEQ ID NO:181). The bases of the added NcoI site are shown in lower case letters and the added bases are shown with double underlines, whereas the deleted bases are shown as dashes. The two restriction sites present in this segment of the sequence (NcoI and HindIII) are indicated.

FIG

Figure 2B:
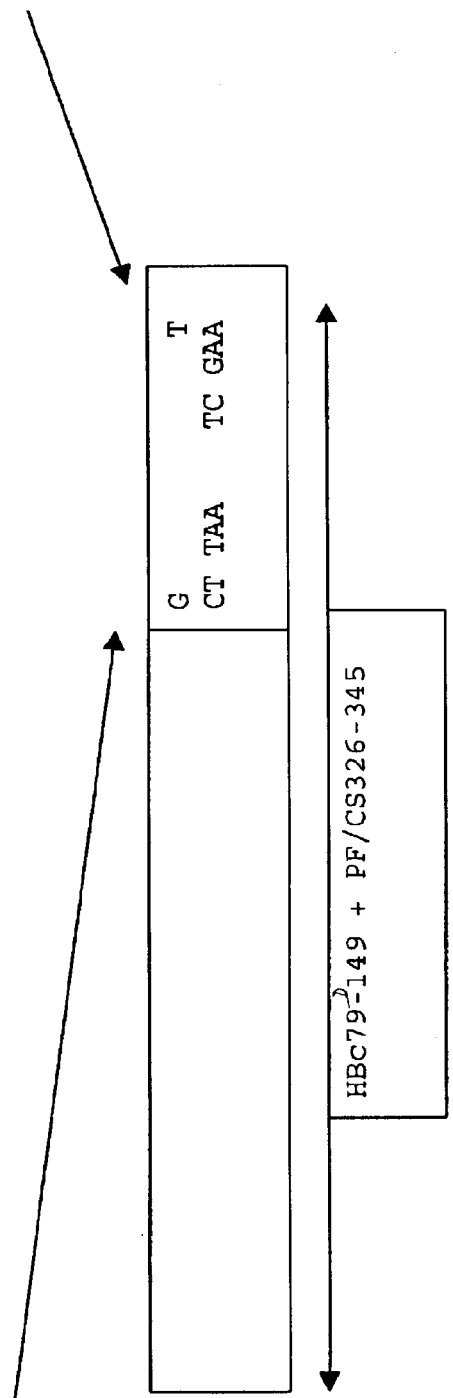
FIG. 2B shows DNA (double stranded and encoded amino acid residue sequence) that encodes a T cell epitope such as that referred to as Pf/CS326–345 (Pf/CS-UTC) and a stop codon (SEQ ID NOs:79 and 80) cloned into the EcoRI and HindIII sites at the C-terminus of an engineered, truncated HBc gene containing the first 149 HBc residues (HBc149). PCR amplification of the construct of FIG. 2B using a primer having a 5'-terminal SacI restriction site adjacent to a HBc-encoding sequence beginning at residue position 79 followed by digestion of the amplified sequence and the construct of FIG. 2A with SacI, followed by ligation of the appropriate portions is shown in FIG. 2C to form a single gene construct referred to hereinafter as V12 that encodes a B cell- and T cell-containing immunogen for a vaccine against P. falciparum.

The term "Domain" is used herein to mean a portion of a recombinant HBc chimer molecule that is identified by (i) residue position numbering relative to the position numbers of HBcAg subtype ayw as reported by Galibert et al., (1979) *Nature*, 281:646–650 (SEQ ID NO:170). The polypeptide portions of at least chimer Domains I, II and III are believed to exist in a similar tertiary form to the corresponding sequences of naturally occurring HBcAg.

As used herein, the term "fusion protein" designates a polypeptide that contains at least two amino acid residue sequences not normally found linked together in nature that are operatively linked together end-to-end (head-to-tail) by a peptide bond between their respective carboxy- and amino-terminal amino acid residues. The fusion proteins of the present invention are HBc chimers that induce the production of antibodies that immunoreact with a polypeptide or pathogen-related immunogen that corresponds in amino acid residue sequence to the polypeptide or pathogen-related portion of the fusion protein.

The phrase "hepatitis B" as used here refers in its broadest context to any member of the family hepadnaviridae, as discussed before.

The term "residue" is used interchangeably with the phrase amino acid residue.

DETAILED DESCRIPTION OF THE INVENTION

The present invention contemplates an immunogen and a vaccine comprising that immunogen against the malaria parasite, particularly those that infect humans; i.e., *P. falciparum* and *P. vivax*. Historically, one of the main shortfalls of peptide-based vaccines has been the lack of persistence of antibody following immunization. As discussed hereinafter, using the HBc chimer immunogen applied to *P. falciparum* vaccine development, high titers of neutralizing antibody are maintained for more than 6 months in mice following a 2-dose immunization regimen. This is consistent with and superior to the protection studies in the *P. yoelii* model using a similar but differently constructed immunogen, in which immunity obtained from challenge infection was evident 3 months after immunization using an immunogen different from that used here. [Schodel et al., *Behring Inst. Mitt.*, 1997(98): p. 114–119.]

A contemplated immunogen is a recombinant hepatitis B virus core (HBc) protein chimer molecule with a length of about 140 to about 310 and preferably about 155 to 235 amino acid residues that contains four peptide-linked amino acid residue sequence domains from the N-terminus that are denominated Domains I, II, III and IV.

(a) Domain I comprises about 71 to about 85 amino acid residues whose sequence includes at least the sequence of the residues of position 5 through position 75 of HBc.

(b) Domain II comprises about 11 to about 58 amino acid residues peptide-bonded to residue 75. This sequence includes (i) a sequence of HBc from HBc positions 76 through 85 and (ii) a sequence of 8 to about 48 residues that constitute a B cell epitope of the circumsporozoite protein of a species of the parasite *Plasmodium* that is peptide-bonded between the HBc residues of positions 78 and 79.

(c) Domain III is an HBc sequence from position 86 through position 135 that is peptide-bonded to residue 85.

d) Domain IV comprises (i) zero to fourteen residues of a HBc amino acid residue sequence from position 136 through 149 peptide-bonded to the residue of position 135 of Domain III, (ii) zero to three cysteine residues, (iii) fewer than three arginine or lysine residues, or mixtures thereof adjacent to each other, and (iv) up to 100, and preferably up to 25, amino acid residues in a sequence heterologous to HBc from position 150 to the C-terminus, with the proviso that at least five amino acid residues of the amino acid residue sequence from position 136 through 149; i.e., residues of positions 136–140, are present when (a) zero cysteine residues are present and (b) fewer than about five heterologous amino acid residues are present.

In examining the length of a contemplated HBc chimer, such a recombinant protein can have a length of about 140 to about 310 amino acid residues. Preferably, that length is about 155 to about 235 residues. More preferably, the length is about 165 to about 210 residues. Most preferably, the length is about 190 to about 200 residues. These differences in length arise from changes in the length of Domains I, II and IV.

HBc chimers having a Domain I that contains more than a deletion of the first three amino-terminal (N-terminal) residues have been reported to result in the complete disappearance of HBc chimer protein in *E. coli* cells. Pumpens et al., (1995) *Intervirology*, 38:63–74. On the other hand, a recent study in which an immunogenic 23-mer polypeptide from the influenza M2 protein was fused to the HBc N-terminal sequence reported that the resultant fusion protein formed particles when residues 1–4 of the native HBc sequence were replaced. Neirynck et al. (October 1999) *Nature Med.*, 5(10):1157–1163. Thus, the art teaches that particles can form when an added amino acid sequence is present peptide-bonded the one of residues 1–5 of HBc, whereas particles do not form if no additional sequence is present and more than residues 1–3 are deleted from the N-terminus of HBc.

An N-terminal sequence peptide-bonded to one of the first five N-terminal residues of HBc can contain a sequence of up to about 25 residues that are heterologous to HBc. Exemplary sequences include a B cell or T cell epitope such as those discussed hereinafter, a sequence of another (heterologous) protein such as β-galactosidase as can occur in fusion proteins as a result of the expression system used, or another hepatitis B-related sequence such as that from the Pre-S1 or Pre-S2 regions or the major HbsAg immunogenic sequence.

Domain I preferably has the sequence of residues of positions 1 through 75 of HBc, and is free of added residues at the amino-terminus (N-terminus). Domain I is also therefore preferably free of deletions of residues of positions 1–3.

Domain II, which is peptide-bonded to residue 75, contains the sequence of HBc residues of positions 76 through 85, and has a malarial B cell epitope whose length is 8 through about 28 residues peptide-bonded between residues 78 and 79. Preferred malarial B cell epitopes are discussed hereinafter.

Preferred malarial B cell epitopes for insertion between residues 78 and 79 of a recombinant HBc chimer are enumerated in Table A, below.

TABLE A

| Malarial B Cell Epitopes |  |
| --- | --- |
| *P. falciparum* |  |
| (NANP)₄ | SEQ ID NO: 1 |
| NANPNVDP(NANP)₃NVDP | SEQ ID NO: 2 |
| NANPNVDP(NANP)₃ | SEQ ID NO: 3 |

TABLE A-continued

Malarial B Cell Epitopes

| | |
|---|---|
| (NANP)$_3$NVDPNANP | SEQ ID NO: 4 |
| NANPNVDP(NANP)$_3$NVDPNANP | SEQ ID NO: 5 |
| NPNVDP(NANP)$_3$NV | SEQ ID NO: 6 |
| NPNVDP(NANP)$_3$NVDP | SEQ ID NO: 7 |
| NPNVDP(NANP)$_3$NVDPNA | SEQ ID NO: 8 |
| NVDP(NANP)$_3$NV | SEQ ID NO: 9 |
| NVDP(NANP)$_3$NVDP | SEQ ID NO: 10 |
| NVDP(NANP)$_3$NVDPNA | SEQ ID NO: 11 |
| DP(NANP)$_3$NV | SEQ ID NO: 12 |
| DP(NANP)$_3$NVDP | SEQ ID NO: 13 |
| DP(NANP)$_3$NVDPNA | SEQ ID NO: 14 |
| *P. vivax* | |
| DRAAGQPAGDRADGQPAG | SEQ ID NO: 15 |
| ANGAGNQPGANGAGDQPGA-NGADNQPGANGADDQPG | SEQ ID NO: 16 |
| ANGAGNQPGANGAGDQPG | SEQ ID NO: 17 |
| ANGADNQPGANGADDQPG | SEQ ID NO: 18 |
| ANGAGNQPGANGADNQPG | SEQ ID NO: 19 |
| ANGADNQPGANGADDQPG | SEQ ID NO: 20 |
| APGANQEGGAAAPGANQEGGAA | SEQ ID NO: 21 |
| *P. bergeii* | |
| (DP$_4$NPN)$_2$ | SEQ ID NO: 22 |
| *P. yoelli* | |
| (QGPGAP)$_4$ | SEQ ID NO: 23 |

Domain III contains the sequence of HBc position 86 through position 135 peptide-bonded at its N-terminus to residue 85.

Domain IV comprises (i) zero to fourteen residues of a HBc amino acid residue sequence from position 136 through 149 peptide-bonded to the residue of position 135 of Domain III, (ii) zero to three cysteine residues, (iii) fewer than three arginine or lysine residues, or mixtures thereof adjacent to each other, and (iv) up to about 100 amino acid residues in a sequence heterologous to HBc from position 150 to the C-terminus (typically as one or more T cell epitopes), with certain provisos. Although Domain IV can contain up to about 100 residues that are heterologous to HBc from position 150 through the C-terminus, this domain needs no residues in addition to those recited before to provide an effective immunogen.

However, when the chimeric protein ends at HBc residue 135, desired, particularly immunogenic particles do not form even when a C-terminal cysteine is present. On the other hand, desired particles do form when residues of positions 136–140 are present with or without an added C-terminal cysteine or when (a) one cysteine residue is present and (b) about five heterologous amino acid residues are also present peptide-bonded to HBc residue 135. Put differently, Domain IV can end at HBc residue 135 so long as at least five heterologous residues are present and a cysteine residue is also present. Otherwise, Domain IV ends at least at HBc residue 140. Thus, Domain IV contains at least 5 amino acid residues.

It is preferred that Domain IV contain up to fourteen residues of an HBc sequence from position 136 through position 149 peptide-bonded to residue 135; i.e., an HBc sequence that begins with the residue of position 136 that can continue through position 149. Thus, if the residue of position 148 is present, so is the sequence of residues of positions 136 through 147, or if residue 141 is present, so is the sequence of residues of positions 136 through 140.

In one embodiment, Domain IV comprises a sequence of HBc from residue 136 through 140 peptide-bonded to the residue of position 135 of Domain III. The remainder of Domain IV contains (i) zero to nine residues of a HBc amino acid residue sequence from position 141 through 149 peptide-bonded to the position 136–140 sequence, (ii) zero to three cysteine residues, (iii) fewer than three arginine or lysine residues, or mixtures thereof adjacent to each other, and (iv) up to 50 amino acid residues, and more preferably up to about 25 residues, in a sequence that constitutes a T cell epitope of the same species of *Plasmodium* as the B cell epitope peptide-bonded to the final HBc amino acid residue present in the chimer or a cysteine residue. Thus, for example, the T cell epitope can be bonded to the carboxy-terminal-most HBc residue such as residue 149, or to a cysteine residue that is bonded to that final HBc residue.

Domain IV can also contain zero to three cysteine residues and those Cys residues are present within about 30 residues of the carboxy-terminus (C-terminus) of the chimer molecule. Preferably, one cysteine (Cys) residue is present, and that Cys is preferably present as the carboxy-terminal (C-terminal) residue, unless a malarial T cell epitope is present as part of Domain IV. When such a T cell epitope is present, the preferred Cys is preferably within the C-terminal last five residues of the HBc chimer. Preferred malarial T cell epitopes are discussed hereinafter.

Figure 3:
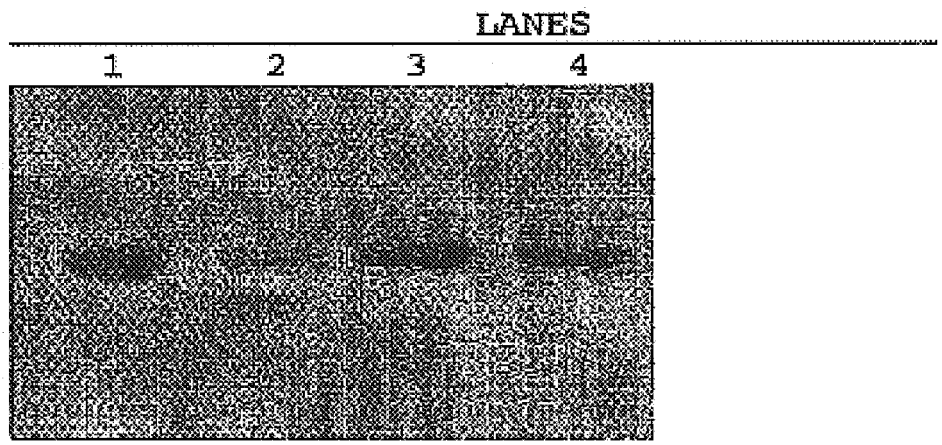
Figure 4:
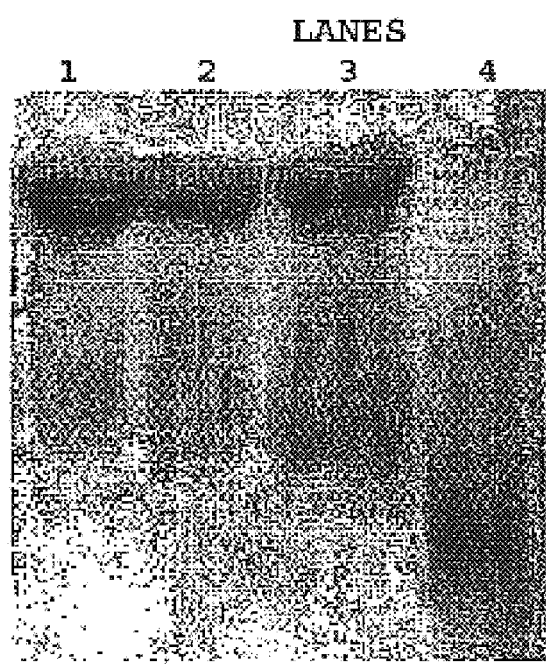
Figure 7:
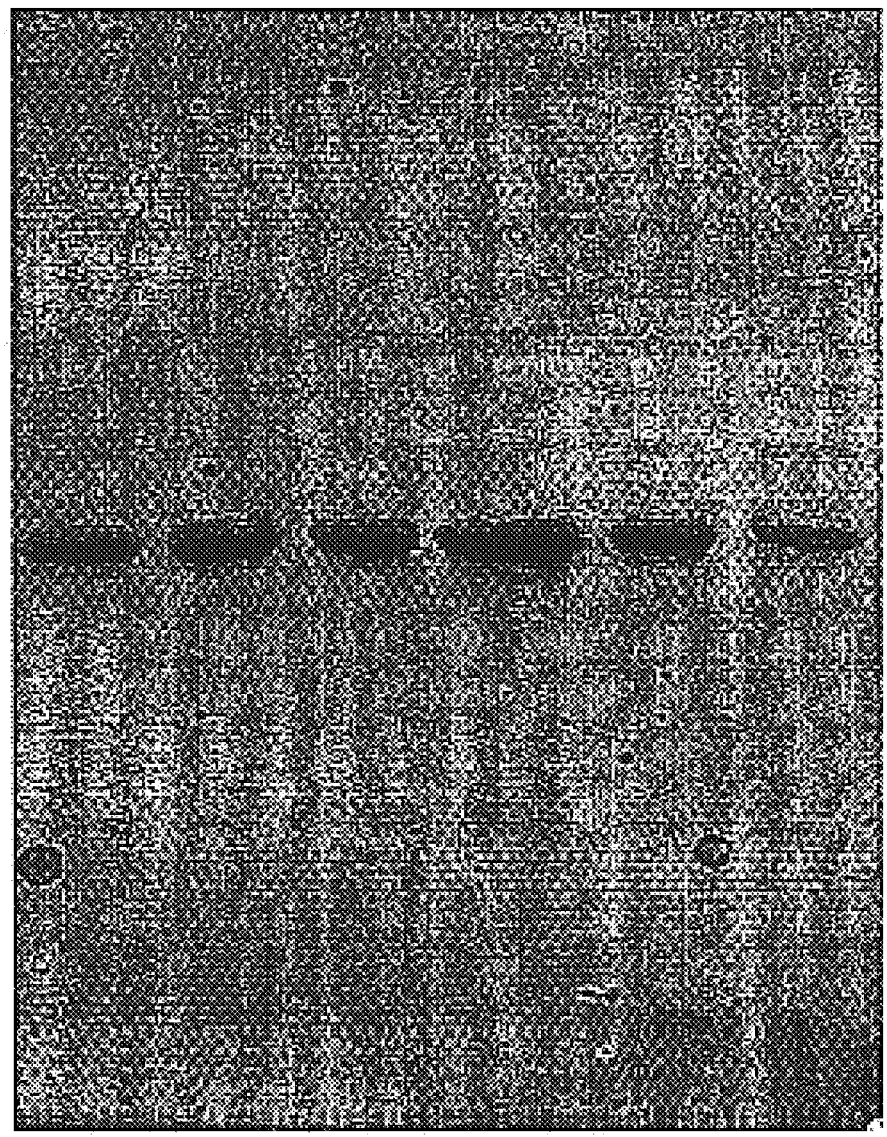

The presence of the above-discussed cysteine residue(s) provides an unexpected enhancement of the ability of the chimer molecules to form immunogenic particles, as well as unexpected thermal stability to an immunogen particle (discussed hereinafter). Thus, a preferred HBc chimer immunogen tends to be stable to decomposition at 37° C. to a greater extent than does a similar chimer lacking that cysteine residue. This enhanced stability is illustrated in FIGS. 3, 4 and 7, and is discussed hereinafter.

Domain IV contains fewer than three arginine or lysine residues, or mixtures thereof adjacent to each other. Arginine and lysines are present in the C-terminal region of HBc that extends from position 150 through the C-terminus of the native molecule. That region is sometimes referred to in the art as the "protamine" or "arginine-rich" region of the molecule and is thought to bind to nucleic acids. A contemplated HBc chimer molecule and particle are substantially free of bound nucleic acids.

The substantial freedom of nucleic acid binding can be readily determined by a comparison of the absorbance of the particles in aqueous solution measured at both 280 and 260 nm; i.e., a 280/260 absorbance ratio. The contemplated particles do not bind substantially to nucleic acids that are oligomeric and/or polymeric DNA and RNA species originally present in the cells of the organism used to express the protein. Such nucleic acids exhibit an absorbance at 260 nm and relatively less absorbance at 280 nm, whereas a protein such as a contemplated chimer absorbs relatively less at 260 nm and has a greater absorbance at 280 nm.

Thus, recombinantly expressed HBc particles or chimeric HBc particles that contain the arginine-rich sequence at residue positions 150–183 (or 150–185) exhibit a ratio of absorbance at 280 nm to absorbance at 260 nm (280:260 absorbance ratio) of about 0.8, whereas particles free of the arginine-rich nucleic acid binding region of naturally occurring HBc such as those that contain fewer than three arginine or lysine residues or mixtures thereof adjacent to each other, or those having a native or chimeric sequence that ends at about HBc residue position 140 to position 149, exhibit a 280:260 absorbance ratio of about 1.2 to about 1.6.

Chimeric HBc particles of the present invention are substantially free of nucleic acid binding and exhibit a 280:260 absorbance ratio of about 1.2 to about 1.6, and more typically, about 1.4 to about 1.6. This range is due in large part to the number of aromatic amino acid residues present in Domains II and IV of a given chimeric HBc particle. That range is also in part due to the presence of the Cys in Domain IV of a contemplated chimer, whose presence can diminish the observed ratio by about 0.1 for a reason that is presently unknown.

The contemplated chimer HBc particles are more stable in aqueous buffer at 37° C. over a time period of about two weeks to about one month than are particles formed from a HBc chimer containing the same peptide-linked Domain I, II and III sequences and an otherwise same Domain IV sequence in which the one to three cysteine residues [C-terminal cysteine residue(s)] are absent or a single C-terminal residue present is replaced by another residue such as an alanine residue. Stability of various chimer particles is determined as discussed hereinafter.

Thus, for example, particles containing a heterologous malarial epitope in Domain II [e.g. (NANP)$_4$] and a single cysteine residue C-terminal to residue valine 149 is more stable than otherwise identical particles assembled from chimer molecules whose C-terminal residue is valine 149. Similarly, particles containing the above malarial B cell epitope in Domain II and the universal malarial T cell epitope that contains a single cysteine near the C-terminus are more stable than are otherwise identical particles in which that cysteine is replaced by an alanine residue. See, FIGS. 3, 4 and 7 and the discussion relating thereto hereinafter.

A contemplated particle containing a C-terminal cysteine residue is also typically prepared in greater yield than is a particle assembled from a chimer molecule lacking a C-terminal cysteine. This increase in yield can be seen from the mass of particles obtained or from integration of traces from analytical gel filtration analysis using Superose® 6 HR as discussed hereinafter and shown in Tables 9A and 9B.

Although the T cell help afforded by HBc is highly effective in enhancing antibody responses (i.e. B cell-mediated) to 'carried' epitopes following vaccination, HBc does not activate malaria-specific T cells, except in restricted individuals for whom the B cell epitope is also a T cell epitope. To help ensure universal priming of malaria-specific T helper cells, in addition to B cells, one or more malaria-specific T helper epitopes is preferably incorporated into a contemplated immunogen and is located in Domain IV of the immunogen.

A particularly preferred recombinant HBc chimer includes a T cell epitope of the same *Plasmodium* species as the B cell epitope. Thus, where the B cell epitope of Domain II is that of *P. falciparum*, the T cell epitope is also that of *P. falciparum*, and the like. Using this matching strategy, T cells are primed to the same species as that to which antibodies are initially induced by the B cell epitope. Particularly preferred T cell epitopes present as a part of Domain IV are enumerated in Table B, below.

TABLE B

| Malarial Universal T Cell Epitope | |
|---|---|
| *P. falciparum* GIEYLNKIQNSLSTEWSPCSVT | SEQ ID NO:24 |
| *P. vivax* YLDKVRATVGTEWTPCSVT | SEQ ID NO:25 |
| *P. yoelli* EFVKQISSQLTEEWSQCSVT | SEQ ID NO:26 |

A plurality of the above or another T cell epitopes can be present in Domain IV or another B cell epitope can be present. In preferred practice, Domain IV has up to about 50 residues in a sequence heterologous to HBc. Most preferably, that sequence is up to about 25 residues and includes one of the universal T cell epitopes shown in Table B, above.

A contemplated recombinant HBc chimer molecule is typically present and is used in an immunogen or vaccine as a self-assembled particle. These particles are comprised of 180 to 240 chimer molecules that separate into protein molecules in the presence of disulfide reducing agents such as 2-mercaptoethanol, and the individual molecules are therefore thought to be bound together into the particle primarily by disulfide bonds. These particles are similar to the particles observed in patients infected with HBV, but these particles are non-infectious. Upon expression in various prokaryotic and eukaryotic hosts, the individual recombinant HBc chimer molecules assemble in the host into particles that can be readily harvested from the host cells.

The amino acid sequence of HBc from residue position 1 through at least position 140 is preferably present in a contemplated chimer molecule and particle. The sequence from position 1 through position 149 is more preferably present. A malarial B cell epitope is present between residues 78 and 79 and a single cysteine residue or a malarial T cell epitope containing a cysteine residue is preferably present as a C-terminal addition to the HBc sequence as part of Domain IV. A contemplated recombinant HBc chimer is substantially free of bound nucleic acid. A preferred chimer particle that contains an added Cys residue at or near the C-terminus of the molecule is also more stable at 37° C. than is a similar particle that does not contain that added Cys.

In addition to the before-discussed N- and C-truncations and insertion of malarial epitopes, a contemplated chimer molecule can also contain conservative substitutions in the amino acid residues that constitute HBc Domains I, II, III and IV. Conservative substitutions are as defined before.

More rarely, a "nonconservative" change, e.g., replacement of a glycine with a tryptophan is contemplated. Analogous minor variations can also include amino acid deletions or insertions, or both. Guidance in determining which amino acid residues can be substituted, inserted, or deleted without abolishing biological activity can be found using computer programs well known in the art, for example LASERGENE software (DNASTAR Inc., Madison, Wis.)

The HBc portion of a chimer molecule of the present invention [the portion having the HBc sequence that has other than a sequence of an added epitope, or heterologous residue(s) that are a restriction enzyme artifact] most preferably has the amino acid residue sequence at positions 1 through 149 of subtype ayw that is shown in FIG. 6 (SEQ ID NO:170), when present. Somewhat less preferred are the corresponding amino acid residue sequences of subtypes adw, adw2 and adyw that are also shown in FIG. 6 (SEQ ID NOs:171, 172 and 173). Less preferred still are the sequences of woodchuck and ground squirrel at aligned positions 1 through 149 that are the last two sequences of FIG. 6 (SEQ ID NOs:174 and 168). As noted elsewhere, portions of different sequences from different mammalian HBc proteins can be used together in a single chimer.

When the HBc portion of a chimer molecule of the present invention has other than a sequence of a mammalian HBc molecule at positions 1 through 149, when present, because one or more conservative substitutions has been made, it is preferred that no more than 10 percent, and more preferably no more than 5 percent, and most preferably no more than 3 percent of the amino acid residues are substituted as compared to SEQ ID NO:170 from position 1 through 149. A contemplated chimer of 149 HBc residues can therefore contain up to about 15 residues that are different from those of SEQ ID NO:170 at positions 1 through 149, and preferably about 7 or 8 residues. More preferably, up to about 5 residues are different from the ayw sequence (SEQ ID NO:170) at residue positions 1–149. Where a HBc sequence is truncated further at one or both termini, the number of substituted residues is proportionally different. Deletions elsewhere in the molecule are considered conservative substitutions for purposes of calculation.

Chimer Preparation

A contemplated chimeric immunogen is prepared using the well known techniques of recombinant DNA technology. Thus, sequences of nucleic acid that encode particular polypeptide sequences are added and deleted from the precursor sequence that encodes HBV.

As was noted previously, the HBc immunodominant loop is usually recited as being located at about positions 75 through 85 from the amino-terminus (N-terminus) of the intact protein. The malarial B cell epitope-containing sequence is placed into that immunodominant loop sequence of Domain II. That placement substantially eliminates the HBc immunogenicity and antigenicity of the HBc loop sequence, while presenting the malarial B cell epitope in an extremely immunogenic position in the assembled chimer particles.

One of two well-known strategies is particularly useful for placing the malarial B cell sequence into the loop sequence at the desired location between residues 78 and 79. A first, less successful strategy is referred to as replacement in which DNA that codes for a portion of the loop is excised and replaced with DNA that encodes a malarial B cell sequence. The second strategy is referred to as insertion in which a malarial B cell sequence is inserted between adjacent residues in the loop.

Site-directed mutagenesis using the polymerase chain reaction (PCR) is used in one exemplary replacement approach to provide a chimeric HBc DNA sequence that encodes a pair of different restriction sites, e.g. EcoRI and SacI, one near each end of the immunodominant loop-encoding DNA. Exemplary residues replaced are 76 through 81. The loop-encoding section is excised, a desired malarial B cell epitope-encoding sequence flanked on each side by appropriate HBc sequence residues is ligated into the restriction sites and the resulting DNA is used to express the HBc chimer. See, for example, Table 2 of Pumpens et al., (1995) *Intervirology*, 38:63–74 for exemplary uses of a similar technique.

Alternatively, a single restriction site or two sites can be encoded into the region, the DNA cut with a restriction enzyme(s) to provide "sticky" or ends, and an appropriate sticky- or blunt-ended heterologous DNA segment ligated into the cut region. Examples of this type of sequence replacement into HBc can be found in the work reported in Schodel et al., (1991) F. Brown et al. eds., *Vaccines* 91, Cold Spring Harbor Laboratory, Cold Spring Harbor, N.Y., pp. 319–325, Schodel et al., *Behring Inst. Mitt.*, 1997(98): p. 114–119 and Schodel et al., *J. Exp. Med.*, (1994) 180(3): p. 1037–4, the latter two papers discussing the preparation of vaccines against *P. yoelii* and *P. berghei*, respectively.

It has surprisingly been found that the insertion position within the HBc immunogenic loop and the presence of loop residues are of import to the activity of the immunogen. Thus, as is illustrated hereinafter, placement of a malarial B cell epitope between HBc residue positions 78 and 79 provides a particulate immunogen that is ten to one thousand times more immunogenic than placement of the same immunogen in an excised and replaced region between residues 76 and 81. In addition, placement of the same malarial immunogen between residues 78 and 79 as compared to between residues 77 and 78 provided an unexpected enhancement of about 15-fold. Thus, a replacement strategy that results in a net removal of residues from the immunodominant loop is not used herein.

Insertion is therefore preferred. In an illustrative example of the insertion strategy, site-directed mutagenesis is used to create two restriction sites adjacent to each other and between codons encoding adjacent amino acid residues, such as those at residue positions 78 and 79. This technique adds twelve base pairs that encode four amino acid residues (two for each restriction site) between formerly adjacent residues in the HBc loop.

Upon cleavage with the restriction enzymes, ligation of the DNA coding for the malarial sequence and expression of the DNA to form HBc chimers, the HBc loop amino acid sequence is seen to be interrupted on its N-terminal side by the two residues encoded by the 5' restriction site, followed toward the C-terminus by the malarial B-cell epitope sequence, followed by two more heterologous, non-loop residues encoded by the 3' restriction site and then the rest of the loop sequence. This same strategy is also preferably used for insertion into Domain IV of a T cell epitope or one or more cysteine residues that are not a part of a T cell epitope. A similar strategy using an insertion between residues 82 and 83 is reported in Schoedel et al., (1990) F. Brown et al. eds., *Vaccines* 90, Cold Spring Harbor Laboratory, Cold Spring Harbor, N.Y. pp. 193–198.

Figure 2C:
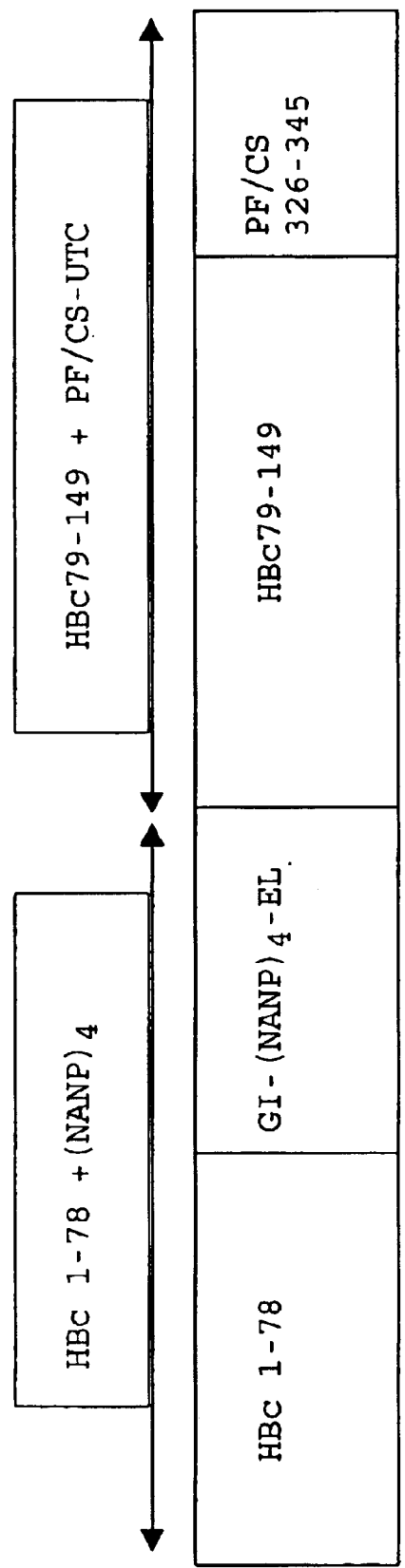
FIG. 2, shown in three panels as FIGS. 2A, 2B and 2C, schematically illustrates a preferred cloning strategy in which a malarial B cell epitope such as (NANP)$_4$ (SEQ ID NO:1) is cloned into the EcoRI and SacI sites of an engineered HBc gene (FIG. 2A) between positions 78 and 79, which destroys the EcoRI site, while preserving the SacI site.

More specifically, this cloning strategy is illustrated schematically in FIGS. 2A, 2B and 2C. In FIG. 2A, a DNA sequence that encodes a C-terminal truncated HBc sequence (HBc149) is engineered to contain adjacent EcoRI and SacI sites between residues 78 and 79. Cleavage of that DNA with both enzymes provides one fragment that encodes HBc positions 1–78 3'-terminated with an EcoRI sticky end, whereas the other fragment has a 5'-terminal SacI sticky end and encodes residues of positions 79–149. Ligation of a synthetic nucleic acid having a 5' AATT overhang followed by a sequence that encodes a desired malarial B cell epitope and a AGCT 3'overhang provides a HBc chimer sequence that encodes that B cell epitope flanked on each side by two heterologous residues (GI and EL, respectively) between residues 78 and 79, while destroying the EcoRI site and preserving the SacI site.

A similar strategy is shown in FIG. 2B for insertion of a cysteine-containing sequence, such as a particularly preferred T cell epitope such as that referred to as PF/CS326–345 (Pf-UTC). Here, EcoRI and HindIII restriction sites were engineered in to the HBc DNA sequence after amino acid residue position 149. After digestion with EcoRI and HindIII, a synthetic DNA having the above AATT 5'overhang followed by a T cell epitope-encoding sequence, a stop codon and a 3' AGCT overhang were ligated into the digested sequence to form a sequence that encoded HBc residues 1–149 followed by two heterologous residues (GI), the stop codon and the HindIII site.

PCR amplification using a forward primer having a SacI restriction site followed by a sequence encoding HBc beginning at residue position 79, followed by digestion with SacI and HindIII provided a sequence encoding HBc positions 79–149 plus the two added residues and the T cell epitope at the C-terminus. Digestion of the construct of FIG. 2B with SacI and ligation provided the complete gene encoding a desired recombinant HBc chimer immunogen having the sequence, from the N-terminus, of HBc positions 1–78, two added residues, the malarial B cell epitope, two added residues, HBc positions 79–149, two added residues, and the T cell epitope that is shown in FIG. 2C.

It is noted that the preferred use of two heterologous residues on either side of (flanking) a B cell or T cell epitope is a matter of convenience. As a consequence, one can also use zero to three or more added residues that are not part of the HBc sequence on either or both sides of an inserted sequence. One or both ends of the insert and HBc nucleic acid can be "chewed back" with an appropriate nuclease (e.g. S1 nuclease) to provide blunt ends that can be ligated together. Added heterologous residues that are neither part of the inserted B cell or T cell epitopes nor a part of the HBc sequence are not counted in the number of residues present in a recited Domain.

It is also noted that one can also synthesize all or a part of a desired recombinant HBc chimer nucleic acid using well-known synthetic methods as is discussed and illustrated in U.S. Pat. No. 5,656,472 for the synthesis of the 177 base pair DNA that encodes the 59 residue ribulose bis-phosphate carboxylase-oxygenase signal peptide of *Nicotiana tabacum*. For example, one can synthesize Domains I and II with a blunt or "sticky" end that can be ligated to Domains III and IV to provide a construct that expresses a contemplated HBc chimer that contains zero added residues to the N-terminal side of the B cell epitope and zero to three added residues on the C-terminal side or at the Domain II/III junction or at some other desired location.

A nucleic acid sequence (segment) that encodes a previously described HBc chimer molecule or a complement of that coding sequence is also contemplated herein. Such a nucleic acid segment is present in isolated and purified form in some preferred embodiments.

In living organisms, the amino acid residue sequence of a protein or polypeptide is directly related via the genetic code to the deoxyribonucleic acid (DNA) sequence of the gene that codes for the protein. Thus, through the well-known degeneracy of the genetic code additional DNAs and corresponding RNA sequences (nucleic acids) can be prepared as desired that encode the same chimer amino acid residue sequences, but are sufficiently different from a before-discussed gene sequence that the two sequences do not hybridize at high stringency, but do hybridize at moderate stringency.

High stringency conditions can be defined as comprising hybridization at a temperature of about 50°–55° C. in 6×SSC and a final wash at a temperature of 68° C. in 1–3×SSC. Moderate stringency conditions comprise hybridization at a temperature of about 50° C. to about 65° C. in 0.2 to 0.3 M NaCl, followed by washing at about 50° C. to about 55° C. in 0.2×SSC, 0.1% SDS (sodium dodecyl sulfate).

A nucleic sequence (DNA sequence or an RNA sequence) that (1) itself encodes, or its complement encodes, a chimer molecule whose HBc portion from residue position 1 through 136, when present, is that of SEQ ID NOs: 168, 170, 171, 172, 173 or 174 and (2) hybridizes with a DNA sequence of SEQ ID NOs: 169, 175, 176, 177, 178 or 179 at least at moderate stringency (discussed above); and (3) whose HBc sequence shares at least 80 percent, and more preferably at least 90 percent, and even more preferably at least 95 percent, and most preferably 100 percent identity with a DNA sequence of SEQ ID NOs: 169, 175, 176, 177, 178 and 179, is defined as a DNA variant sequence. As is well-known, a nucleic acid sequence such as a contemplated nucleic acid sequence is expressed when operatively linked to an appropriate promoter in an appropriate expression system as discussed elsewhere herein.

An analog or analogous nucleic acid (DNA or RNA) sequence that encodes a contemplated chimer molecule is also contemplated as part of this invention. A chimer analog nucleic acid sequence or its complementary nucleic acid sequence encodes a HBc amino acid residue sequence that is at least 80 percent, and more preferably at least 90 percent, and most preferably is at least 95 percent identical to the HBc sequence portion from residue position 1 through residue position 136 shown in SEQ ID NOs: 168, 170, 171, 172, 173 and 174. This DNA or RNA is referred to herein as an "analog of" or "analogous to" a sequence of a nucleic acid of SEQ ID NOs: 169, 175, 176, 177, 178 and 179, and hybridizes with the nucleic acid sequence of SEQ ID NOs: 169, 175, 176, 177, 178 and 179 or their complements herein under moderate stringency hybridization conditions. A nucleic acid that encodes an analogous sequence, upon suitable transfection and expression, also produces a contemplated chimer.

Different hosts often have preferences for a particular codon to be used for encoding a particular amino acid residue. Such codon preferences are well known and a DNA sequence encoding a desired chimer sequence can be altered, using in vitro mutagenesis for example, so that host-preferred codons are utilized for a particular host in which the enzyme is to be expressed. In addition, one can also use the degeneracy of the genetic code to encode the HBc portion of a sequence of SEQ ID NOs: 168, 170, 171, 172, 173 or 174 that avoids substantial identity with a DNA of SEQ ID Nos: 169, 175, 176, 177, 178 or 179, or their complements. Thus, a useful analogous DNA sequence need not hybridize with the nucleotide sequences of SEQ ID NOs: 169, 175, 176, 177, 178 or 179 or a complement under conditions of moderate stringency, but can still provide a contemplated chimer molecule.

A recombinant nucleic acid molecule such as a DNA molecule, comprising a vector operatively linked to an exogenous nucleic acid segment (e.g., a DNA segment or sequence) that defines a gene that encodes a contemplated chimer, as discussed above, and a promoter suitable for driving the expression of the gene in a compatible host organism, is also contemplated in this invention. More particularly, also contemplated is a recombinant DNA molecule that comprises a vector comprising a promoter for driving the expression of the chimer in host organism cells operatively linked to a DNA segment that defines a gene for the HBc portion of a chimer or a DNA variant that has at least 90 percent identity to the chimer gene of SEQ ID NOs: 169, 175, 176, 177, 178 or 179 and hybridizes with that gene under moderate stringency conditions.

Further contemplated is a recombinant DNA molecule that comprises a vector containing a promoter for driving the expression of a chimer in host organism cells operatively linked to a DNA segment that is an analog nucleic acid sequence that encodes an amino acid residue sequence of a HBc chimer portion that is at least 80 percent identical, more preferably 90 percent identical, and most preferably 95 percent identical to the HBc portion of a sequence of SEQ ID NOs: 168, 170, 171, 172, 173 or 174. That recombinant DNA molecule, upon suitable transfection and expression in a host cell, provides a contemplated chimer molecule.

It is noted that because of the 30 amino acid residue N-terminal sequence of ground squirrel HBc does not align with any of the other HBc sequences, that sequence and its encoding nucleic acid sequences and their complements are not included in the above percentages of identity, nor are the portions of nucleic acid that encode that 30-residue sequence or its complement used in hybridization determinations. Similarly, sequences that are truncated at either or both of the HBc N- and C-termini are not included in identity calculations, nor are those sequences in which residues of the immunodominant loop are removed for insertion of a heterologous epitope. Thus, only those HBc-encoding bases or HBc sequence residues that are present in a chimer molecule are included and compared to an aligned nucleic acid or amino acid residue sequence in the identity percentage calculations.

Inasmuch as the coding sequences for the gene disclosed herein is illustrated in SEQ ID NOs: 169, 175, 176, 177, 178 and 179, isolated nucleic acid segments, preferably DNA sequences, variants and analogs thereof can be prepared by in vitro mutagenesis, as is well known in the art and discussed in *Current Protocols In Molecular Biology*, Ausabel et al. eds., John Wiley & Sons (New York: 1987) p. 8.1.1–8.1.6, that begin at the initial ATG codon for a gene and end at or just downstream of the stop codon for each gene. Thus, a desired restriction site can be engineered at or upstream of the initiation codon, and at or downstream of the stop codon so that other genes can be prepared, excised and isolated.

As is well known in the art, so long as the required nucleic acid, illustratively DNA sequence, is present, (including start and stop signals), additional base pairs can usually be present at either end of the segment and that segment can still be utilized to express the protein. This, of course, presumes the absence in the segment of an operatively linked DNA sequence that represses expression, expresses a further product that consumes the enzyme desired to be expressed, expresses a product that consumes a wanted reaction product produced by that desired enzyme, or otherwise interferes with expression of the gene of the DNA segment.

Thus, so long as the DNA segment is free of such interfering DNA sequences, a DNA segment of the invention can be about 500 to about 15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known. Such long DNA segments are not preferred, but can be used.

DNA segments that encode the before-described chimer can be synthesized by chemical techniques, for example, the phosphotriester method of Matteucci et al. (1981) *J. Am. Chem. Soc.*, 103:3185. Of course, by chemically synthesizing the coding sequence, any desired modifications can be made simply by substituting the appropriate bases for those encoding the native amino acid residue sequence. However, DNA segments including sequences discussed previously are preferred.

A contemplated HBc chimer can be produced (expressed) in a number of transformed host systems, typically host cells although expression in acellular, in vitro, systems is also contemplated. These host cellular systems include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g. baculovirus); plant cell systems transformed with virus expression vectors (e.g. cauliflower mosaic virus; tobacco mosaic virus) or with bacterial expression vectors (e.g., Ti plasmid); or appropriately transformed animal cell systems such as CHO or COS cells. The invention is not limited by the host cell employed.

DNA segments containing a gene encoding the HBc chimer are preferably obtained from recombinant DNA molecules (plasmid vectors) containing that gene. Vectors capable of directing the expression of a chimer gene into the protein of a HBc chimer is referred to herein as an "expression vector".

An expression vector contains expression control elements including the promoter. The chimer-coding gene is operatively linked to the expression vector to permit the promoter sequence to direct RNA polymerase binding and expression of the chimer-encoding gene. Useful in expressing the polypeptide coding gene are promoters that are inducible, viral, synthetic, constitutive as described by Poszkowski et al. (1989) *EMBO J.*, 3:2719 and Odell et al. (1985) *Nature*, 313:810, as well as temporally regulated, spatially regulated, and spatiotemporally regulated as given in Chua et al. (1989) *Science*, 244:174–181.

One preferred promoter for use in prokaryotic cells such as *E. coli* is the Rec 7 promoter that is inducible by exogenously supplied nalidixic acid. A more preferred promoter is present in plasmid vector JHEX25 (available from Promega) that is inducible by exogenously supplied isopropyl-β-D-thiogalacto-pyranoside (IPTG). A still more preferred promoter, the tac promoter, is present in plasmid vector pKK223-3 and is also inducible by exogenously supplied IPTG. The pKK223-3 plasmid can be successfully expressed in a number of *E. coli* strains, such as XL-1, TB1, BL21 and BLR, using about 25 to about 100 μM IPTG for induction. Surprisingly, concentrations of about 25 to about 50 μM IPTG have been found to provide optimal results in 2 L shaker flasks and fermentors.

Several strains of Salmonella such as *S. typhi* and *S. typhimurium* and *S. typhimurium-E. coli* hybrids have been used to express immunogenic transgenes including prior HBc chimer particles both as sources of the particles for use as immunogens and as live, attenuated whole cell vaccines and inocula, and those expression and vaccination systems can be used herein. See, U.S. Pat. Nos. 6,024,961; 5,888, 799; 5,387,744; 5,297,441; Ulrich et al., (1998) *Adv. Virus Res.*, 50:141–182; Tacket et al., (August 1997) *Infect. Immun.*, 65(8):3381–3385; Schodel et al., (February 1997) *Behring Inst. Mitt.*, 98:114–119; Nardelli-Haefliger et al., (December 1996) *Infect. Immun.*, 64(12):5219–5224; Londono et al., (April 1996) *Vaccine*, 14(6):545–552, and the citations therein.

Expression vectors compatible with eukaryotic cells, such as those compatible with yeast cells or those compatible with cells of higher plants or mammals, are also contemplated herein. Such expression vectors can also be used to form the recombinant DNA molecules of the present invention. Vectors for use in yeasts such as *S. cerivisiae* or *Pichia pastoris* can be episomal or integrating, as is well known. Eukaryotic cell expression vectors are well known in the art and are available from several commercial sources. Normally, such vectors contain one or more convenient restriction sites for insertion of the desired DNA segment and promoter sequences. Optionally, such vectors contain a selectable marker specific for use in eukaryotic cells. Exemplary promoters for use in *S. cerevisiae* include the *S. cerevisiae* phosphoglyceric acid kinase (PGK) promoter and the divergent promoters GAL 10 and GAL 1, whereas the alcohol oxidase gene (AOX1) is a useful promoter for *Pichia pastoris*.

For example, to produce chimers in the methylotrophic yeast, *P. pastoris*, a gene that encodes a desired chimer is placed under the control of regulatory sequences that direct expression of structural genes in *Pichia*. The resultant expression-competent forms of those genes are introduced into *Pichia* cells.

More specifically, the transformation and expression system described by Cregg et al. (1987) *Biotechnology*, 5:479–485; (1987) *Molecular and Cellular Biology*, 12:3376–3385 can be used. A gene for a chimer V12.Pf3.1 is placed downstream from the alcohol oxidase gene (AOX1) promoter and upstream from the transcription terminator sequence of the same AOX1 gene. The gene and its flanking regulatory regions are then introduced into a plasmid that carries both the *P. pastoris* HIS4 gene and a *P. pastoris* ARS sequence (Autonomously Replicating Sequence), which permit plasmid replication within *P. pastoris* cells [Cregg et al. (1987) *Molecular and Cellular Biology*, 12:3376–3385].

The vector also contains appropriate portions of a plasmid such as pBR322 to permit growth of the plasmid in *E. coli* cells. The resultant plasmid carrying a chimer gene, as well as the various additional elements described above, is illustratively transformed into a his4 mutant of *P. pastoris*; i.e. cells of a strain lacking a functional histidinol dehydrogenase gene.

After selecting transformant colonies on media lacking histidine, cells are grown on media lacking histidine, but containing methanol as described Cregg et al. (1987) *Molecular and Cellular Biology*, 12:3376–3385, to induce the AOX1 promoters. The induced AOX1 promoters cause expression of the chimer protein and the production of chimer particles in *P. pastoris*.

A contemplated chimer gene can also be introduced by integrative transformation, which does not require the use of an ARS sequence, as described by Cregg et al. (1987) *Molecular and Cellular Biology*, 12:3376–3385.

Production of chimer particles by recombinant DNA expression in mammalian cells is illustratively carried out using a recombinant DNA vector capable of expressing the chimer gene in Chinese hamster ovary (CHO) cells. This is accomplished using procedures that are well known in the art and are described in more detail in Sambrook et al., *Molecular Cloning: A Laboratory Manual*, $2^{nd}$ ed., Cold Spring Harbor Laboratories (1989).

In one illustrative example, the simian virus (SV40) based expression vector, pKSV-10 (Pharmacia Fine Chemicals, Piscataway, N.J.), is subjected to restriction endonuclease digestion by NcoI and HindIII. A NcoI/HindIII sequence fragment that encodes the desired HBc chimer prepared as described in Example 1 is ligated into the expression plasmid, which results in the formation of a circular recombinant expression plasmid denominated pSV-Pf.

The expression plasmid pSV-Pf contains an intact *E. coli* ampicillin resistance gene. *E. coli* RR101 (Bethesda Research Laboratories, Gaithersburg, Md.), when transformed with pSV-Pf, can thus be selected on the basis of ampicillin resistance for those bacteria containing the plasmid. Plasmid-containing bacteria are then cloned and the clones are subsequently screened for the proper orientation of the inserted coding gene into the expression vector.

The above obtained plasmid, pSV-Pf, containing the gene that encodes a desired HBc chimer is propagated by culturing *E. coli* containing the plasmid. The plasmid DNA is isolated from *E. coli* cultures as described in Sambrook et al., above.

Expression of a chimer is accomplished by the introduction of pSV-Pf into the mammalian cell line, e.g., CHO cells, using the calcium phosphate-mediated transfection method of Graham et al. (1973) *Virol.*, 52:456, or a similar technique.

To help ensure maximal efficiency in the introduction of pSV-Pf into CHO cells in culture, the transfection is carried out in the presence of a second plasmid, pSV2NEO (ATCC #37149) and the cytotoxic drug G418 (GIBCO Laboratories, Grand Island, N.Y.) as described by Southern et al. (1982) *J. Mol. Appl. Genet.*, 1:327. Those CHO cells that are resistant to G418 are cultured, have acquired both plasmids, pSV2NEO and pSV-Pf, and are designated CHO/pSV-Pf cells. By virtue of the genetic architecture of the pSV-Pf expression vector, a chimer is expressed in the resulting CHO/pSV-Pf cells and can be detected in and purified from the cytoplasm of these cells. The resulting composition containing cellular protein is separated on a column as discussed elsewhere herein.

The choice of which expression vector and ultimately to which promoter a chimer-encoding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention can direct the replication, and preferably also the expression (for an expression vector) of the chimer gene included in the DNA segment to which it is operatively linked.

In one preferred embodiment, the host that expresses the chimer is the prokaryote, *E. coli*, and a preferred vector includes a prokaryotic replicon; i.e., a DNA sequence having the ability to direct autonomous replication and maintenance of the recombinant DNA molecule extrachromosomally in a prokaryotic host cell transformed therewith. Such replicons are well known in the art.

Those vectors that include a prokaryotic replicon can also include a prokaryotic promoter region capable of directing the expression of a contemplated HBc chimer gene in a host cell, such as *E. coli*, transformed therewith. Promoter sequences compatible with bacterial hosts are typically provided in plasmid vectors containing one or more convenient restriction sites for insertion of a contemplated DNA segment. Typical of such vector plasmids are pUC8, pUC9, and pBR329 available from Biorad Laboratories, (Richmond, Calif.) and pPL and pKK223-3 available from Pharmacia, Piscataway, N.J.

Typical vectors useful for expression of genes in cells from higher plants and mammals are well known in the art and include plant vectors derived from the tumor-inducing (Ti) plasmid of *Agrobacterium tumefaciens* described by Rogers et al. (1987) *Meth. in Enzymol.*, 153:253–277 and mammalian expression vectors pKSV-10, above, and pCI-neo (Promega Corp., #E1841, Madison, Wis.). However, several other expression vector systems are known to function in plants including pCaMVCN transfer control vector described by Fromm et al. (1985) *Proc. Natl. Acad. Sci.*

USA, 82:58–24. Plasmid pCaMVCN (available from Pharmacia, Piscataway, N.J.) includes the cauliflower mosaic virus CaMV 35S promoter.

The above plant expression systems typically provide systemic or constitutive expression of an inserted transgene. Systemic expression can be useful where most or all of a plant is used as the source to a contemplated chimer molecule or resultant particles or where a large part of the plant is used to provide an oral vaccine. However, it can be more efficacious to express a chimer molecule or particles in a plant storage organ such as a root, seed or fruit from which the particles can be more readily isolated or ingested.

One manner of achieving storage organ expression is to use a promoter that expresses its controlled gene in one or more preselected or predetermined non-photosynthetic plant organs. Expression in one or more preselected storage organs with little or no expression in other organs such as roots, seed or fruit versus leaves or stems is referred to herein as enhanced or preferential expression. An exemplary promoter that directs expression in one or more preselected organs as compared to another organ at a ratio of at least 5:1 is defined herein as an organ-enhanced promoter. Expression in substantially only one storage organ and substantially no expression in other storage organs is referred to as organ-specific expression; i.e., a ratio of expression products in a storage organ relative to another of about 100:1 or greater indicates organ specificity. Storage organ-specific promoters are thus members of the class of storage organ-enhanced promoters.

Exemplary plant storage organs include the roots of carrots, taro or manioc, potato tubers, and the meat of fruit such as red guava, passion fruit, mango, papaya, tomato, avocado, cherry, tangerine, mandarin, palm, melons such cantaloupe and watermelons and other fleshy fruits such as squash, cucumbers, mangos, apricots, peaches, as well as the seeds of maize (corn), soybeans, rice, oil seed rape and the like.

The CaMV 35S promoter is normally deemed to be a constitutive promoter. However, recent research has shown that a 21-bp region of the CaMV 35S promoter, when operatively linked into another, heterologous usual green tissue promoter, the rbcS-3A promoter, can cause the resulting chimeric promoter to become a root-enhanced promoter. That 21-bp sequence is disclosed in U.S. Pat. No. 5,023,179. The chimeric rbcS-3A promoter containing the 21-bp insert of U.S. Pat. No. 5,023,179 is a useful root-enhanced promoter herein.

A similar root-enhanced promoter, that includes the above 21-bp segment is the −90 to +8 region of the CAMV 35S promoter itself. U.S. Pat. No. 5,110,732 discloses that that truncated CaMV 35S promoter provides enhanced expression in roots and the radical of seed, a tissue destined to become a root. That promoter is also useful herein.

Another useful root-enhanced promoter is the −1616 to −1 promoter of the oil seed rape (*Brassica napus L.*) gene disclosed in PCT/GB92/00416 (WO 91/13922 published Sep. 19, 1991). *E. coli* DH5.alpha. harboring plasmid pRlambdaS4 and bacteriophage lambda.beta.1 that contain this promoter were deposited at the National Collection of Industrial and Marine Bacteria, Aberdeen, GB on Mar. 8, 1990 and have accession numbers NCIMB40265 and NCIMB40266. A useful portion of this promoter can be obtained as a 1.0 kb fragment by cleavage of the plasmid with HaeIII.

A preferred root-enhanced promoter is the mannopine synthase (mas) promoter present in plasmid pKan2 described by DiRita and Gelvin (1987) *Mol. Gen. Genet*, 207:233–241. This promoter is removable from its plasmid pKan2 as a XbaI-XbalI fragment.

The preferred mannopine synthase root-enhanced promoter is comprised of the core mannopine synthase (mas) promoter region up to position −138 and the mannopine synthase activator from −318 to −213, and is collectively referred to as AmasPmas. This promoter has been found to increase production in tobacco roots about 10- to about 100-fold compared to leaf expression levels.

Another root specific promoter is the about 500 bp 5' flanking sequence accompanying the hydroxyproline-rich glycopeprotein gene, HRGPnt3, expressed during lateral root initiation and reported by Keller et al. (1989) *Genes Dev.*, 3:1639–1646. Another preferred root-specific promoter is present in the about −636 to −1 5' flanking region of the tobacco root-specific gene ToRBF reported by Yamamoto et al. (1991) *Plant Cell*, 3:371–381. The cis-acting elements regulating expression are more specifically located by those authors in the region from about −636 to about −299 5' from the transcription initiation site. Yamamoto et al. reported steady state mRNA production from the ToRBF gene in roots, but not in leaves, shoot meristems or stems.

Still another useful storage organ-specific promoter are the 5' and 3' flanking regions of the fruit-ripening gene E8 of the tomato, *Lycopersicon esculentum*. These regions and their cDNA sequences are illustrated and discussed in Deikman et al. (1988) *EMBO J.*, 7(11):3315–3320 and (1992) *Plant Physiol.*, 100:2013–2017.

Three regions are located in the 2181 bp of the 5' flanking sequence of the gene and a 522 bp sequence 3' to the poly (A) addition site appeared to control expression of the E8 gene. One region from −2181 to −1088 is required for activation of E8 gene transcription in unripe fruit by ethylene and also contributes to transcription during ripening. Two further regions, −1088 to −863 and −409 to −263, are unable to confer ethylene responsiveness in unripe fruit but are sufficient for E8 gene expression during ripening.

The maize sucrose synthase-1 (Sh) promoter that in corn expresses its controlled enzyme at high levels in endosperm, at much reduced levels in roots and not in green tissues or pollen has been reported to express a chimeric reporter gene, β-glucuronidase (GUS), specifically in tobacco phloem cells that are abundant in stems and roots. Yang et al. (1990) *Proc. Natl. Acad. Sci., U.S.A.*, 87:4144–4148. This promoter is thus useful for plant organs such as fleshy fruits like melons, e.g. cantaloupe, or seeds that contain endosperm and for roots that have high levels of phloem cells.

Another exemplary tissue-specific promoter is the lectin promoter, which is specific for seed tissue. The lectin protein in soybean seeds is encoded by a single gene (Le1) that is only expressed during seed maturation and accounts for about 2 to about 5 percent of total seed mRNA. The lectin gene and seed-specific promoter have been fully characterized and used to direct seed specific expression in transgenic tobacco plants. See, e.g., Vodkin et al. (1983) *Cell*, 34:1023 and Lindstrom et al. (1990) *Developmental Genetics*, 11:160.

A particularly preferred tuber-specific expression promoter is the 5' flanking region of the potato patatin gene. Use of this promoter is described in Twell et al. (1987) *Plant Mol. Biol.,* 9:365–375. This promoter is present in an about 406 bp fragment of bacteriophage LPOTI. The LPOTI promoter has regions of over 90 percent homology with four other patatin promoters and about 95 percent homology over all 400 bases with patatin promoter PGT5. Each of these promoters is useful herein. See, also, Wenzler et al. (1989) *Plant Mol. Biol.*, 12:41–50.

Still further organ-enhanced and organ-specific promoter are disclosed in Benfey et al. (1988) *Science*, 244:174–181.

Each of the promoter sequences utilized is substantially unaffected by the amount of chimer molecule or particles in the cell. As used herein, the term "substantially unaffected" means that the promoter is not responsive to direct feedback control (inhibition) by the chimer molecules or particles accumulated in transformed cells or transgenic plant.

Transfection of plant cells using *Agrobacterium tumefaciens* is typically best carried out on dicotyledonous plants. Monocots are usually most readily transformed by so-called direct gene transfer of protoplasts. Direct gene transfer is usually carried out by electroportation, by polyethyleneglycol-mediated transfer or bombardment of cells by microprojectiles carrying the needed DNA. These methods of transfection are well-known in the art and need not be further discussed herein. Methods of regenerating whole plants from transfected cells and protoplasts are also well-known, as are techniques for obtaining a desired protein from plant tissues. See, also, U.S. Pat. Nos. 5,618,988 and 5,679,880 and the citations therein.

A transgenic plant formed using Agrobacterium transformation, electroportation or other methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous chimer molecule-encoding gene segregates independently during mitosis and meiosis. A transgenic plant containing an organ-enhanced promoter driving a single structural gene that encodes a contemplated HBc chimeric molecule; i.e., an independent segregant, is a preferred transgenic plant.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced chimer particle accumulation relative to a control (native, non-transgenic) or an independent segregant transgenic plant. A homozygous transgenic plant exhibits enhanced chimer particle accumulation as compared to both a native, non-transgenic plant and an independent segregant transgenic plant.

It is to be understood that two different transgenic plants can also be mated to produce offspring that contain two independently segregating added, exogenous (heterologous) genes. Selfing of appropriate progeny can produce plants that are homozygous for both added, exogenous genes that encode a chimeric HBc molecule. Back-crossing to a parental plant and out-crossing with a non-transgenic plant are also contemplated.

A transgenic plant of this invention thus has a heterologous structural gene that encodes a contemplated chimeric HBc molecule. A preferred transgenic plant is an independent segregant for the added heterologous chimeric HBc structural gene and can transmit that gene to its progeny. A more preferred transgenic plant is homozygous for the heterologous gene, and transmits that gene to all of its offspring on sexual mating.

Inasmuch as a gene that encodes a chimeric HBc molecule does not occur naturally in plants, a contemplated transgenic plant accumulates chimeric HBc molecule particles in a greater amount than does a non-transformed plant of the same type or strain when both plants are grown under the same conditions.

The phrase "same type" or "same strain" is used herein to mean a plant of the same cross as or a clone of the untransformed plant. Where alleic variations among siblings of a cross are small, as with extensively inbred plant, comparisons between siblings can be used or an average arrived at using several siblings. Otherwise, clones are preferred for the comparison.

Seed from a transgenic plant is grown in the field greenhouse, window sill or the like, and resulting sexually mature transgenic plants are self-pollinated to generate true breeding plants. The progeny from these plants become true breeding lines that are evaluated for chimeric HBc molecule particle accumulation, preferably in the field, under a range of environmental conditions.

A transgenic plant homozygous for chimeric HBc molecule particle accumulation is crossed with a parent plant having other desired traits. The progeny, which are heterozygous or independently segregatable for chimeric HBc molecule particle accumulation, are backcrossed with one or the other parent to obtain transgenic plants that exhibit chimeric HBc molecule particle accumulation and the other desired traits. The backcrossing of progeny with the parent may have to be repeated more than once to obtain a transgenic plant that possesses a number of desirable traits.

An insect cell system can also be used to express a HBc chimer. For example, in one such system *Autographa californica* nuclear polyhedrosis virus (AcNPV) or baculovirus is used as a vector to express foreign genes in *Spodoptera frugiperda* cells or in Trichoplusia larvae.

The sequences encoding a chimer can be cloned into a non-essential region of the virus, such as the polyhedrin gene, and placed under control of the polyhedrin promoter. Successful insertion of chimer sequence renders the polyhedrin gene inactive and produces recombinant virus lacking coat protein. The recombinant viruses can then be used to infect, for example, *S. Frugiperda* cells or *Trichoplusia* larvae in which the HBc chimer can be expressed. E. Engelhard et al. (1994) *Proc. Natl. Acad. Sci., USA*, 91:3224–3227; and V. Luckow, Insect Cell Expression Technology, pp. 183–218, in *Protein Engineering: Principles and Practice*, J. L. Cleland et al. eds., Wiley-Liss, Inc, 1996). Heterologous genes placed under the control of the polyhedrin promoter of the *Autographa californica* nuclear polyhedrosis virus (AcNPV) are often expressed at high levels during the late stages of infection.

Recombinant baculoviruses containing the chimeric gene are constructed using the baculovirus shuttle vector system (Luckow et al. (1993) *J. Virol.*, 67:4566–4579], sold commercially as the Bac-To-Bac™ baculovirus expression system (Life Technologies). Stocks of recombinant viruses are prepared and expression of the recombinant protein is monitored by standard protocols (O'Reilly et al., *Baculovirus Expression Vectors: A Laboratory Manual*, W. H. Freeman and Company, New York, 1992; and King et al., *The Baculovirus Expression System: A Laboratory Guide*, Chapman & Hall, London, 1992).

A variety of methods have been developed to operatively link DNA to vectors via complementary cohesive termini or blunt ends. For instance, complementary homopolymer tracts can be added to the DNA segment to be inserted into the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector, as noted before. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase.

Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass. A desired DNA segment can also be obtained using PCR technology in which the forward and reverse primers contain desired restriction sites that can be cut after amplification so that the gene can be inserted into the vector. Alternatively PCR products can be directly cloned into vectors containing T-overhangs (Promega Corp., A3600, Madison, Wis.) as is well known in the art.

The expressed chimeric protein self-assembles into particles within the host cells, whether in single cells or in cells within a multicelled host. The particle-containing cells are harvested using standard procedures, and the cells are lysed using a French pressure cell, lysozyme, sonicator, bead beater or a microfluidizer (Microfluidics International Corp., Newton Mass.). After clarification of the lysate, particles are precipitated with 45% ammonium sulfate, resuspended in 20 mM sodium phosphate, pH 6.8 and dialyzed against the same buffer. The dialyzed material is clarified by brief centrifugation and the supernatant subjected to gel filtration chromatography using Sepharose® CL-4B. Particle-containing fractions are identified, subjected to hydroxyapatite chromatography, and reprecipitated with ammonium sulfate prior to resuspension, dialysis and sterile filtration and storage at −70° C.

Malarial Inocula and Vaccines

A before-described recombinant HBc chimer immunogen preferably in particulate form is dissolved or dispersed in an immunogenic effective amount in a pharmaceutically acceptable vehicle composition that is preferably aqueous to form an inoculum or vaccine. When administered to a host animal in need of immunization or in which antibodies are desired to be induced such as a mammal (e.g., a mouse, dog, goat, sheep, horse, bovine, monkey, ape, or human) or bird (e.g., a chicken, turkey, duck or goose), an inoculum induces antibodies that immunoreact with the malarial B cell epitope present in the immunogen. In a vaccine, those induced antibodies also immunoreact in vivo with (bind to) the sporozoite and protect the mammal from malarial infection by the Plasmodium species whose B cell epitope was present in the immunogen. A composition that is an inoculum in one animal can be a vaccine for another where the *Plasmodium* species against which antibodies are raised does not infect the animal inoculated, as where an inoculum against *P. falciparum* is used to raise antibodies in mice.

The amount of recombinant HBc chimer immunogen utilized in each immunization is referred to as an immunogenic effective amount and can vary widely, depending inter alia, upon the recombinant HBc chimer immunogen, mammal immunized, and the presence of an adjuvant in the vaccine, as discussed below. Immunogenic effective amounts for a vaccine and an inoculum provide the protection or antibody activity, respectively, discussed hereinbefore.

Vaccines or inocula typically contain a recombinant HBc chimer immunogen concentration of about 1 microgram to about 1 milligram per inoculation (unit dose), and preferably about 10 micrograms to about 50 micrograms per unit dose. Immunizations in mice typically contain 10 or 20 µg of chimer particles.

The term "unit dose" as it pertains to a vaccine or inoculum of the present invention refers to a physically discrete unit suitable as an unitary dosage for animals, each unit containing a predetermined quantity of active material calculated to individually or collectively produce the desired immunogenic effect in association with the required diluent; i.e., carrier, or vehicle. A single unit dose or a plurality of unit doses can be used to provide an immunogenic effective amount of recombinant HBc chimer immunogen.

Vaccines or inocula are typically prepared from a recovered recombinant HBc chimer immunogen by dispersing the immunogen in a physiologically tolerable (acceptable) diluent vehicle such as water, saline phosphate-buffered saline (PBS), acetate-buffered saline (ABS), Ringer's solution or the like to form an aqueous composition. The diluent vehicle can also include oleaginous materials such as peanut oil, squalane or squalene as is discussed hereinafter.

The immunogenic active ingredient is often mixed with excipients that are pharmaceutically acceptable and compatible with the active ingredient. Suitable excipients are, for example, water, saline, dextrose, glycerol, ethanol, or the like and combinations thereof. In addition, if desired, an inoculum or vaccine can contain minor amounts of auxiliary substances such as wetting or emulsifying agents, pH buffering agents that enhance the immunogenic effectiveness of the composition.

A contemplated vaccine or inoculum advantageously also includes an adjuvant. Suitable adjuvants for vaccines and inocula of the present invention comprise those adjuvants that are capable of enhancing the antibody responses against B cell epitopes of the chimer, as well as adjuvants capable of enhancing cell mediated responses towards T cell epitopes contained in the chimer. Adjuvants are well known in the art (see, for example, *Vaccine Design-The Subunit and Adjuvant Approach*, 1995, Pharmaceutical Biotechnology, Volume 6, Eds. Powell, M. F., and Newman, M. J., Plenum Press, New York and London, ISBN 0-306-44867-X).

Exemplary adjuvants include complete Freund's adjuvant (CFA) that is not used in humans, incomplete Freund's adjuvant (IFA), squalene, squalane and alum [e.g., Alhydrogel™ (Superfos, Denmark)], which are materials well known in the art, and are available commercially from several sources.

Preferred adjuvants for use with immunogens of the present invention include aluminum or calcium salts (for example hydroxide or phosphate salts). A particularly preferred adjuvant for use herein is an aluminum hydroxide gel such as Alhydrogel™. For aluminum hydroxide gels (alum), the chimer protein is admixed with the adjuvant so that between 50 to 800 micrograms of aluminum are present per dose, and preferably between 400 and 600 micrograms are present.

Another particularly preferred adjuvant for use with an immunogen of the present invention is an emulsion. A contemplated emulsion can be an oil-in-water emulsion or a water-in-oil emulsions. In addition to the immunogenic chimer protein, such emulsions comprise an oil phase of squalene, squalane, peanut oil or the like as are well-known, and a dispersing agent. Non-ionic dispersing agents are preferred and such materials include mono- and di-$C_{12}$-$C_{24}$-fatty acid esters of sorbitan and mannide such as sorbitan mono-stearate, sorbitan mono-oleate and mannide mono-oleate. An immunogen-containing emulsion is administered as an emulsion.

Preferably, such emulsions are water-in-oil emulsions that comprise squalene and mannide mono-oleate (Arlacel™ A), optionally with squalane, emulsified with the chimer protein in an aqueous phase. Well-known examples of such emulsions include Montanide™ ISA-720, and Montanide™ ISA 703 (Seppic, Castres, France), each of which is understood to contain both squalene and squalane, with squalene predominating in each, but to a lesser extent in Montanide™ ISA 703. Most preferably, Montanide™ ISA-720 is used, and a ratio of oil-to-water of 7:3 (w/w) is used. Other preferred oil-in-water emulsion adjuvants include those disclosed in WO 95/17210 and EP 0 399 843.

The use of small molecule adjuvants is also contemplated herein. One type of small molecule adjuvant useful herein is a 7-substituted-8-oxo- or 8-sulfo-guanosine derivative described in U.S. Pat. Nos. 4,539,205, 4,643,992, 5,011,828 and 5,093,318, whose disclosures are incorporated by reference. Of these materials, 7-allyl-8-oxoguanosine (loxoribine) is particularly preferred. That molecule has been shown to be particularly effective in inducing an antigen-(immunogen-)specific response.

Still further useful adjuvants include monophosphoryl lipid A (MPL) available from Corixa Corp. (see, U.S. Pat. No. 4,987,237), CPG available from Coley Pharmaceutical Group, QS21 available from Aquila Biopharmaceuticals, Inc., SBAS2 available from SKB, the so-called muramyl dipeptide analogues described in U.S. Pat. No. 4,767,842, and MF59 available from Chiron Corp. (see, U.S. Pat. Nos. 5,709,879 and 6,086,901).

More particularly, immunologically active saponin fractions having adjuvant activity derived from the bark of the South American tree *Quillaja Saponaria Molina* (e.g. Quil™ A) are also useful. Derivatives of Quil™ A, for example QS21 (an HPLC purified fraction derivative of Quil™ A), and the method of its production is disclosed in U.S. Pat. No. 5,057,540. In addition to QS21 (known as QA21), other fractions such as QA17 are also disclosed.

3-De-O-acylated monophosphoryl lipid A is a well-known adjuvant manufactured by Ribi Immunochem, Hamilton, Mont. The adjuvant contains three components extracted from bacteria, monophosphoryl lipid (MPL) A, trehalose dimycolate (TDM) and cell wall skeleton (CWS) (MPL+TDM+CWS) in a 2% squalene/Tween™ 80 emulsion. This adjuvant can be prepared by the methods taught in GB 2122204B. A preferred form of 3-de-O-acylated monophosphoryl lipid A is in the form of an emulsion having a small particle size less than 0.2 μm in diameter (EP 0 689 454 B1).

The muramyl dipeptide adjuvants include N-acetyl-muramyl-L-threonyl-D-isoglutamine(thur-MDP), N-acetyl-nor-muramyl-L-alanyl-D-isoglutamine (CGP 11637, referred to as nor-MDP), and N-acetylmuramyl-L-alanyl-D-isoglutaminyl-L-alanine-2-(1'-2'-dipalmityol-sn-glycero-3-hydroxyphosphoryloxy)-ethylamin (CGP) 1983A, referred to as MTP-PE).

Preferred adjuvant mixtures include combinations of 3D-MPL and QS21 (EP 0 671 948 B1), oil-in-water emulsions comprising 3D-MPL and QS21 (WO 95/17210, PCT/EP98/05714), 3D-MPL formulated with other carriers (EP 0 689 454 B1), QS21 formulated in cholesterol-containing liposomes (WO 96/33739), or immunostimulatory oligonucleotides (WO 96/02555). Alternative adjuvants include those described in WO 99/52549 and non-particulate suspensions of polyoxyethylene ether (UK Patent Application No. 9807805.8).

Adjuvants are utilized in an adjuvant amount, which can vary with the adjuvant, mammal and recombinant HBc chimer immunogen. Typical amounts can vary from about 1 μg to about 1 mg per immunization. Those skilled in the art know that appropriate concentrations or amounts can be readily determined.

Inocula and vaccines are conventionally administered parenterally, by injection, for example, either subcutaneously or intramuscularly. Additional formulations that are suitable for other modes of administration include suppositories and, in some cases, oral formulation or by nasal spray. For suppositories, traditional binders and carriers can include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like.

An inoculum or vaccine composition takes the form of a solution, suspension, tablet, pill, capsule, sustained release formulation or powder, and contains an immunogenic effective amount of HBc chimer, preferably as particles, as active ingredient. In a typical composition, an immunogenic effective amount of preferred HBc chimer particles is about 1 μg to about 1 mg of active ingredient per dose, and more preferably about 5 μg to about 50 μg per dose, as noted before.

A vaccine or inoculum is typically formulated for parenteral administration. Exemplary immunizations are carried out sub-cutaneously (SC) intra-muscularly (IM), intravenusly (IV), intraperitoneally (IP) or intra-dermally (ID).

The HBc chimer particles and HBc chimer particle conjugates can be formulated into the vaccine as neutral or salt forms. Pharmaceutically acceptable salts, include the acid addition salts (formed with the free amino groups of the protein or hapten) and are formed with inorganic acids such as, for example, hydrochloric or phosphoric acids, or such organic acids as acetic, oxalic, tartaric, mandelic, and the like. Salts formed with the free carboxyl groups can also be derived form inorganic bases such as, for example, sodium, potassium, ammonium, calcium, or ferric hydroxides, and such organic bases as isopropylamine, trimethylamine, 2-ethylamino ethanol, histidine, procaine, and the like.

The inocula or vaccines are administered in a manner compatible with the dosage formulation, and in such amount as are therapeutically effective and immunogenic. The quantity to be administered depends on the subject to be treated, capacity of the subject's immune system to synthesize antibodies, and degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in intervals (weeks or months) by a subsequent injection or other administration.

Once immunized, the mammal is maintained for a period of time sufficient for the recombinant HBc chimer immunogen to induce the production of a sufficient titer of antibodies that bind to sporozoite. The maintenance time for the production of anti-sporozoite antibodies typically lasts for a period of about three to about twelve weeks, and can include a booster, second immunizing administration of the vaccine. A third immunization is also contemplated, if desired, at a time 24 weeks to five years after the first immunization. It is particularly contemplated that once a protective level titer of anti-sporozoite antibodies is attained, that the vaccinated mammal is preferably maintained at or near that antibody titer by periodic booster immunizations administered at intervals of about 1 to about 5 years.

The production of anti-sporozoite antibodies is readily ascertained by obtaining a plasma or serum sample from the immunized mammal and assaying the antibodies therein for their ability to bind to a synthetic circumsporozoite immunodominant antigen [e.g. the P. falciparum CS protein peptide (NANP)$_5$ used herein] in an ELISA assay as described hereinafter or by another immunoassay such as a Western blot as is well known in the art. Most preferable is the use of the indirect immunofluorescence assay (IFA), in which intact sporozoites are employed as the capture antigen, discussed hereinafter.

It is noted that the before-described anti-CS antibodies so induced can be isolated from the blood of the host mammal using well known techniques, and then reconstituted into a second vaccine for passive immunization as is also well known. Similar techniques are used for gamma-globulin immunizations of humans. For example, antiserum from one or a number of immunized hosts can be precipitated in aqueous ammonium sulfate (typically at 40–50 percent of saturation), and the precipitated antibodies purified chromatographically as by use of affinity chromatography in which (NANP)$_5$ is utilized as the antigen immobilized on the chromatographic column.

Inocula are preparations that are substantially identical to vaccines, but are used in a host mammal in which antibodies to malaria are desired to be induced, but in which protection from malaria is not desired. In one example, a vaccine against P. falciparum of P. vivax can be used in mice as an inoculum to induce antibody production and not be a vaccine because neither malarial species can infect mice. Similarly, a similar inoculum can be used in a horse or sheep to induce antibody production against either or both malarial species for use in a passive immunization in yet another animal such as humans.

Best Mode for Carrying Out the Invention

Without further elaboration, it is believed that one skilled in the art can, using the preceding description and the detailed examples below, utilize the present invention to its fullest extent. The following preferred specific embodiments are, therefore, to be construed as merely illustrative, and not limiting of the remainder of the disclosure in any way whatsoever.

EXAMPLE 1

B Cell Epitope-Containing

Chimer Preparation

A. Preparation of plasmid vector pKK223-3N, a modified form of pKK223-3

Plasmid vector pKK223-3 (Pharmacia) was modified by the establishment of a unique NcoI restriction site to enable insertion of HBc genes as NcoI-HindIII restriction fragments and subsequent expression in E. coli host cells. To modify the pKK223-3 plasmid vector, a new SphI-HindIII fragment was prepared using the PCR primers pKK223-3/433-452-F and pKK223-NcoI-mod-R, and pKK223-3 as the template.

This PCR fragment was cut with the restriction enzymes SphI and HindIII to provide a 467 bp fragment that was then ligated with a 4106 bp fragment of the pKK223-3 vector, to effectively replace the original 480 bp SphI-HindIII fragment. The resultant plasmid (pKK223-3N) is therefore 13 bp shorter than the parent plasmid and contains modified nucleotide sequence upstream of the introduced NcoI site (see FIG. 1 in which the dashes indicate the absent bases). The final plasmid, pKK223-3N, has a size of 4573 bp. Restriction sites in plasmid pKK223-3N are indicated in FIG. 1, and the nucleotide changes made to pKK223-3 to form plasmid pKK223-3N are indicated by an underline as shown below.

pKK223-3/433-452-F
GGTGCATGCAAGGAGATG                                    SEQ ID NO:27 pKK223-NcoI-mod-R
GCGAAGCTTCGGATCccatggTTTTTTCCTCCTTATGTGAAATTGTTATCCGCTC   SEQ ID NO:28

B. Preparation of V1 and V2 Cloning Vectors

Modified HBc149 genes, able to accept the directional insertion of synthetic dsDNA fragments into the immunodominant loop region, were constructed using PCR. (The plasmid accepting inserts between amino acids E77 and D78 was named V1, whereas the plasmid accepting inserts between D78 and P79 was named V2.) The HBc149 gene was amplified in two halves using two PCR primer pairs, one of which amplifies the amino terminus, the other amplifies the carboxyl terminus. For V1, the products of the PCR reactions (N- and C-terminus) are both 246 bp fragments; for V2, the products are a 249 bp (N-terminus) and a 243 bp fragment (C-terminus).

The N-terminal fragments prepared were digested with NcoI and EcoRI, and the C-terminal fragments were digested with EcoRI and HindIII. The V1 and V2 fragments pairs were then ligated together at the common EcoRI overhangs. The resultant NcoI-HindIII fragments were then ligated into the pKK223-3N vector, which had been prepared by digestion with NcoI and HindIII.

To insert B cell epitopes into the V1 and V2 plasmids, the plasmids were digested with EcoRI and SacI restriction enzymes. Synthetic dsDNA fragments containing 5' EcoRI and 3' SacI overhangs were then inserted. In both cases, V1 and V2, glycine-isoleucine (EcoRI) and glutamic acid-leucine (SacI) amino acid pairs, coded for by the restriction sites, flank the inserted B cell epitopes. The inserted restriction sites are underlined in the primers below.

V1
HBc149/NcoI-F
5'-TTGGGCCATGGACATCGACCCTTA                        SEQ ID NO:29

HBc-E77/EcoRI-R
5'-GCGGAATTCCTTCCAAATTAACACCCACC                   SEQ ID NO:30

HBc-D78/EcoRI-SacI-F
5'-CGCGAATTCAAAAAGAGCTCGATCCAGCGTCTAGAGAC          SEQ ID NO:31

HBc149/HindIII-R
5'-CGCAAGCTTAAACAACAGTAGTCTCCGGAAG                 SEQ ID NO:32

V2
HBc149/NcoI-F
5'-TTGGGCCATGGACATCGACCCTTA                        SEQ ID NO:29

HBc-D78/EcoRI-R
5'-GCGGAATTCCATCTTCCAAATTAACACCCAC                 SEQ ID NO:186

HBc-P79/EcoRI-SacI-F
5'-CGCGAATTCAAAAAGAGCTCCCAGCGTCTAGAGACCTAG         SEQ ID NO:34

HBc149/HindIII-R
5'-CGCAAGCTTAAACAACAGTAGTCTCCGGAAG                 SEQ ID NO:32

C. Preparation of V7 Cloning Vector

To enable the fusion of T cell epitopes to the C terminus of a HBc chimer, a new vector, V7, was constructed. Unique EcoRI and SacI restriction sites were inserted between valine-149 and the HindIII site to facilitate directional insertion of synthetic dsDNAs into EcoRI-HindIII (or EcoRI-SacI) restriction sites. The pair of PCR primers below was used to amplify the HBc 149 gene with a NcoI restriction site at the amino-terminus and EcoRI, SacI and HindIII sites at the carboxyl-terminus. The product of the PCR reaction (479 bp) was digested with NcoI/HindIII and cloned into pKK223-3N to form V7.

To insert T cell epitopes, the plasmid (V7) was digested EcoRI/HindIII (or EcoRI-SacI) and synthetic dsDNA fragments having EcoRI/HindIII (or EcoRI/SacI) overhangs, were ligated into V7. For all V7 constructs, the final amino acid of native HBc (valine-149) and the first amino acid of the inserted T cell epitope are separated by a glycine-isoleucine dipeptide sequence coded for by the nucleotides that form the EcoRI restriction site. For epitopes inserted at EcoRI/SacI, there are additional glutamic acid-leucine residues after the T cell epitope, prior to the termination codon, contributed by the SacI site. Restriction sites are again underlined in the primers shown.

HBc149/NcoI-F                                      SEQ ID NO:29
5'-TTGGGCCATGGACATCGACCCTTA

HBc149/SacI-EcoRI-H3-R                             SEQ ID NO:33
5'-CGCAAGCTTAGAGCTCTTGAATTCCAACAACAGTAGTCTCCG

D. Preparation of V12 Expression Constructs

V12 vectors, which contain B cell epitopes between amino acids 78 and 79, as well as T cell epitopes downstream of valine-149, were constructed from V2 and V7 vectors. The carboxyl terminus of a V7 vector containing a T cell epitope inserted at EcoRI/HindIII was amplified using two PCR primers (HBc-P79/SacI-F and pKK223-2/4515-32R) to provide a dsDNA fragment corresponding to amino acids 79–149 plus the T cell epitope, flanked with SacI and HindIII restriction sites.

The PCR products were cut with SacI and HindIII and then cloned into the desired V2 vector prepared by cutting with the same two enzymes. The PCR primers shown are amenable for the amplification of the carboxyl terminus of all V7 genes, irrespective of the T cell epitope present after amino acid 149 of the HBc gene.

One exception to the generality of this approach was in the preparation of the V12 constructs containing the Pf-CS (C17A) mutation, which were prepared from existing V12 constructs. In this case, V12 constructs were amplified with HBc149/NcoI-F (SEQ ID NO:29) and the mis-match reverse PCR primer (SEQ ID NO: 104), which facilitated the C17A mutation. The resultant PCR product was digested with NcoI and HindIII and cloned back into pKK223-3N (previously cut with the same enzymes). Restriction sites are underlined.

HBc-P79/SacI-F
5'-CGCGAGCTCCCAGCGTCTAGAGACCTAG     SEQ ID NO:35 pKK223-2/4515-32R
5'-GTATCAGGCTGAAAATC                SEQ ID NO:36

E. P. falciparum CS-repeat B cell Epitopes Inserted into V2

For V2 and V7 constructs, synthetic dsDNA fragments coding for the B (V2) or T cell epitope (V7) of interest were inserted into EcoRI/SacI restriction sites. Synthetic dsDNA fragments, encoding B and T cell epitopes of interest, were prepared by mixing complementary single stranded DNA oligonucleotides at equimolar concentrations, heating to 95° C for 5 minutes, and then cooling to room temperature at a rate of −1° C. per minute. This annealing reaction was performed in TE buffer. The double-stranded DNAs are shown below with the encoded epitope sequence shown above. The pound symbol, #, is used in some of the amino acid residue sequences that follow to indicate the presence of a stop codon.

```
Pf1
  I  N  A  N  P  N  A  N  P  N  A  N  P  N  A
AATTAACGCTAATCCGAACGCTAATCCGAACGCTAATCCGAACGCTA
    TTGCGATTAGGCTTGCGATTAGGCTTGCGATTAGGCTTGCGAT

N  P  E  L                                  SEQ ID NO:37
ATCCGGAGCT                                  SEQ ID NO:38
    TAGGCC                                  SEQ ID NO:39

Pf3
  I  N  A  N  P  N  V  D  P  N  A  N  P  N  A  N  P
AATTAACGCTAATCCGAACGTTGACCCGAACGCTAATCCGAACGCTAATCCGA
    TTGCGATTAGGCTTGCAACTGGGCTTGCGATTAGGCTTGCGATTAGGCT

N  A  N  P  N  V  D  P  N  A  N  P  E  L   SEQ ID NO:40
ACGCTAATCCGAACGTTGACCCGAACGCTAATCCGGAGCT    SEQ ID NO:41
TGCGATTAGGCTTGCAACTGGGCTTGCGATTAGGCCTCGAGG  SEQ ID NO:42

Pf3.1
  I  N  A  N  P  N  V  D  P  N  A  N     P  N  A  N  P
AATTAACGCGAATCCGAACGTGGATCCGAATGCCAACCCTAACGCCAACCC
TTGCGCTTAGGCTTGCACCTAGGCTTACGGTTGGGATTGCGGTTGGG

N  A  N  P  E  L                            SEQ ID NO:43
AAATGCGAACCCAGAGCT                          SEQ ID NO:44
TTTACGCTTGGGTC                              SEQ ID NO:45

Pf3.2
  I  N  A  N  P  N  A  N  P  N  A  N  P  N  V  D  P
AATTAACGCGAATCCGAATGCCAACCCTAACGCCAACCCAAACGTGGATCCGA
    TTGCGCTTAGGCTTACGGTTGGGATTGCGGTTGGGTTTGCACCTAGGCT

N  A  N  P  E  L                            SEQ ID NO:46
ATGCGAACCCAGAGCT                            SEQ ID NO:47
    TACGCTTGGGTC                            SEQ ID NO:48

Pf3.3
  I  N  A  N  P  N  V  D  P  N  A  N  P  N  A  N  P
AATTAACGCGAATCCGAACGTGGATCCAAATGCCAACCCTAACGCTAATCCAA
TTGCGCTTAGGCTTGCACCTAGGTTTACGGTTGGGATTGCGATTAGGTT

N  A  N  P  N  V  D  P  N  A  N  P  E  L   SEQ ID NO:49
ACGCCAACCCGAATGTTGACCCCAATGCCAATCCGGAGCT    SEQ ID NO:50
TGCGGTTGGGCTTACAACTGGGGTTACGGTTAGGCC        SEQ ID NO:51

Pf3.4
  I  N  P  N  V  D  P  N  A  N  P  N  A  N  P  N  A
AATTAATCCGAACGTGGATCCAAATGCCAACCCTAACGCTAATCCAAACGCCA
    TTAGGCTTGCACCTAGGTTTACGGTTGGGATTGCGATTAGGTTTGCGGT

N  P  N  V  E  L                            SEQ ID NO:52
ACCCGAATGTTGAGCT                            SEQ ID NO:53
TGGGCTTACAAC                                SEQ ID NO:54

Pf3.5
  I  N  P  N  V  D  P  N  A  N  P  N  A  N  P  N  A
AATTAATCCGAACGTGGATCCAAATGCCAACCCTAACGCTAATCCAAACGCCA
    TTAGGCTTGCACCTAGGTTTACGGTTGGGATTGCGATTAGGTTTGCGGT

N  P  N  V  D  P  E  L                      SEQ ID NO:55
ACCCGAATGTTGACCCTGAGCT                      SEQ ID NO:56
TGGGCTTACAACTGGGAC                          SEQ ID NO:57

Pf3.6
  I  N  P  N  V  D  P  N  A  N  P  N  A  N  P  N  A
AATTAATCCGAACGTGGATCCAAATGCCAACCCTAACGCTAATCCAAACGCCA
    TTAGGCTTGCACCTAGGTTTACGGTTGGGATTGCGATTAGGTTTGCGGT

N  P  N  V  D  P  N  A  E  L                SEQ ID NO:53
ACCCGAATGTTGACCCTAATGCTGAGCT                SEQ ID NO:59
    TGGGCTTACAACTGGGATTACGAC                SEQ ID NO:60

Pf3.7
  I  N  V  D  P  N  A  N  P  N  A  N  P  N  A  N  P
AATTAACGTGGATCCAAATGCCAACCCTAACGCTAATCCAAACGCCAACCCGA
    TTGCACCTAGGTTTACGGTTGGGATTGCGATTAGGTTTGCGGTTGGGCT

N  V  E  L                                  SEQ ID NO:61
ATGTTGAGCT                                  SEQ ID NO:62
TACAAC                                      SEQ ID NO:63
```

```
Pf3.8
    I  N  V  D  P  N  A  N  P  N  A  N  P  N  A  N  P
  AATTAACGTGGATCCAAATGCCAACCCTAACGCTAATCCAAACGCCAACCCGA
      TTGCACCTAGGTTTACGGTTGGGATTGCGATTAGGTTTGCGGTTGGGCT

N  V  D  P  E  L                          SEQ ID NO:64
ATGTTGACCCTGAGCT                          SEQ ID NO:65
TACAACTGGGAC                              SEQ ID NO:66

Pf3.9
    I  N  V  D  P  N  A  N  P  N  A  N  P  N  A  N  P
  AATTAACGTGGATCCAAATGCCAACCCTAACGCTAATCCAAACGCCAACCCGA
      TTGCACCTAGGTTTACGGTTGGGATTGCGATTAGGTTTGCGGTTGGGCT

N  V  D  P  N  A  E  L                    SEQ ID NO:67
ATGTTGACCCTAATGCTGAGCT                    SEQ ID NO:68
TACAACTGGGATTACGAC                        SEQ ID NO:69

Pf3.10
    I  D  P  N  A  N  P  N  A  N  P  N  A  N  P
  AATTGATCCAAATGCCAACCCTAACGCTAATCCAAACGCCAACC
      CTAGGTTTACGGTTGGGATTGCGATTAGGTTTGCGGTTGG

N  V  E  L                                SEQ ID NO:70
CGAATGTTGAGCT                             SEQ ID NO:71
GCTTACAAC                                 SEQ ID NO:72

Pf3.11
    I  D  P  N  A  N  P  N  A  N  P  N  A  N  P  N  V
  AATTGATCCAAATGCCAACCCTAACGCTAATCCAAACGCCAACCCGAATGTTG
      CTAGGTTTACGGTTGGGATTGCGATTAGGTTTGCGGTTGGGCTTACAAC

D  P  E  L                                SEQ ID NO:73
ACCCTGAGCT                                SEQ ID NO:74
TGGGAC                                    SEQ ID NO:75

Pf3.12
    I  D  P  N  A  N  P  N  A  N  P  N  A  N  P  N  V
  AATTGATCCAAATGCCAACCCTAACGCTAATCCAAACGCCAACCCGAATGTTG
      CTAGGTTTACGGTTGGGATTGCGATTAGGTTTGCGGTTGGGCTTACAAC

D  P  N  A  E  L                          SEQ ID NO:76
ACCCTAATGCCGAGCT                          SEQ ID NO:77
TGGGATTACGGC                              SEQ ID NO:78

F. P. falciparum universal T cell epitope
Pf-UTC (PF/CS326-345)
    I  E  Y  L  N  K  I  Q  N  S  L  S  T  E  W  S  P
  AATTGAATATCTGAACAAAATCCAGAACTCTCTGTCCACCGAATGGTCTCCGT
      CTTATAGACTTGTTTTAGGTCTTGAGAGACAGGTGGCTTACCAGAGGCA C  S  V  T  #  #                          SEQ ID NO:79
GCTCCGTTACCTAGTA                          SEQ ID NO:80
CGAGGCAATGGATCATTCGA                      SEQ ID NO:81

P. vivax CS-repeat B cell epitopes
Pv-T1A
    I  P  A  G  D  R  A  D  G  Q  P  A  G  D  R  A  A
  AATTCCGGCTGGTGACCGTGCAGATGGCCAGCCAGCGGGTGACCGCGCTGCAG
      GGCCGACCACTGGCACGTCTACCGGTCGGTCGCCCACTGGCGCGACGTC G  Q  P  A  G  E  L                       SEQ ID NO:82
GCCAGCCGGCTGGCGAGCT                       SEQ ID NO:83
CGGTCGGCCGACCGC                           SEQ ID NO:84

Pv-T1B
    I  D  R  A  A  G  Q  P  A  G  D  R  A  D  G  Q  P
  AATTGACAGAGCAGCCGGACAACCAGCAGGCGATCGAGCAGACGGACAGCCCG
      CTGTCTCGTCGGCCTGTTGGTCGTCCGCTAGCTCGTCTGCCTGTCGGGC
```

-continued

```
A   G   E   L                                        SEQ ID NO:85
CAGGGGAGCT                                           SEQ ID NO:86
GTCCCC                                               SEQ ID NO:87

Pv-T2A
  I   A   N   G   A   G   N   Q   P   G   A   N   G   A   G   D   Q
AATTGCGAACGGCGCCGGTAATCAGCCGGGGGCAAACGGCGCGGGTGATCAAC
    CGCTTGCCGCGGCCATTAGTCGGCCCCCGTTTGCCGCGCCCACTAGTTG

P   G   E   L                                        SEQ ID NO:88
CAGGGGAGCT                                           SEQ ID NO:89
GTCCCC                                               SEQ ID NO:90

Pv-T2B
  I   A   N   G   A   D   N   Q   P   G   A   N   G   A   D   D   Q
AATTGCGAACGGCGCCGATAATCAGCCGGGTGCAAACGGGGCGGATGACCAAC
    CGCTTGCCGCGGCTATTAGTCGGCCCACGTTTGCCCCGCCTACTGGTTG

P   G   E   L                                        SEQ ID NO:91
CAGGCGAGCT                                           SEQ ID NO:92
GTCCGC                                               SEQ ID NO:93

Pv-T2C
  I   A   N   G   A   G   N   Q   P   G   A   N   G   A   G   D   Q
AATTGCGAACGGCGCCGGTAATCAGCCGGGAGCAAACGGCGCGGGGGATCAAC
    CGCTTGCCGCGGCCATTAGTCGGCCCTCGTTTGCCGCGCCCCCTAGTTG

P   G   A   N   G   A   D   N   Q   P   G   A   N   G   A   D   D
CAGGCGCCAATGGTGCAGACAACCAGCCTGGGGCGAATGGAGCCGATGACC
GTCCGCGGTTACCACGTCTGTTGGTCGGACCCCGCTTACCTCGGCTACTGG

Q   P   G   E   L                                    SEQ ID NO:94
AACCCGGCGAGCT                                        SEQ ID NO:95
TTGGGCCGC                                            SEQ ID NO:96

PV-T3
 I   A   P   G   A   N   Q   E   G   G   A   A   A   P   G   A   N
AATTGCGCCGGGCGCCAACCAGGAAGGTGGGGCTGCAGCGCCAGGAGCCAATC
    CGCGGCCCGCGGTTGGTCCTTCCACCCCGACGTCGCGGTCCTCGGTTAG

Q   E   G   G   A   A   E   L                        SEQ ID NO:97
AAGAAGGCGGTGCAGCGGAGCT                               SEQ ID NO:98
TTCTTCCGCCACGTCGCC                                   SEQ ID NO:99
```

EXAMPLE 2

*P. vivax* universal T cell epitope

```
Pv-UTC
 I   E   Y   L   D   K   V   R   A   T   V   G   T   E   W   T   P
AATTGAATATCTGGATAAAGTGCGTGCGACCGTTGGCACGGAATGGACTCCGT
    CTTATAGACCTATTTCACGCACGCTGGCAACCGTGCCTTACCTGAGGCA

C   S   V   T   #   #                               SEQ ID NO:100
GCAGCGTGACCTAATA                                     SEQ ID NO:101
CGTCGCACTGGATTATTCGA                                 SEQ ID NO:102

A. PCR primers for site-directed
   mutagenesis
Pf-CS(C17A)-R                                        SEQ ID NO:103

#   #   T   V   S   A   P   S   W   E   T   S
GCCAAGCTTACTAGGTAACGGAGGCCGGAGACCATTCGGTGG
    HindIII                                          SEQ ID NO:104
```

B. PCR Primers for Truncation and Cysteine Addition at C-terminus

To modify the C-terminus of HBc chimer genes, either via the addition of cysteine residues or varying the length of the HBc gene, PCR reactions were performed using HBc149 as template with the HBc/NcoI-F primer and a reverse primer (e.g. HBc149+C/HindIII-R) that directed the desired modification of the C-terminus. PCR products were digested with NcoI and HindIII (whose restriction sites are underlined), and cloned into pKK223-3N at the same restriction sites.

```
HBc149/NcoI-F                                    SEQ ID NO:105
         M   D   I   D   P   Y
5'-TTGGGCCATGGACATCGACCCTTA                      SEQ ID NO:29

HBc149+C/HindIII-R                               SEQ ID NO:106
         #   #   C   V   V   T   E   P   L
5'-CGCAAGCTTACTAGCAAACAACAGTAGTCTCCGGAAG         SEQ ID NO:107

HBc144/HindIII-R                                 SEQ ID NO:108
         #"P  L   T   S   L   I   P
CGCAAGCTTACGGAAGTGTTGATAGGATAGGG                 SEQ ID NO: 109

HBc142/HindIII-R                                 SEQ ID NO:110
         #"T  S   L   I   P   A   N   P
CGCAAGCTTATGTTGATAGGATAGGGGCATTTGG               SEQ ID NO: 111

HBc140/HindIII-R                                 SEQ ID NO:112
         #"L  I   P   A   N   P   P
CGCAAGCTTATAGGATAGGGGCATTTGGTGG                  SEQ ID NO: 113

HBc139/HindIII-R                                 SEQ ID NO:114
         #"I  P   A   N   P   P
GCGAAGCTTAGATAGGGGCATTTGGTGG                     SEQ ID NO:115

HBc138/HindIII-R                                 SEQ ID NO:116
         #"P  A   N   P   P   R
CGCAAGCTTAAGGGGCATTTGGTGGTCT                     SEQ ID NO: 117

HBc138+C/HindIII-R                               SEQ ID NO:118
         #"C  P   A   N   P   P   R
GCGAAGCTTAGCAAGGGGCATTTGGTGGTCT                  SEQ ID NO:119

HBc137/HindIII-R                                 SEQ ID NO:120
         #"A  N   P   P   R   Y   A
GCGAAGCTTAGGCATTTGGTGGTCTATAGC                   SEQ ID NO:121

HBc137+C/HindIII-R                               SEQ ID NO:122
         #"C  A   N   P   P   R   Y   A
GCGAAGCTTAGCAGGCATTTGGTGGTCTATAA                 SEQ ID NO: 123

HBc136/HindIII-R                                 SEQ ID NO:124
         #"N  P   P   R   Y   A   P
CGCAAGCTTAATTTGGTGGTCTATAAGCTGG                  SEQ ID NO:125
```

Example 3: Assay Procedures

EXAMPLE 3

Assay Procedures

A. Antigenicity

1. Particle ELISA

Purified particles were diluted to a concentration of 10 μg/mL in coating buffer (50 mM sodium bicarbonate, pH 9.6) and coated onto the wells of ELISA strips (50 μL/well). The ELISA strips were incubated at room temperature overnight (about 18 hours). Next morning, the wells were washed with ELISA wash buffer [phosphate buffered saline (PBS), pH 7.4, 0.05% Tween®-20] and blocked with 3% BSA in PBS for 1 hour (75 μL/well). ELISA strips were stored, dry, at −20° C. until needed.

To determine the antigenicity of particles, antisera were diluted using 1% BSA in PBS and 50 μL/well added to antigen-coated ELISA wells. Sera were incubated for 1 hour, washed with ELISA wash buffer (above) and probed using an anti-mouse (IgG)-HRP (The Binding Site, San Diego, Calif.; HRP=horseradish peroxidase) conjugate (50 μL/well) or other appropriate antibody for 30 minutes. After washing with ELISA wash buffer the reaction was visualized by the addition of TM blue substrate (50 μL/well). After 10 minutes, the reaction was stopped by the addition of 1N $H_2SO_4$ (100 μL/well) and read on an ELISA plate reader set at 450 nm.

2. Synthetic Peptide ELISA

A 20 amino acid residue synthetic peptide (NANP)$_5$ was diluted to a concentration of 2 μg/mL in coating buffer (50 mM sodium bicarbonate, pH 9.6) and coated onto the wells of ELISA strips (50 μL/well). Peptides were dried onto the wells by incubating overnight (about 18 hours), in a hood with the exhaust on. Next morning, the wells were washed with ELISA wash buffer (phosphate buffered saline, pH 7.4, 0.05% Tween®-20) and blocked with 3% BSA in PBS (75 μL/well) for 1 hour. ELISA strips were stored, dry, at −20° C. until needed.

To determine antibody antigenicity of particles, antisera (monoclonal or polyclonal) were diluted using 1% BSA in PBS, and 50 μL/well added to antigen-coated ELISA wells. Sera were incubated for 1 hour, washed with ELISA wash buffer, and probed using an anti-mouse (IgG)-HRP conjugate or other antibody (as above at 50 μL/well) for 30 minutes, washed again with ELISA wash buffer, and then visualized by the addition of TM blue substrate (50 μL/well). After 10 minutes, the reaction was stopped by the addition of 1N $H_2SO_4$ (100 μL/well) and read on an ELISA plate reader set at 450 nm.

B. Immunogenicity of Particles

To assay the immunogenicity of particles, mice were immunized, IP, with 20 μg of particles in Freund's complete adjuvant, and then boosted at 4 weeks with 10 μg in Freund's incomplete adjuvant. Mice were bled at 2, 4, 6, and 8 weeks.

C. Sporozoite IFA

Indirect immunofluorescence assay (IFA) was carried out using glutaraldehyde-fixed *P. falciparum* sporozoites and FITC-labeled anti-mouse IgG (gamma-chain specific) (Kirkegaard and Perry, Gaithersburg, Md.) to detect bound antibody [Munesinghe et al., *Eur. J. Immunol.* 1991, 21, 3015–3020]. Sporozoites used were dissected from the salivary glands of Anopheles mosquitoes infected by feeding on *P. falciparum* (NF54 isolate) gametocytes derived from in vitro cultures.

EXAMPLE 4

Expression of Recombinant Chimer HBc Particles

A. Effect of Insertion Position on Immunogenicity

Antibody titers (1/reciprocal dilution) were measured for mice immunized with HBc particles containing the P. f-CS B cell epitope (NANP)$_4$, inserted either between amino acids E77/D78 or D78/P79, or by using a loop replacement approach (CS-2) [discussed in Schodel et al., (1994) *J. Exp. Med.*, 180:1037–1046, using complete Freund's adjuvant]. Mice were immunized with a single 20 μg dose, IP, with adjuvant as noted before, and antibody titers determined in an ELISA using immobilized (NANP)$_5$ synthetic peptide. The results of those studies are shown in Table 1, below.

TABLE 1

| Time | CS-2* | E77/D78 (V1) | D78/P79 (V2) |
| --- | --- | --- | --- |
| 2 weeks | 0 | 2,560 | 2,560 |
| 4 weeks | 640 | 2,560 | 40,960 |

*Schodel et al., (1994) J. Exp. Med., 180:1037–1046.

Another comparison was made of insertion position of the NANP CS-repeat epitope on immunogenicity, using BALB/c mice. Antibody titers induced by the CS-2 particle of Schodel et al. were compared to titers achieved using the same (NANP)$_4$ B cell epitope, inserted between HBc positions 78 and 79, and using the above V2.Pf1 particles as immunogen. Sera were analyzed 4 weeks after primary (1°) and 2 weeks after booster (2°) immunization, and the results are shown in Table 2, below.

TABLE 2

| Chimer | Primary | Booster |
| --- | --- | --- |
| CS-2 | 0 | 640* |
| V2.Pf1 | 10,240 | 655,360 |

*Schodel et al., (1994) J. Exp. Med., 180:1037–1046

A similar comparison of insertion position of the NANP CS-repeat epitope on immunogenicity was made using B10.S mice, and the results are shown in Table 3.

TABLE 3

| Chimer | Primary | Booster |
| --- | --- | --- |
| CS-2 | 640* | 20,480* |
| V2.Pf1 | 163,840 | 655,360 |

*Schodel et al., (1994) J. Exp. Med., 180:1037–1046

The effect on the immunogenicity of HBc chimer particles (ELISA, F1 mice) that include the minor B cell epitope, NANPNVDP (SEQ ID NO:126) that includes the sequence NVDP (SEQ ID NO: 185), along with a repeated NANP sequence was examined. A HBc chimer was expressed that contained the sequence NANPNVDP(NANP)$_3$NVDP (SEQ ID NO:2; V12.Pf3) inserted between HBc positions 78 and 79. The resulting ELISA data were compared to titers obtained using the tetrameric repeat (NANP)$_4$ B cell epitope (V12.Pf1) or the dimer of the minor B cell epitope at the same position (V12.Pf7). Each of these three chimers contained a Domain IV that included the HBc sequence from position 141 through 149, bonded to the *P. falciparum* universal T cell epitope as the C-terminal sequence. The results of these studies using primary and booster immunizations as discussed before and using adjuvants, are shown below in Table 4.

TABLE 4

| Chimer | Primary | Booster |
|---|---|---|
| V12.Pf1 | 163,840 | 655,360 |
| V12.Pf3 | 2,621,440 | 10,485,760 |
| V12.Pf7 | 2,560 | | such that the lowest titer is expressed as 1. For example, V12.Pf3 was 165 fold more antigenic than V12.Pf3.10 for the (NANP)$_4$-specific monoclonal, and 26-fold more antigenic than V12.Pf3.2 for the NANPNVDP-specific monoclonal antibody. N.D.=no detectable antibody binding. [Note: V12.Pf3.7 was not expressed due to a mutation in the expression vector; it was not examined further because similar constructs were not antigenic, and re-cloning was therefore not a worthwhile endeavor.]

TABLE 5

| Name | P. falciparum B Cell Epitope | Relative Expression | Antigenicity (NANP)$_4$ | NANPNVDP |
|---|---|---|---|---|
| V12.Pf1 | (NANP)$_4$ SEQ ID NO: 1 | **** | 33 | ND |
| V12.Pf3 | NANPNVDP(NANP)$_3$NVDP SEQ ID NO: 2 | ** | 165 | 31 |
| V12.Pf3.1 | NANPNVDP(NANP)$_3$ SEQ ID NO: 3 | **** | 33 | 31 |
| V12.Pf3.2 | (NANP)$_3$NVDPNANP SEQ ID NO: 4 | *** | 33 | 1.2 |
| V12.Pf3.3 | NANPNVDP(NANP)$_3$-NVDPNANP SEQ ID NO: 5 | ** | 5 | 1 |
| V12.PF3.4 | NPNVDP(NANP)$_3$NV SEQ ID NO: 6 | **** | 5 | 5 |
| V12.PF3.5 | NPNVDP(NANP)$_3$NVDP SEQ ID NO: 7 | **** | 5 | 5 |
| V12.PF3.6 | NPNVDP(NANP)$_3$-NVDPNA SEQ ID NO: 8 | **** | 5 | 5 |
| V12.PF3.7 | NVDP(NANP)$_3$NV SEQ ID NO: 9 | — | — | — |
| V12.PF3.8 | NVDP(NANP)$_3$NVDP SEQ ID NO: 10 | **** | 5 | 1 |
| V12.PF3.9 | NVDP(NANP)$_3$NVDPNA SEQ ID NO: 11 | *** | 5 | ND |
| V12.PF3.10 | DP(NANP)$_3$NV SEQ ID NO: 12 | **** | 1 | ND |
| V12.PF3.11 | DP(NANP)$_3$NVDP SEQ ID NO: 13 | **** | 5 | ND |
| V12.PF3.12 | DP(NANP)$_3$NVDPNA SEQ ID NO: 14 | *** | 5 | ND |

The observed greater than 20-fold increase in immunogenicity by including the 'minor' repeat epitope was quite unexpected. Because V12.Pf3 was not well expressed by E. coli, variants of the Pf3 epitope NANPNVDP(NANP)$_3$NVDP (SEQ ID NO:2) were constructed that had similar antigenicity to Pf3, but with increased expression levels, as shown below. Only constructs 3.1 and 3.2 were assayed for immunogenicity.

Relative expression levels of recombinant chimer HBc/P. falciparum particles and antigenicities for monoclonal antibodies specific for the CS epitopes (NANP)$_4$ and (NANPNVDP) are shown in Table 5 below. Relative expression levels are as follows; **=75–125 mg/L; *=50–75 mg/L; **=25–50 mg/L. Antigenicity was determined by end point titer dilutions for the monoclonal antibodies [MoAb 2A10 for (NANP)$_4$; MoAb 2B6D8 for NANPNVDP; and P. vivax Rpt. MoAb 2F2 were provided by E. Nardin of New York University Medical Center]. The data were normalized Immunogenicity of selected HBc chimer particles containing variants of the Pf3 epitope were assayed as described above. Sera were analyzed by ELISA 4 weeks after primary (1°) and 4 weeks after booster (2°) immunizationsd. The data obtained are shown in Table 6, below, in which the "Name" of the chimer and the corresponding sequence of the B cell immunogen are as illustrated above.

TABLE 6

| NAME | PRIMARY | SECONDARY |
|---|---|---|
| V12.Pf1 | 40,960 | 655,360 |
| V12.Pf3 | 2,621,440 | 10,485,760 |
| V12.Pf3.1 | 2,621,440 | 10,485,760 |
| V12.Pf3.2 | 2,621,440 | 2,621,440 |

Surprisingly, a version that contained one copy of the NANPNVDP repeat (V12.Pf3.1; SEQ ID NO: 126) was as immunogenic (and expressed better) as a version containing 2 copies (V12.Pf3), despite being 5-fold less antigenic for the NANP monoclonal antibody.

B. Expression Failures

Several additional epitopes have been attempted to be placed into the HBc loop (Domain II) between positions 78 and 79 (as in V2.Pf1), and have failed to be expressed for reasons unknown. Table 7, below, enumerates those epitopes that have failed to express when inserted between D78 and P79 (V2) in a HBc chimer.

TABLE 7

| Designation | Source of Epitope | Epitope (single letter) |
|---|---|---|
| V2.FGF-1 (N7-K12) | Human FGF-1 | NYKKPK SEQ ID NO: 127 |
| V2.FGF-1 (K118-H124) | Human FGF-1 | KRGPRTH SEQ ID NO: 128 |
| V2.Arom-479 | P450 Aromatase | LHPDETKNMLEMIFTPRNSDR SEQ ID NO: 129 |
| V2.HIV3.1 | HIV-1 (gp120) | RIKQI SEQ ID NO: 130 |
| V2.HIV4.1 | HIV-1 (gp120) | RIKQIGMPGGK SEQ ID NO: 131 |
| V2.HIV5.1 | HIV-1 (gp41) | LLELDKWASL SEQ ID NO: 132 |
| V2.HIV6.1 | HIV-1 (gp41) | EQELLELDKWASLW SEQ ID NO: 133 |
| V2.HIV9.1 | HIV-1 (gp41) | VQQQNNLLRAIEAQQHLL-QLTVWGIKQLQARIL SEQ ID NO: 134 |
| V2.HIV10.1 | HIV-1 (gp41) | HLLQLTVWGIKQLQAR SEQ ID NO: 135 |
| V2.HIV12.1 | HIV-1 (gp41) | YTHIIYSLIEQSQNQQEK-NEQELLALDKWASLWNWF SEQ ID NO: 136 |
| V2.HIV13.1 | HIV-1 (gp41) | YTHIIYSLIEQSQN-QQEKNEQELLEL SEQ ID NO: 137 |
| V2.1A2 (351–370) | Human P450-1A2 | GRERRPRLSDRPQLPYLEA SEQ ID NO: 138 |
| V2.2D6 (129–148) | Human P450-2D6 | REQRRFSVSTLRNLGLGKKS SEQ ID NO: 139 |
| V2.Py-B1 | *P. yoelii* (TRAP) | PNKLPRSTAVVHQLKRKH SEQ ID NO: 140 |
| V2.Py-B3 | *P. yoelii* (TRAP) | TAVVHQLKRKH SEQ ID NO: 141 |
| V2.Pv-T1A | *P. vivax* | PAGDRADGQPAGDRAAAGQPAG SEQ ID NO: 142 |
| V2.ALV1.2 | ALV-J | NQSWTMVSPINV SEQ ID NO: 143 |
| V2.ALV1.2 | ALV-J | MIKNGTKRTAVTFGSV SEQ ID NO: 144 |
| V2.FMDV (142–160) | FMDV | PNLRGDLQVLAQKVARTLP SEQ ID NO: 145 |
| V2.FMDV (135–160) | FMDV | RYNRNAVPNLRGDL-QVLAQKVARTLP SEQ ID NO: 146 |

EXAMPLE 5

Determination of 280:260 Absorbance Ratios

Protein samples were diluted to a concentration of between 0.1 and 0.3 mg/mL using phosphate buffered saline (PBS), pH 7.4. The spectrophotometer was blanked, using PBS, and the absorbance of the protein sample measured at wavelengths of 260 nm and 280 nm. The absorbance value determined for a sample at 280 nm was then divided by the absorbance value determined for the same sample at 260 nm to achieve the 280:260 absorbance ratio for a given sample. The ratios obtained for several samples, including native particles (HBc 183), HBc particles truncated after residue position 149 (HBc 149), and several HBc chimers that are identified elsewhere herein, are shown below in Table 8.

TABLE 8

| Particle | 280/260 Absorbance Ratio |
|---|---|
| HBc183 | 0.84 |
| HBc149 | 1.59 |
| V2.Pf1 | 1.64 |
| V2.Pf1 + C150 | 1.5 |
| V2.Pf1 + Pf/CS-UTC | 1.54 |
| V2.Pf1 + Pf/CS-UTC (C17A) | 1.42 |

EXAMPLE 6

Cysteine at the C-terminus of Truncated HBc Particle

A. Addition of a Cysteine Residue to the C-terminus of Hybrid HBc Particles

Using the polymerase chain reaction (PCR), genes expressing hybrid HBc particles can be easily mutated to introduce a cysteine or cysteine-containing peptide to the C-terminus of HBc. For example, a PCR oligonucleotide primer such as that of SEQ ID NO:148 can be used, in concert with a suitable second primer, to amplify a hybrid HBc gene and incorporate a cysteine codon between codon V149 and the stop codon.

Hepatitis B core particles can be truncated from residue position 183 (or 185, depending on viral subtype) to 140 and retain the ability to assemble into particulate virus-like particles. Many groups have used particles truncated to amino acid 149 because amino acid 150 represents the first arginine residue of the arginine-rich C-terminal domain.

To assess the ability of a single cysteine residue to stabilize HBc particles, a codon for a cysteine residue was inserted using techniques described before between the codon for HBc amino acid residue V149 and the termination codon of a chimer HBc molecule that contained the $(NANP)_4$ malarial B cell epitope inserted between residues 78 and 79 (referred to herein as V2.Pf1) to form the chimeric molecule and particle referred to as V2.Pf1+C. The thermal stability (at 37° C.) of this chimer particle (V2.Pf1+C), as compared to a similar chimer particle lacking the inserted cysteine (V2.Pf1), was found to be dramatically increased, as is seen in FIG. 3.

It is noted that vectors and expression products that are prepared by addition of a cysteine to the C-terminus of a V2 construct are sometimes referred to herein as V16 vectors or expression products.

As can readily be seen in FIG. 3, the two particles started out similarly. However, after fourteen days at 37° C., the cysteine-containing particle exhibited fewer bands on the SDS gel, indicating enhanced stability as compared to the particle lacking the added Cys residue.

B. Thermal Stability Protocol

Purified particles were diluted to a concentration of 1 mg/mL using 50 mM $NaPO_4$, pH 6.8 and sodium azide was added to a final concentration of 0.02% to prevent bacterial growth. Particles were incubated at 37° C. and aliquots were taken at the time points indicated in the drawing description. Samples were mixed with SDS-PAGE sample buffer (reducing) and run on 15% SDS-PAGE gels. Gels were stained using Coomassie Blue, and then analyzed.

EXAMPLE 7

Analytical Gel Filtration Analysis of Hybrid Particles

Analytical gel filtration analysis of purified hybrid HBc particles was performed using a 25 mL Superose® 6 HR 10/30 chromatographic column (Amersham Pharmacia # 17-0537-01) and a BioCAD™ SPRINT Perfusion Chromatography System. The UV detector was set to monitor both wavelengths of 260 and 280 nm. The column was equilibrated with 3 column volumes (CV; about 75 mL) of buffer (50 mM NaPO$_4$, pH 6.8) at a flow rate of 0.75 mL/minute.

The particles to be analyzed were diluted to a concentration of 1 mg/mL using 50 mM NaPO$_4$, pH 6.8. 200 Microliters (μL) of the sample were then loaded onto a 200 μL loop and injected onto the column. The sample was eluted from the column with 50 mM NaPO$_4$, pH 6.8 at a flow rate of 0.75 mL/minute.

Particles containing C-terminal cysteine residues or similar particles free of such cysteines were analyzed using the above procedure. Integration of the 280 nm trace was carried out using BioCAD™ software (PerSeptive™) to provide the results in Table 9A, below.

TABLE 9A

| Particle | Percent After Purification | |
|---|---|---|
| | Particulate | Non Particulate |
| V12.Pf1 (C17A) | 67 | 33 |
| V12.Pf1 (C17A) + C150* | 100 | 0 |
| V12.Pf1* | 98 | 2 |
| V2.Pf1 + CfHBc74-87 + C* | 97.8 | 2.2 |
| V2.Pf1 + CfHBc74-87 | 80.7 | 19.3 |

*C-terminal cysteine-stabilized particles.

Purified particles were assayed for the percentage of particles and then incubated in aqueous solution at 37° C. as discussed before. The compositions were assayed for stability after fourteen days of incubation. The results of this analysis are shown in Table 9B, below.

TABLE 9B

| Particle Name | Percent Particles Following Incubations at 37° C. (Days) | |
|---|---|---|
| | Zero | 14 |
| V12.Pf1* | 98 | 96 |
| V12.Pf1 (C17A) | 67 | 63 |
| V12.Pf1 (C17A) + C150* | 100 | 98 |

*See the note to Table 9A.

FIG. 7 shows the results of a SDS-PAGE analysis of the particles of Table 9B at days zero, 7 and 14 following incubation at 37° C. Results of a densitometric analysis of that SDS-PAGE analysis are shown in Table 9C, below.

TABLE 9C

| Particle | Percent Full Length Monomer Following Incubation at 37° C. Days | | |
|---|---|---|---|
| | Zero | 7 | 14 |
| V12.Pf1* | 100 | 94 | 93 |
| V12.Pf1 (C17A) | 100 | 13 | 1 |
| V12.Pf1 (C17A) + C150* | 100 | 83 | 63 |

*See the note to Table 9A.

The particles of Tables 9A-9C and control particles that contained an added lysine residue between HBc residues usually numbered 76 and 77 without [HBc150 (K77)] and with a C-terminal Cys residue [HBc150 (K77)+C] were analyzed for immunogenicity in BALB/c mice via intraperitoneal injection using 20 μg of the respective particles in phosphate buffered saline (pH 7.4) in the absence of adjuvant, contrary to the results reported in Example 4. Sera were analyzed two weeks after immunization using an ELISA with HBc particles (Anti-HBc) or (NANP)$_5$ synthetic peptide [Anti-(NANP)$_n$] as the solid phase capture antigen. The results of this study are shown in Table 9D, below

TABLE 9D

| Particle | End Point Titer | |
|---|---|---|
| | Anti-HBc | Anti-(NANP)$_n$ |
| V12.Pf1 (C17A) | 10,240 | 0 |
| V12.Pf1 (C17A) + C150* | 10,240 | 2,560 |
| V12.Pf1* | 10,240 | 10,240 |
| HBc150 (K77) | 40,960 | 0 |
| HBc150 (K77) + C* | 163,840 | 0 |

*See the note to Table 9A.

The data from this study are interpreted to mean that the C-terminal cysteine-stabilized particles are more stable immediately on production, as well as after incubation at 37° C. for various time periods. The stabilized particles also exhibit enhanced immunogenicity, even in the absence of adjuvant. In addition, although particulate matter is present in the non-stabilized material such as V12.Pf1(C17A), there are no monomeric chimeric proteins after fourteen days of incubation and the material present does not induce antibodies toward the initially introduced heterologous B cell epitope sequence, here a malarial immunogen.

EXAMPLE 8

Cysteine Located Within a Peptide Fused to the C-terminus of an HBc Hybrid

Studies were conducted to determine if there were an absolute requirement for a cysteine residue to be the final amino acid of the HBc gene (as it is in wild type HBc) or if a cysteine could function internally in an introduced C-terminal sequence.

A peptide corresponding to a 20-residue universal T cell epitope, derived from the CS protein of the malarial parasite *Plasmodium falciparum*, which contains a cysteine at position 17 of the peptide or 342 of the CS protein, [Calvo-Calle et al., *J. Immunol.*, (1997) 159(3):p. 1362–1373], was fused to the C-terminus of a HBc chimer (V2.Pf1). This chimer contains the HBc sequence from position 1 through position 149, with the *P. falciparum* B cell epitope (NANP)$_4$ inserted between amino acid residues 78 and 79. Domain I of this HBc construct thus contained residues 1–75; Domain II contained residues 76–85 with the (NANP)$_4$ epitope inserted between residues 78 and 79 (along with four residues comprising the restriction sites); Domain III contained residues 86–135; and Domain IV contained residues 136–149 plus the 20-residue *P. falciparum* T cell epitope and two residues from the EcoRI cloning site (GI).

This fused C-terminal peptide is 20 amino acid residues long (12 or 14 amino acids shorter than the wild type sequence, depending on virus subtype) and has a predicted pI value more than 8 pH units lower than the wild type sequence. To minimize potential stabilizing effects that may be contributed by amino acids other than the cysteine, a (similar) control construct was made, having an alanine instead of a cysteine at position 17 (see Table 10, below).

To enable simple assessment of the stabilizing effects of this sequence, the peptides were fused to the C-terminus of a particle previously shown to degrade readily at 37° C. (V2.Pf1) to form the HBc chimers denominated V2.Pf1+Pf/CS-UTC and V2.Pf1+Pf/CS(326–345/C342A), respectively. The results of a thermal stability study over a 28 day time period (as discussed previously) are shown in FIG. 4.

The results of this study showed that the presence of the cysteine in the T cell epitope derived from the CS protein of *P. falciparum* was needed for particle stability in the time period studied, and that there was no absolute requirement that that cysteine be at the C-terminus of the epitope. The table below shows the amino acid sequences of C-terminal fusions with a cysteine or alanine at position 17, relative to the native sequence, which occurs in the wild type HBc protein.

TABLE 10

| Source | Sequence | pI | Length | Cys Position | Cys Shift |
|---|---|---|---|---|---|
| Native | RRRGRSPRRRT-PSPRRRRSQSP-RRRRSQSRESQC SEQ ID NO: 147 | 12.74 | 34 | 34 | zero |
| Pf/CS-UTC | (GI) EYLNKIQNS-LSTEWSPCSVT SEQ ID NO: 148 | 4.44 | 20 | 17 | −15 |
| Pf/CS-UTC (C17A) | (GI) EYLNKIQNS-LSTEWSPASVT SEQ ID NO: 149 | 4.44 | 20 | N/A | N/A |

(GI) = residues added from cloning site.

EXAMPLE 9

*P. Vivax* HBc Chimers

Following the work discussed before on HBc chimers containing *P. falciparum* B cell and T cell immunogens, similar work was carried out using sequences from the *P. vivax* CS protein. Exemplary constructs are illustrated below in Table 11.

TABLE 11

| *P. vivax* Immunogen Type | Malarial B Cell Immunogen (Between D78/P79) | CS-UTC (After V149) |
|---|---|---|
| Type-I | (DRAAGQPAG) SEQ ID NO: 152 (DRADGQPAG) SEQ ID NO: 153 | YLDKVRATVGTEWTPCSVT SEQ ID NO: 25 |
| Type-II | (ANGAGNQPG) SEQ ID NO: 154 (ANGAGDQPG) SEQ ID NO: 155 (ANGADNQPG) SEQ ID NO: 156 (ANGADDQPG) SEQ ID NO: 157 | YLDKVRATVGTEWTPCSVT SEQ ID NO: 25 |
| Type-III ('*Vivax*-like') | (APGANQEGGAA) SEQ ID NO: 158 | YLDKVRATVGTEWTPCSVT SEQ ID NO: 25 |

To address the variability of the repeats, the following variant epitopes were used for insertion into HBc between amino acids 78 and 79:

1. Type-I CS-repeat

PAGDRADGQPAGDRAAGQPAG (*P. vivax*-type 1A)—SEQ ID NO: 159. This form of the epitope failed to make a particle.

DRAAGQPAGDRADGQPAG (*P. vivax*-type 1B)—SEQ ID NO: 150. This form of the epitope, containing flanking dipeptide cloning site remnants, successfully made a particle and is referred to as V2.PV-TIB. An immunogen for *P. vivax*-type I has been successfully cloned, expressed, purified, and its immunogenicity tested in mice. The results of that mouse study are shown in Table 12, hereinafter.

2. Type-II CS-repeat

For type-II, this work is complicated by the existence of four different forms of the type-II epitope. These forms contain either G or D at position 5, and either N or D at position 6 [Qari et al., *Mol. Biochem. Parasitol.*, (1992) 55(1–2):p. 105–113]. Hence, there are 4 different possible repeat sequences (GN, GD, DN, and DD) needed to maximize the possibility of success. The first, and preferred approach, is to prepare a single hybrid particle containing all four repeats, as shown below by underlines. This approach was successfully employed to address the variability in the type-I repeat. Each of these constructs contains flanking dipeptide cloning site remnants.
ANGA<u>GN</u>QPGANGA<u>GD</u>QPGANGA<u>DN</u>QPGANGA<u>DD</u>QPG (*P. vivax*-type II-GN/GD/DN/DD) SEQ ID NO: 151.

The above sequence has been cloned, expressed, and purified as a HBc chimer with no modification to the C-terminus.

The second approach was to prepare two hybrid particles, whereby each particle contained two of the variant epitopes (see below). This approach is less preferable because it requires either the use of a more complex expression system to direct the production of 'mixed' particles during expression, or the mixing of type-II particles following manufacture.

ANGA<u>GN</u>QPGANGA<u>GD</u>QPG     SEQ ID NO:160.
(*P. vivax*-type II-GN/GD)

QANGA<u>DN</u>QPGANGA<u>DD</u>QPG     SEQ ID NO:161.
(*P. vivax*-type II-DN/DD)

CGCGAATTCAAGCGAACGGCGCCGATAATCAGCCGGCGGGTGCA     SEQ ID NO:162.
(*P. vivax*-type IIB-ER1-wt-F)

3. Type-III ('vivax-like') CS-repeat

The third P. vivax CS-epitope, which is quite different from the other two, is not associated with amino acid variation (see below) [Qari et al., Lancet, 1993. 341(8848): p. 780–783]. This sequence was cloned into the HBc expression system, and hybrids were produced that contained flanking dipeptide cloning site remnants.

APGANQEGGAAAPGANQEGGAA    (P. vivax-type III) SEQ ID NO:163.

4. T cell Epitope at the C-terminus of HBc

The insertion of the P. vivax Th epitope (Pv-UTC; YLD-KVRATVGTEWTPCSVT; SEQ ID NO:25) into HBc and HBc hybrids was also performed using synthetic DNA fragments (Synthetic Genetics, San Diego Calif.). However, unlike B cell epitopes, which are inserted into the immunodominant loop region of the HBc gene, T cell epitopes are fused to the C-terminus of the HBc gene. Previously discussed cloning vectors were used for the insertion of both B and Th epitopes into HBc. The particle expressing just the Pv-UTC at the C-terminus has also been successfully made.

5. Combining B and T cell Epitopes in a Single Particle

To combine B and Th epitopes into single HBc constructs, PCR is used to amplify N-terminal HBc fragments (residues 1–80, which contain the B cell epitopes), and C-terminal HBc fragments (residues 81–150, which contain the T cell epitopes). The fragments are ligated together and amplified again by PCR. Again, clones are verified by restriction endonuclease mapping and automated DNA sequence analysis (Lark Technologies, Houston Tex.). Details are essentially the same as for P. falciparum. Particles that contain each of the Type-I, -II and -III B cell epitopes and variants as well as the Pv-UTC, have been expressed and recovered.

EXAMPLE 10

Relative Immunogenicities of HBc Chimers

Relative immunogenicities of several HBc chimer immunogens were compared in mice using the IFA assay discussed previously. The results of those studies using two dose immunization regimens as before are shown below in Table 12.

TABLE 12

| Immunogen | IFA titer | Protection | Citation |
| --- | --- | --- | --- |
| P. berghei (CS-1) | 40,960 | 95% | A |
| P. yoelii (CS-3) | 12,800 | 95%* | B |
| P. falciparum (CS-2) | 1,200 | NT | A |
| P. falciparum (V12.Pf3.1) | 5,200,000 | NT | — |
| P. vivax (V2.PV-TIB) | 160,000 | NT | — |

[A = Schodel et al., J. Exp. Med., 1994, 180:1037–1046. B = Schodel et al., Behring Inst. Mitt., 1997(98): p. 114–119. NT = not tested. *= protection for greater than 3 months.]

As is seen from the above data, titers of $10^5$–$10^6$ for P. falciparum were achieved using a contemplated chimeric immunogen; this compares to titers of only $10^4$ for P. berghei and $10^3$ for P. falciparum using the replacement technology of Schodel et al.

Figure 5:
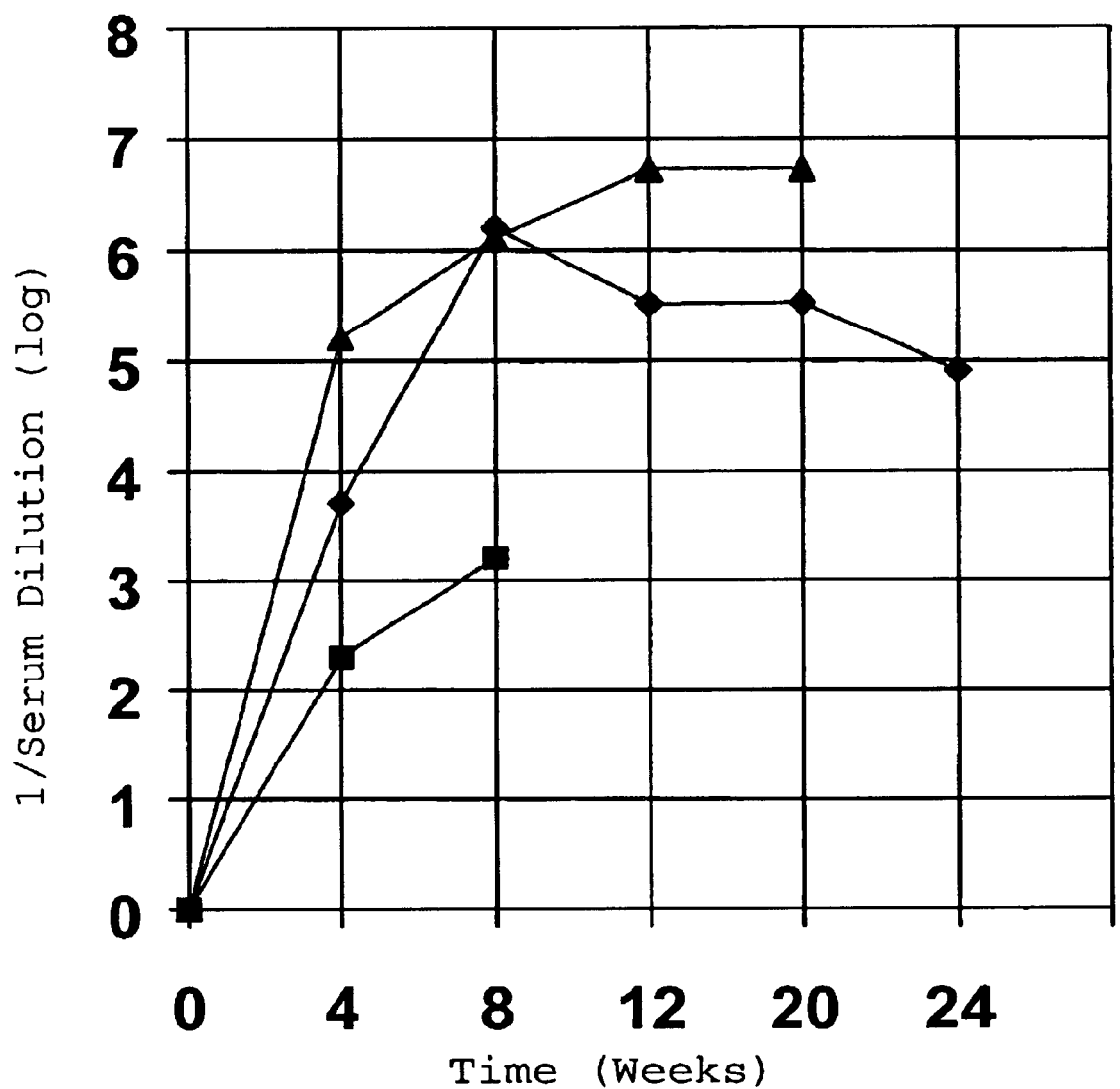

Mice were immunized with CS-2 or V12.Pf1 using 20 µg of particles on day zero and were boosted with 10 µg at four weeks. Mice immunized with particles from V12.Pf3 and V12.Pf3.1 were immunized using 20 µg of particles on day zero and were boosted with 10 µg at eight weeks using adjuvants as discussed before. Data showing the duration of the titers achieved are shown in FIG. 5, with data for use of V12.Pf3 particles being essentially identical to data with V12.Pf3.1 particles, and not shown.

EXAMPLE 11

Relative HBc Antigenicities

A series of studies was carried out to determine the relative antigenicities of several malarial HBc chimer particles toward two monoclonal antibodies (MoAb-3120 and MoAb-3105) as compared to native HBcAg (particle). These antibodies are specific to the loop region of HBc, and were the gracious gift of the Immunology Institute, Tokyo, Japan. Studies were carried out using the chimers of Table 5 that contain malarial epitopes inserted into HBc particles at various positions as antigens in ELISA assays with the monoclonals as probes. The results of these studies (as end point dilutions) are shown below in Table 13A, 13B, and 13C, and illustrate the substantial lack of antigenicity of a contemplated chimer toward monoclonal antibodies that bind to the loop region, the primary immunogen, of HBc. Put differently, monoclonal antibodies that bind specifically to the loop region of HBc barely recognize a contemplated chimer, if at all.

TABLE 13A

| Particle | Anti-MoAb-3120 End Point Dilution | Relative Antigenicity |
| --- | --- | --- |
| HBcAg | 625000 | 100 |
| V12.Pf3 | 80000 | 12.8 |
| V12.Pf3.1 | 20000 | 3.2 |
| V12.Pf3.2 | 10000 | 1.6 |
| V12.Pf3.3 | 10000 | 1.6 |
| V12.Pf3.4 | 80000 | 12.8 |
| V12.Pf3.5 | 40000 | 6.4 |
| V12.Pf3.6 | 80000 | 12.8 |
| V12.Pf3.8 | 80000 | 12.8 |
| V12.Pf3.9 | 160000 | 25.6 |
| V12.Pf3.10 | 10000 | 1.6 |
| V12.Pf3.11 | 80000 | 12.8 |
| V12.Pf3.12 | 80000 | 12.8 |

TABLE 13B

| Particle | Anti-MoAb-3105 End Point Dilution |
| --- | --- |
| HBcAg | 1,300,000 |
| V2.Pf1 (78/79) | Zero |
| V12.Pf1 (78/79) | Zero |
| V12.Pf3 (78/79) | Zero |
| V1.Pf1 (77/78) | Zero |
| V13.Pf1 | 1,300,000 |

An insertion into several sites in the immunodominant loop (including positions 77–78 or 78–79) totally eliminates binding of MoAb-3105. V13 is an insertion between residues 129 and 130 and is used as a control because the native HBc immunodominant loop remains intact in this construct.

TABLE 13C

| Particle | Anti-MoAb-3120 End Point Dilution |
|---|---|
| 77/78 V1.Pf1 | 102,400 |
| 78/79 V2.Pf1 | 400 |
| HBcAg | 409,600 |

These data show that insertion between residues 78 and 79 causes a more drastic reduction in anti-MoAb-3120 binding as compared with insertion between residues 77 and 78.

EXAMPLE 12

Preparation of Vector for Preparation of HBc Particles for Use in Humans

A. Preparation of Vector V17Pf3.1

To manufacture the particle V12.Pf3.1 in a manner suitable for human administration, it was necessary to express the particle using an expression system that did not require the use of ampicillin to ensure plasmid maintenance. To achieve this, the gene coding for the particle, along with the necessary upstream regulatory sequences, was inserted into a new plasmid that utilizes kanamycin as the selectable marker. The new plasmid (V17.Pf3.1) was synthesized using a two step cloning procedure:

Step 1: The plasmid pKK223-3N-V12 was digested with the restriction enzymes BamHI and HindIII to yield two DNA fragments of 801 and 4869 bp. In addition, the commercially available plasmid pREP4 (Qiagen) was cut with BglII and HindIII to yield two fragments of 320 bp and 3420 bp. The 3420 bp and 801 bp fragments were ligated to create plasmid V17. (It is noted that BglII and BamHI digested DNAs can be ligated by virtue of their common 'overhang' sequences, although neither BglII or BamHI can cut the resultant fragment). The V17 plasmid, therefore, contains the HBc149 gene, complete with Pf-UTC sequence fused to the C-terminus, and EcoRI and SacI restriction sites in the immunodominant loop region to enable insertion of epitopes between D78 and P79 of the HBc gene.

Step 2: The second step was to insert the Pf3.1 version of the Pf CS-repeat epitope into the immunodominant loop region of the gene. This was achieved by digesting V17 with SacI and EcoRI to yield 15 bp and 4206 bp DNA fragments. Annealed oligonucleotides encoding the Pf3.1 epitope were ligated with the 4206 bp fragment to yield V17.Pf3.1, a 4275 base pair plasmid. In addition to the gene that encodes the 195 amino acid malaria vaccine candidate, this plasmid contains a gene for the lac repressor (lac I) to force any gene under lac promoter control to be fully repressed until induced by isopropylthiogalactoside (IPTG). It also has a kanamycin resistance gene to permit positive selection via the addition of kanamycin to culture media. The plasmid has the replication origin of pACYC 184 and is not considered to be a high copy number plasmid.

The locations of the genes of interest are:

| Gene | Start | Stop | Amino Acids | Molecular Weight (kDa) |
|---|---|---|---|---|
| Lac I | 2128 | 3087 | 319 | 34.1 |
| V17.Pf3.1 | 281 | 868 | 195 | 21.7 |
| KmR | 4259 | 3465 | 264 | 29.1 |

A suitable host for V17.Pf3.1 is *E. coli* BLR, a rec A derivative of *E. coli* BL21, and a common strain used for the production of recombinant proteins (available for purchase from Novagen). *E. coli* BLR was selected as a host organism for expression because of its increased genetic stability, as well as its ability to produce assembled particles in soluble form (not in inclusion bodies).

B. Expression of Particles Using Plasmid V17.Pf3.1

*E. coli* (Strain BLR) containing the V17.Pf3.1 plasmid were streaked onto an LB agar plate supplemented with 25 μg/mL kanamycin and 10 μg/mL tetracycline, then incubated at 37° C. for 16–20 hours. A single colony was then used to inoculate 3 mL of TB-Phy medium in a sterile culture tube, supplemented with 25 μg/mL kanamycin. The tube was incubated overnight (about 18 hours) on a shaker at 37° C. and about 200 rpm.

The following morning, 100 mL of TB-Phy medium was warmed to 37° C. One mL of the overnight culture was removed and used to inoculate the flask, which was then incubated on a shaker at 37° C. at about 200 rpm for six hours.

The fermentor (Biostat™ UE20) was inoculated with 100 mL of inoculum with the fermentor conditions set as follows:

| | |
|---|---|
| Agitation | 400 rpm |
| Temperature | 37° C. |
| Aeration | air, 10 liters per minute |
| pH | 7.0, uncontrolled |

The $A_{600}$ value was measured for the first sample, and for samples every 20–30 minutes thereafter to monitor $A_{600}$. An IPTG solution was prepared by dissolving 62 mg IPTG in 10–15 mL water. When the $A_{600}$ value reached 0.5, the filter-sterilized IPTG solution was aseptically added to the fermentor through a syringe. The incubation was continued until next day (e.g. about another 10–24 hours).

At 14 hours after induction, the fermentor temperature was set to 15° C. Harvesting of cells was started by centrifugation in a Beckman® J2-MC centrifuge with following conditions:

| | |
|---|---|
| Rotor | JA10 |
| Speed | 7,500 rpm |
| Temperature | 4° C. |
| Time | 9 minutes |

The cells were harvested by freezing into liquid nitrogen.

C. Purification of Particles Expressed by Vector V17.Pf3.1/BLR

The biomass of harvested cells was resuspended in 50 mM sodium phosphate, pH 6.8, and lysed using a French Pressure cell at 16,000 psi. The cell debris was removed by centrifugation using a Beckman® J2-MC centrifuge and the following conditions.

| Rotor: | JA20 |
| --- | --- |
| Speed: | 15,000 rpm |
| Temperature: | 4° C. |
| Time: | 30 minutes. |

The volume of the resultant supernatant was measured and 277 g/L of solid ammonium sulfate were slowly added to the supernatant. The mixture was stirred at 4° C. for 30 minutes. The solution was centrifuged in Beckman® J2-MC centrifuge with the following conditions.

| Rotor: | JA20 |
| --- | --- |
| Speed: | 15,000 rpm |
| Temperature: | 4° C. |
| Time: | 30 minutes |

The precipitate was then resuspended in a minimal volume of 50 mM sodium phosphate buffer and then dialyzed against the same buffer for one hour with stirring. The dialyzed solution was centrifuged in Beckman® J2-MC centrifuge with the following conditions.

| Rotor: | JA20 |
| --- | --- |
| Speed: | 15,000 rpm |
| Temperature: | 4° C. |
| Time: | 15 minutes |

The supernatant was recovered and then subjected to gel filtration chromatography.
 System: Pharmacia Biotech AKTA™ Explorer
 Buffer B (elution solvent): 50 mM Sodium phosphate buffer (pH 6.8).
 Column: Millipore Vantage™ VL44×1000 column (44 mm diameter, 1000 mm height, Catalog No.: 96441000)
 Resin: 1.5 liter Sepharose® CL-4B manufactured by Pharmacia
 Detector: UV at 210, 254 and 280 nm.
 Fraction: 15 mL The column was eluted with buffer B at 2 mL per minute. Particle-containing fractions were identified using SDS-PAGE and pooled. The salt concentration of the pooled material was adjusted to 5M by adding sodium chloride.
Hydrophobic Interaction Chromatography
 System: Pharmacia® Biotech AKTA™ Explorer (System No.: 18111241 001152, University of Iowa ID No.: 540833.)
 Buffer A: 50 mM sodium phosphate buffer (pH 6.8)+5 M NaCl. (The buffer was degassed for 30 minutes daily, before use.)
 Buffer B (elution solvent): 50 mM sodium phosphate buffer (pH 6.8). (The buffer was degassed for 30 minutes daily, before use.)
Hydrophobic Interaction Chromatography using ToyoPearl® Ether 650 Resin
 Column: Millipore Vantage™ VL44×250 column (44 mm diameter, 250 mm height, Catalog No.: 96440250)
 Resin: 200 mL Toyopearl® ether 650 HIC resin, manufactured by Tosohaas
 Detector: UV at 210, 254, and 280 nm
 Fraction: 15 mL The column was equilibrated with 5 column volumes (CV) of buffer A for a one hour time prior to starting purification, using a flow rate of 20 mL/minute. The retentate containing 5 M salt was then loaded at a rate of 20 mL/minute. The column was washed with 2 CV of buffer A, washed with 2 CV of 10% buffer B, eluted with 3 CV of 40% buffer B, and (finally eluted) with 100% buffer B. Fractions were completely analyzed for proteins of interest by SDS PAGE analysis. Pure fractions were combined together, and a protein estimation using a Bradford assay was carried out.
Hydrophobic Interaction Chromatography using Butyl Resin
 Column: Millipore Vantage™ VL44×250 column (44 mm diameter, 250 mm height, Catalog No.: 96440250)
 Resin: 200 mL Toyopearl® Butyl 650-S HIC resin, manufactured by Tosohaas
 Detector: UV at 210, 254 and 280 nm
 Fraction: 15 mL The column was equilibrated with 5 column volumes (CV) of 40% buffer B for one hour prior to starting purification, using a flow rate of 20 ml/min. The combined fractions from ether HIC were loaded at a rate of 20 mL/minute. The column was washed with 2 CV of 40% buffer B, washed with 2 CV 90% B, and eluted with 4 CV of WFI.

Fractions were analyzed for protein of interest by SDS PAGE analysis. Pure fractions were combined together
Hydroxyapatite Column Chromatography
 Column: Millipore Vantage™ VL16×250 column (16 mm diameter, 250 mm height, Catalog No.: 96160250)
 Resin: 20 ml Ceramic Hydroxyapatite (Catalog No. 158-2200)
 Detector: UV at 215, 254 and 280 nm
 Fraction: 15 mL The column was equilibrated with 5 column volumes (CV) of 20 mM sodium phosphate buffer, flow rate: 5 mL/min. Load combined fractions eluted from butyl HIC at 5 mL/min. Wash the column with 20 mM sodium phosphate buffer until A280 drops to baseline. Fractions were analyzed for protein of interest by SDS PAGE analysis. Pure fractions were combined together.
Desalting
 Column: Prepacked desalting column, HiPrep™ 26/10, Pharmacia
 Resin: 20 mL Ceramic Hydroxyapatite (Catalog No. 158-2200)
 Detector: UV at 215, 254 and 280 nm
 Fraction: 15 mL The column was equilibrated with 5 CV of 15 mM Acetate Buffer, pH 6.0. The pooled fractions from the hydroxyapatite column were loaded onto the column, and then eluted with 15 mM Acetate Buffer, pH 6.0, at a flow rate of 20 mL/min. Fractions were analyzed for protein of interest by SDS PAGE analysis. Pure fractions were combined together, and protein estimation was carried out using a Bradford assay. The pure fraction was assayed for endotoxin level, and finally passed through a 0.22-micron filter for terminal filtration.

EXAMPLE 13

Preparation of Vectors to Express Particles with a Cysteine Residue Prior to C-Terminal Fused Epitope To prepare particles with a single cysteine after V149 of the HBc gene, followed by a T cell epitope, a PCR primer was synthesized (SEQ ID NO:165). This primer, in conjunction with HBc149/NcoI-F (SEQ ID No:29), was used to amplify the HBc gene to produce a version of HBc having a single cysteine codon introduced directly after V149, as well as EcoRI and HindIII restriction sites (after the introduced cysteine). The 478 bp PCR product was cut with NcoI and HindIII and cloned into pKK223-3N.

```
                                   SEQ ID No.:164
                      C   V   V   T   T   E   P
5' GCAAGCTTACTATTGAATTCCGCAAACAACAGTAGTCTCCGG
      HindIII      EcoRI
                                   SEQ ID NO:165
```

The resultant plasmid was then cut with EcoRI and HindIII, and the annealed oligonucleotides coding for the Pf-UTC (Pf/CS326–345; SEQ ID NOs: 80 and 81) ligated into the plasmid. This plasmid was then used as the template in a PCR reaction, along with the primers HBc-P79/SacI-F (SEQ ID NO:35) and Pf/CS-UTC(C17A) (SEQ ID NO:104) the resultant PCR product (307 bp) coded for amino acids 79 through 149 of HBc, followed by the introduced cysteine, followed by the Pf/CS-UTC having the C17A mutation [Pf/CS-UTC(C17A)], and flanked by SacI (5') and HindIII (3') restriction sites. This fragment was cut with SacI and HindIII and ligated with the plasmid V2.Pf1 (encoding the malarial (NANP)$_4$ epitope) that had been cut with the same two enzymes.

The resultant gene codes for a 190 amino acid HBc chimera having (NANP)$_4$ inserted between amino acids 78 and 79 of HBc, (flanked by the Gly-Ile and Glu-Leu sequences derived from the EcoRI and SacI restriction sites respectively) and the C17A version of the Pf/CS-UTC at the C terminus. The single cysteine was therefore located between V149 of HBc and the Gly-Ile linker sequence (derived from the EcoRI restriction site) located prior to the first amino acids of the Pf/CS-UTC(C17A) T cell epitope (see SEQ ID NO:167).

This hybrid particle was expressed, purified and analyzed for stability by incubating at 37° C. for several weeks. The stability of this particle (V12.Pf1(C17A)C150) was compared to V12.Pf1, with the only difference between the two particles being the position of the cysteine residue. For V12.Pf1 the cysteine is followed by 3 amino acids (SVT) at the C-terminus of the protein (SEQ ID No: 166), whereas for V12.Pf1(C17A)C150 the cysteine is followed by 22 additional amino acid residues (SEQ ID No: 167).

```
V12.Pf1
    TTVV   GI EYLNKIQNSLSTEWSPCSVT    SEQ ID No:166

V12.Pf1(C17A)C150
    TTVV C GI EYLNKIQNSLSTEWSPASVT     SEQ ID No:167
```

The effect of inserting the cysteine residue between HBc and the T cell epitope (V12.Pf1(C17A)C150) was to create a particle that was significantly more stable than a similar particle without the C terminal cysteine (V12.Pf1(C17A)). This was evident from the fact that unlike V12.Pf1(C17A), V12.Pf1(C17A)C150 could be easily purified without a significant degree of degradation of monomers (compare T=O for these particles in FIGS. 4 and 7); and further, V12.Pf1(C17A)C150 was significantly more stable than V12.Pf1(C17A) following incubation at 37° C. After 14 days at 37° C., V12.Pf1(C17A) monomers are totally degraded (FIG. 4), whereas V12.Pf1(C17A)C150 monomers are only partially degraded (FIG. 7).

It was apparent that V12.Pf1(C17A)C150 was not as stable V12.Pf1 (FIG. 7). These data indicate that the stabilizing effects of a single C-terminal cysteine residue are most effective when placed at or near, e.g. within five residues of, the C-terminus of the HBc chimer.

EXAMPLE 14

Preparation of Vectors to Express Particles with a Cysteine Residue at the C-Terminus of a Fused Epitope To further investigate whether terminal cysteine residues could elicit stabilizing effects at positions other than 150, a Th epitope from the hepatitis B core protein (amino acid residues 74–87) was fused to the C-terminus of HBc containing a malarial epitope [(NANP)$_4$] in the immunodominant loop. This Th epitope does not contain a cysteine residue, so a Cys residue was added at the C-terminus (underlined "C"). The control contained the same fused epitope lacking the cysteine.

These particles were made by combining V2.Pf1 with V7.HBc74–87 (and V7.HBc74–87+C) to form the desired vector. The V7 construct was PCR amplified with the HBc-P79/SacI-F primer (SEQ ID NO: 35) and pKK223-2/4515-32-R (SEQ ID NO:36). The product was cut with SacI and HindIII, and the SacI/HindIII fragment was ligated into V2.Pf1 cut with the same enzymes.

Table 14, below, shows the amino acid sequences of C-terminal fusions HBc(74–87) and HBc(74–87)+C, relative to the native sequence that occurs in the wild type HBc protein, as well as the and the HBc149+C particle. "Cys shift" is the position of the introduced cysteine relative to its location in the wild type protein, where it is the last residue (position 183).

TABLE 14

| Source | Sequence | PI | Length | Cys Position | Cys Shift |
| --- | --- | --- | --- | --- | --- |
| Native | RRRGSPRRRT-PSPRRRRSQSP-RRRRSQSRESQC SEQ ID NO: 147 | 12.74 | 34 | 34 | Zero |
| HBc (74–87) | GIVNLEDPAS-RDLVVS SEQ ID NO: 182 | 3.78 | 16 | N/A | N/A |
| HBc (74–87) + C | GIVNLEDPAS-RDLVVSC SEQ ID NO: 183 | 3.78 | 16 | 16 | −17 |
| HBc-149 + C | C | N/A | 1 | 1 | −33 |

EXAMPLE 15

Comparative Immunogenicities in Monkeys

The comparative immunogenicity of the particles expressed by V12.Pf3.1, formulated with either Seppic™ ISA-720 (Seppic Inc., Paris, France), Alhydrogel™ (Superfos, Denmark) as adjuvants, or unformulated (saline), was studied in Cynomolgus monkeys.

The Seppic™ ISA-720 formulation was prepared according to the manufacturers directions. Briefly, the ISA-720 and V12.Pf3.1 particles were mixed at 70:30 (w/w) ratio and vortexed, using a bench top vortexer, set at maximum power, for 1 minute. The Alhydrogel™ formulation was prepared using an 8-fold excess of Alhydrogel™ (by weight) over V12.Pf3.1 particles, which was shown to be physically bound to the Alhydrogel™ prior to immunization.

Groups of two monkeys (one male and one female) were immunized with 20 μg V12.Pf3.1 particles as immunogen via the intramuscular route. Animals were bled on days 0, 21, 42, 56 and 70, and sera analyzed for titers of anti-NANP antibody using an ELISA. The results, shown in Table 15, below, demonstrate the extremely high immunogenicity of V12.Pf3.1 particles when formulated with Seppic™ ISA-720 versus Alhydrogel™-formulated or unformulated material. The kinetics of the antibody response were more rapid when Seppic™ ISA-720 was used as the adjuvant, and the end-point titers were more than 100- and 1000-fold higher than for Alhydrogel™ and saline respectively.

TABLE 15

| | Antibody Titers at Stated Time (Days) | | | | |
|---|---|---|---|---|---|
| Adjuvant | Zero | 21 | 42 | 56 | 70 |
| Saline | Zero | 40 | 240 | 1,200 | 640 |
| Anhydrogel ™ | Zero | 2,880 | 1920 | 11,500 | 6400 |
| Seppic ™ ISA-720 | Zero | 81,920 | 348,160 | 26,000,000 | 1,920,000 |

EXAMPLE 16

T Cell Activation

Mice were immunized twice with V12.Pf3.1 particles in Seppic™ Montanide™ ISA-720. Spleen cells were removed and stimulated in the presence of various peptides. $10^6$ cells were incubated for 3 days in the presence of peptides: UTC (universal T epitope from *P. falciparum*; SEQ IN NO: 120), p85–100 peptide corresponding to HBc 85–100, NANP (B-cell epitope from V12.Pf3.1; NANPNVDP(NANP)$_3$, SEQ ID NO:22) in the presence of Staphylococcal enterotoxin B (SEB), or tissue culture medium (unstim). Interferon gamma production after 3 days was determined by ELISA.

The results shown in Table 16, below, indicate that immunizing with V12.Pf3.1 induces T-cells that recognize the UTC component of the protein, and drives them to a Th1 type response.

TABLE 16

| Immunogen | IFN-γ (pg/ml) | S.D.* |
|---|---|---|
| UTC | 1600 | 750 |
| p85-100 | 350 | 30 |
| NANPNVDP(NANP)$_3$ SEQ ID NO: 22 | 370 | 50 |
| SEB | 4300 | ND** |
| unstim | 900 | 1100 |

*S.D. = Standard Deviation
**ND = Not Done

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A recombinant hepatitis B virus core (HBc) protein chimer molecule with a length of about 140 to about 310 amino acid residues that contains four peptide-linked amino acid residue sequence domains from the N-terminus that are denominated Domains I, II, III and IV, wherein (a) Domain I comprises (i) the sequence from position 1 through position 75 of HBc, or (ii) a sequence of about 85 amino acids comprising a sequence heterologous to HBc peptide-bonded to one of the first five N-terminal residues of HBc, and including at least the sequence of the residues of position 5 through position 75 of HBc.

(b) Domain II comprises about 18 to about 58 amino acid residues peptide-bonded to residue 75 of HBc, including (i) the sequence of positions 76 through 85 of HBc, and (ii) a sequence of 8 to about 48 residues that constitute a B cell epitope of the circumsporozoite (CS) protein of the parasite *Plasmodium falciparum* that is peptide-bonded between the HBc residues of positions 78 and 79, said B cell epitope being comprised of two to about five repeats of the amino acid residue sequence Asn-Ala-Asn-Pro;

(c) Domain III is an HBc sequence from position 86 through position 135 peptide-bonded to residue 85; and (d) Domain IV comprises a sequence of HBC from residue 136 through 140 peptide-bonded to the residue of position 135 of Domain III and (i) zero to nine residues of a HBc amino acid residue sequence from position 141 through 149, (ii) zero to three cysteine residue, (iii) fewer than three arginine or lysine residue, or mixtures thereof adjacent to each other, and (iv) up to 100 amino acid residues in a sequence heterologous to HBc from position 150 to the C-terminus, with the proviso that at least five amino acid residue are present of the amino acid residue sequence from position 136 through 149, when (a) zero cysteine residues are present and (b) fewer than about five heterologous amino acid residues are present, and wherein no more than 10 percent of the HBc amino acid residues are substituted as compared to SEQ ID NO:170 from position 1 through 149.

2. The recombinant HBc chimer protein molecule according to claim 1 present as self-assembled particles.

3. The recombinant HBc chimer protein molecule according to claim 1 wherein Domain I consists essentially of the HBc sequence from position 1 through position 75.

4. The recombinant HBc chimer protein molecule according to claim 1 wherein Domain II independently includes zero to three peptide-bonded residues on either side of said B cell epitope that are other than those of HBc or said B cell epitope.

5. The recombinant HBc chimer protein molecule according to claim 1 wherein said sequence heterologous to HBc at position 150 to the C-terminus of Domain IV comprises an amino acid residue sequence that constitutes a T cell epitope of the same species of *Plasmodium* as said B cell epitope.

6. A recombinant hepatitis B virus core (HBc) protein chimer molecule with a sequence of about 155 to about 235 amino acid residues that contains four peptide-linked domains from the N-terminus that are denominated Domains I, II, III and IV, wherein (a) Domain I comprises a sequence of residues 1 through 75 of HBc;

(b) Domain II comprises about 18 to about 46 amino acid residues peptide-bonded to residue 75 of HBc, including (i) the sequence of positions 76 through 85 of HBc, and (ii) a sequence of 8 to about 36 residues that constitute a repeated B cell epitope of the circumsporozoite (CS) protein of *Plasmodium falciparum* of the sequence Asn-Ala-Asn-Pro that is peptide-bonded between the residues of positions 78 and 79, said B cell epitope being comprised of two to about five repeats of an amino acid residue sequence, said Domain independently including zero to three peptide-bonded residues on either side of said B cell epitope that are other than those of HBc or said B cell epitope;

(c) Domain III comprises the HBc sequence from position 86 through position 135; and (d) Domain IV comprises a sequence of HBc from residue 136 through 140 peptide-bonded to the residue of position 135 of Domain III and (i) zero to nine residues of a HBc amino acid residue sequence from position 141 through 149, (ii) one to three cysteine residues, (iii) fewer than three arginine or lysine residues, or mixtures thereof adjacent to each other, and (iv) up to 50 amino acid residues in a sequence that constitutes a T cell epitope of *Plasmodium falciparum* peptide-bonded to the final HBc amino acid residue present in the chimer, and wherein no more then 10 percent of the HBc amino acid residues are substituted as compared to SEQ ID NO:170 from position 1 through 149.

7. The recombinant HBc chimer protein molecule according to claim 6 wherein Domain IV comprises one amino acid residue to a sequence of about nine amino acid residues of the HBc sequence from residue position 141 through about position 149 peptide-bonded to residue 140.

8. The recombinant HBc chimer protein molecule according to claim 7 wherein Domain IV consists essentially of a sequence of nine amino acid residues of the HBc sequence from residue position 141 through position 149 peptide-bonded to residue 140.

9. The recombinant HBc chimer protein molecule according to claim 7 wherein said one to three cysteine residues are present in Domain IV within about 30 residues of the carboxy-terminus of the chimeric molecule.

10. The recombinant HBc chimer protein molecule according to claim 9 wherein said one to three cysteine residues are present in said T cell epitope.

11. The recombinant HBc chimer protein molecule according to claim 10 wherein said T cell epitope is present and has the sequence of SEQ ID NO: 148 or 24 (EYLNKIQNSLSTEWSPCSVT OR GIEYLNKIQNSLSTEWSPCSVT).

12. The recombinant HBc chimer protein molecule according to claim 6 wherein the repeated sequence of said B cell epitope of Domain II is repeated three or four times.

13. The recombinant HBc chimer protein molecule according to claim 12 wherein the repeated sequences are peptide-bonded to each other without interruption.

14. The recombinant HBc chimer protein molecule according to claim 13 wherein said B cell epitope includes a second CS protein sequence from *Plasmodium falciparum* that is peptide-bonded to said repeated sequence.

15. The recombinant HBc chimer protein molecule according to claim 14 wherein said second CS protein sequence is Asn-Val-ABp-Pro.

16. The recombinant HBc chimer protein molecule according to claim 15 wherein said second CS protein sequence is peptide-bonded at the amino-terminus of said repeated sequence.

17. The recombinant HBc chimer protein molecule according to claim 14 wherein said second CS protein sequence ID SEQ ID NO:126 (Asn-Ala-Asn-Pro-Asn-Val-Asp-Pro).

18. The recombinant HBc chimer protein molecule according to claim 17 wherein said second CS protein sequence is peptide-bonded at the amino-terminus of said repeated sequence.

19. The recombinant HBc chimer protein molecule according to claim 6 present as self-assembled particles.

20. Particles comprised of recombinant hepatitis B virus core (HBc) protein chimer molecules, said molecules having a sequence of about 155 to about 235 amino acid residues that contains four peptide-linked amino acid residue sequence domains from the N-terminus that are denominated Domains I, II, III and IV, wherein
(a) Domain I comprises (i) the sequence from position 1 through position 75 of HBc, or (ii) a sequence of about 85 amino acids comprising a sequence heterologous to HBc peptide-bonded to one of the first five N-terminal residues of HBc, and including at least the sequence of the residues of position 5 through position 75 of HBc;
(b) Domain II comprises about 18 to about 58 amino acid residues peptide-bonded to residue 75 of HBc, including (i) the sequence of positions 76 through 85 of HBc, and (ii) a sequence of 8 to about 48 residue. that constitute a B cell epitope of the circumsporozoite (CS) protein of the parasite *Plasmodium falciparum* that is peptide-bonded between the HBc residues of positions 78 and 79, said B cell epitope being comprised of two to about five repeats of an amino acid residue sequence Asn-Ala-Asn-Pro;
(c) Domain III is an HBc sequence from position 86 through position 135 peptide-bonded to residue 85; and
(d) Domain IV comprises a sequence of HBc from residue 136 through 140 peptide-bonded to the residue of position 135 of Domain III, and (i) zero to nine residues of a HBc amino acid residue sequence from position 141 through 149, (ii) zero to three cysteine residues, (iii) fewer than three arginine or lysine residues, or mixtures thereof adjacent to each other, and (iv) up to 50 amino acid residues in a sequence heterologous to HBc from position 150 to the C-terminus, and
wherein no more than 10 percent of the HBc amino acid residues are substituted as compared to SEQ ID NO:170 from position 1 through 149.

21. The particles according to claim 20 whose HBc chimer protein molecules have a sequence length of about 165 to about 210 amino acid residues.

22. The particles according to claim 20 wherein Domain I consists essentially of the HBc sequence from position 1 through position 75.

23. The particles according to claim 20 wherein Domain II independently includes zero to three peptide-bonded residues on either side of said B call epitope that are other than those of HBc or said B cell epitope.

24. The particles according to claim 20 wherein maid sequence heterologous to HBc at position 150 to the C-terminus of Domain IV comprises an amino acid residue sequence that constitutes a T cell epitope of *Plasmodium falciparum*.

25. Particles comprised of recombinant hepatitis B virus core (HBc) protein chimer molecules, said molecules having a sequence of about 165 to about 210 amino acid residues that contains four peptide-linked amino acid residue sequence domains from the N-terminus that are denominated Domains I, II, III and IV, wherein
(a) Domain I comprises a sequence of residues 1 through position 75 of HBc;
(b) Domain II comprises about 18 to about 46 amino acid residues peptide-bonded to residue 75 of HBc, including (i) the sequence of positions 76 through 85 of HBc, and (ii) a sequence of 8 to about 36 residues that constitute a B cell epitope of the circumsporozoite (CS) protein of *Plasmodium falciparum* that is peptide-bonded between the residues of HBc positions 78 and 79, said B cell epitope being comprised of two to about five repeats of the amino acid residue sequence Asn-Ala-Asn-Pro, said Domain independently including zero to two peptide-bonded residues on either side of said B cell epitope that are other than those of HBc or said B cell epitope;
(c) Domain III is an HBc sequence from position 86 through position 135 peptide-bonded to residue 85; and
(d) Domain IV comprises the HBc sequence of residues 136 through 140 peptide-bonded to the residue of position 135 of Domain III and (i) zero to nine residues of a HBc amino acid residue sequence from position 140 through 149 peptide-bonded to the residue of position 140, (ii) one to three cysteine residues, (iii) fewer than three arginine or lysine residues, or mixtures thereof adjacent to each other, and (iv) up to 25 amino acid residues in a sequence that constitutes a T cell epitope of the same species of *Plasmodium* as said B cell epitope, said T cell epitope sequence being peptide-bonded to the final HBc amino acid residue present in a chimer molecule or a cysteine residue, and
wherein no more than 10 percent of the HBc amino acid residues are substituted as compared to SEQ ID NO:170 from position 1 through 149.

26. The particles according to claim 25 wherein Domain IV comprises one to a sequence of nine amino acid residues of the HBc sequence from residue position 141 through position 149 linked between residue 140 of said Domain III sequence and a *Plasmodium falciparum* T cell epitope.

27. The particles according to claim 26 wherein the nine amino acid residues of the HBc sequence from residue position 141 through position 149 are present.

28. The particles according to claim 26 wherein said one to three cysteine residues in the Domain IV sequence are present within about 30 residues of the carboxy-terminus of the chimeric molecule.

29. The particles according to claim 28 having one cysteine residue in the Domain IV sequence.

30. The particles according to claim 25 wherein the repeated sequence of said B cell epitope of Domain II is repeated three or four times.

31. The particles according to claim 30 wherein the repeated sequences are peptide-bonded to each other without interruption.

32. The particles according to claim 31 wherein said B cell epitope includes a second CS protein sequence from *Plasmodium falciparum* that is peptide-bonded to said repeated sequence.

33. The particles according to claim 32 wherein said second CS protein sequence is Asn-Val-Asp-Pro.

34. The particles according to claim 33 wherein said second CS protein sequence is peptide-bonded at the amino-terminus of said repeated sequence.

35. The particles according to claim 33 wherein said second CS protein sequence is peptide-bonded at the carboxy-terminus of said repeated sequence.

36. The particles according to claim 32 wherein said second CS protein sequence in SEQ ID NO:126 (Asn-Ala-Asn-Pro-Asn-Val-Asp-Pro).

37. The particles according to claim 36 wherein said second CS protein sequence is peptide-bonded at the amino-terminus of said repeated sequence.

38. The particles according to claim 36 wherein said second CS protein sequence is a peptide-bonded at the carboxy-terminus of said repeated sequence.

39. The particle, according to claim 25 wherein said B cell epitope of *Plasmodium falciparum* has an amino acid residue sequence selected from the group consisting of SEQ ID NOs:1–14.

40. The particles according to claim 25 wherein said T cell epitope of *Plasmodium falciparum* is present and has the amino acid residue sequence of SEQ ID NO:24.

41. Particles comprised of recombinant hepatitis B virus core (HBc) protein chimer molecules, said molecules having a sequence of about 165 to about 210 amino acid residues that contain four peptide-linked domains from the N-terminus that are denominated Domains I, II, III and IV, wherein
    (a) Domain I comprises a sequences of residues 1 through position 75 of HBc;
    (b) Domain II comprises about 18 to about 46 amino acid residues peptide-bonded to residue 75 of HBc, including (i) the sequence of positions 76 through 85 of HBc, and (ii) a sequence that constitutes a B cell epitope of the circumsporozoite (CS) protein of *Plasmodium falciparum* is peptide-bonded between the residues of HBc positions 78 and 79, said B cell epitope being selected from the group consisting of SEQ ID NOs; 1–14, said Domain II including two peptide-bonded residues on either side of said B cell epitope that are other than those of HBc or said B cell epitope,
    (c) Domain III is an HBc sequence from position 86 through position 135 peptide bonded to residue 85; and
    (d) Domain IV comprises the sequence of HBc residues 136–140 peptide-bonded to residue 135 plus one to nine residues of a HBc amino acid residue sequence from position 141 through 149 peptide-bonded to the residue of position 140 and also peptide-bonded to a *Plasmodium falciparum* T cell epitope of a sequence of up to about 25 amino acid residues that includes a cysteine residue, and
    wherein no more than 10 percent of the HBc amino acid residues are substituted as compared to SEQ ID NO:170 from position 1 through 149.

42. The particles according to claim 41 wherein Domain IV comprises nine amino acid residues of the HBc sequence from residue position 141 through position 149 bonded between said residue 140 and said *Plasmodium falciparum* T cell epitope.

43. The particles according to claim 42 wherein said *Plasmodium falciparum* T cell epitope has the amino acid sequence of SEQ ID NO:24.

44. A vaccine or inoculum comprising an immunogenic effective amount immunogenic particles dissolved or dispersed in a pharmaceutically acceptable diluent, wherein said immunogenic particles are comprised of a plurality of recombinant chimeric hepatitis B core (HBc) protein molecules having a length of about 140 to about 310 amino acid residues that contain four peptide-linked amino acid residue sequence domains from the N-terminus that are denominated Domains I, II, III and IV, wherein
    (a) Domain I comprises (i) the sequence from position 1 through position 75 of HBc, or (ii) a sequence of about 85 amino acids comprising a sequence heterologous to HBc peptide-bonded to one of the first five N-terminal residues of HBc, and including at least the sequence of the residues of position 5 through position 75 of HBc;
    (b) Domain II comprises about 18 to about 58 amino acid residues peptide-bonded to residue 75 of HBc, including (i) the sequence of positions 76 through 85 of HBc, and (ii) a sequence of 8 to about 48 residues that constitute a B cell epitope of the circumsporozoite (CS) protein of the parasite *Plasmodium falciparum* that is peptide-bonded between the HBc residues of positions 78 and 79, said B cell epitope being comprised of two to about five repeats of the amino acid residue sequence Asn-Ala-Asn-Pro;
    (a) Domain III is an NBC sequence from position 86 through position 135 peptide-bonded to residue 85; and
    (d) Domain IV comprises a sequence of HBc from residue 136 through 140 peptide-bonded to the residue of position 135 of Domain III and (i) zero to nine residues of a HBc amino acid residue sequence from position 141 through 149, (ii) zero to three cysteine residues, (iii) fewer than three arginine or lysine residues, or mixtures thereof adjacent to each other, and (iv) up to 100 amino acid residues in a sequence heterologous to HBc from position 150 to the C-terminus, and
    wherein no more than 10 percent of the HBc amino acid residues are substituted am compared to SEQ ID NO:170 from position 1 through 149.

45. The vaccine or inoculum according to claim 44 wherein said immunogenic particle, are those having a sequence of about 165 to about 210 amino acid residues that contains four peptide-linked amino acid residue sequence domains from the N-terminus that are denominated Domains I, II, III and IV, wherein
    (a) Domain I comprises a Sequence of residues 1 through position 75 of HBc;
    (b) Domain II comprises about 18 to about 46 amino acid residues peptide-bonded to residue 75 of HBc, including (I) the sequence of positions 76 through 85 of HBc, and (ii) a sequence of 8 to about 36 residues that constitute a B cell epitope of the circumsporozoite (CS) protein of *Plasmodium falciparum* that is peptide-bonded between the residues of HBc positions 78 and 79, said B cell epitope being comprised of two to about five repeats of the amino acid residue sequence Asn-Ala-Asn-Pro, said Domain independently including zero to two peptide-bonded residues on either side of said B cell epitope that are other than those of HBc or said B cell epitope;
    (c) Domain III is an HBc sequence from position 86 through position 135 peptide-bonded to residue 85; and
    (d) Domain IV comprises the NBC sequence of residues 136 through 140 peptide-bonded to the residue of position 135 of Domain III and (i) nine residues of a HBc amino acid residue sequence from position 141 through 149 peptide-bonded to the residue of position 140, (ii) one to three cysteine residues, (iii) fewer than three arginine or lysine residues, or mixtures thereof adjacent to each other, and (iv) a *Plasmodium falciparum* T cell epitope, said T cell epitope sequence being peptide-bonded to the final HBc amino acid residue present in a chimer molecule or a cysteine residue, and wherein no more than 5 percent of the HBc amino acid residues are substituted as compared to SEQ ID NO:170 from position 1 through 149.

46. The vaccine or inoculum according to claim 44 wherein Domain II comprises about 18 to about 46 amino acid residues peptide-bonded to residue 75 of HBc, including (i) the sequence of positions 76 through 85 of HBc, and (ii) a sequence of 8 to about 36 residues that constitute a B cell epitope of the circumsporozoite (CS) protein of *Plasmodium falciparum* that is peptide-bonded between the residues of HBc positions 78 and 79, said B cell epitope being comprised of three or four repeats of an amino acid residue sequence Asn-Ala-Asn-Pro, said Domain independently including zero to two peptide-bonded residues on either side of said B cell epitope that are other than those of HBc or said B cell epitope.

47. The vaccine or inoculum according to claim 46 wherein the repeated sequences are peptide-bonded to each other without interruption and wherein said B cell epitope includes a second CS protein sequence from *Plasmodium falciparum* that is peptide-bonded to said repeated sequence.

48. The vaccine or inoculum according to claim 44 wherein said immunogenic particles are those comprised of recombinant hepatitis B virus core (HBc) protein chimer molecules, said molecules having a sequence of about 165 to about 210 amino acid residues that contain four peptide-linked domains from the N-terminus that are denominated Domains I, II, III and IV, wherein (a) Domain I comprises a sequence of residues 1 through position 75 of HBc, (b) Domain II comprises about 18 to about 46 amino acid residues peptide-bonded to residue 75 of HBc, including (i) the sequence of positions 76 through 85 of HBc, and (ii) a sequence that constitutes a B cell epitope of the circumsporozoite (CS) protein of *Plasmodium falciparum* is peptide-bonded between the residues of HBc positions 78 and 79, said B cell epitope being selected from the group consisting of SEQ ID NOs:1–14, said Domain II including two peptide-bonded residues on either side of said B cell epitope that are other than those of HBc or said B cell epitope;

(c) Domain III is an HBc sequence from position 86 through position 135 peptide bonded to residue 85; and (d) Domain IV comprises the sequence of HBc residues 136–140 peptide-bonded to residue 135 plus nine residues of a HBc amino acid residue sequence from position 142 through 149 peptide-bonded to the residue of position 140 and also peptide-bonded to a *Plasmodium falciparum* T cell epitope of a sequence of up to about 25 amino acid residues that includes a cysteine residue, and wherein no more than 5 percent of the HBc amino acid residues are substituted as compared to SEQ ID NO:170 from position 1 through 149.

49. The vaccine or inoculum according to claim 48 wherein said immunogenic particles are those wherein said *Plasmodium falciparum* T cell epitope has the amino acid sequence of SEQ ID NO:24.

50. The vaccine or inoculum according to claim 44 that is adapted for parenteral administration.

* * * * *

SEQUENCE LISTING

```
<160> NUMBER OF SEQ ID NOS: 186

<210> SEQ ID NO 1
<211> LENGTH: 16
<212> TYPE: PRT
<213> ORGANISM: Plasmodium falciparum

<400> SEQUENCE: 1

Asn Ala Asn Pro Asn Ala Asn Pro Asn Ala Asn Pro Asn Ala Asn Pro
 1               5                  10                  15

<210> SEQ ID NO 2
<211> LENGTH: 24
<212> TYPE: PRT
<213> ORGANISM: Plasmodium falciparum

<400> SEQUENCE: 2

Asn Ala Asn Pro Asn Val Asp Pro Asn Ala Asn Pro Asn Ala Asn Pro
 1               5                  10                  15

Asn Ala Asn Pro Asn Val Asp Pro
            20

<210> SEQ ID NO 3
<211> LENGTH: 20
<212> TYPE: PRT
<213> ORGANISM: Plasmodium falciparum

<400> SEQUENCE: 3

Asn Ala Asn Pro Asn Val Asp Pro Asn Ala Asn Pro Asn Ala Asn Pro
 1               5                  10                  15
```

Asn Ala Asn Pro
        20

<210> SEQ ID NO 4
<211> LENGTH: 20
<212> TYPE: PRT
<213> ORGANISM: Plasmodium falciparum

<400> SEQUENCE: 4

Asn Ala Asn Pro Asn Ala Asn Pro Asn Ala Asn Pro Asn Val Asp Pro
1               5                   10                  15

Asn Ala Asn Pro
        20

<210> SEQ ID NO 5
<211> LENGTH: 28
<212> TYPE: PRT
<213> ORGANISM: Plasmodium falciparum

<400> SEQUENCE: 5

Asn Ala Asn Pro Asn Val Asp Pro Asn Ala Asn Pro Asn Ala Asn Pro
1               5                   10                  15

Asn Ala Asn Pro Asn Val Asp Pro Asn Ala Asn Pro
            20                  25

<210> SEQ ID NO 6
<211> LENGTH: 20
<212> TYPE: PRT
<213> ORGANISM: Plasmodium falciparum

<400> SEQUENCE: 6

Asn Pro Asn Val Asp Pro Asn Ala Asn Pro Asn Ala Asn Pro Asn Ala
1               5                   10                  15

Asn Pro Asn Val
        20

<210> SEQ ID NO 7
<211> LENGTH: 22
<212> TYPE: PRT
<213> ORGANISM: Plasmodium falciparum

<400> SEQUENCE: 7

Asn Pro Asn Val Asp Pro Asn Ala Asn Pro Asn Ala Asn Pro Asn Ala
1               5                   10                  15

Asn Pro Asn Val Asp Pro
        20

<210> SEQ ID NO 8
<211> LENGTH: 24
<212> TYPE: PRT
<213> ORGANISM: Plasmodium falciparum

<400> SEQUENCE: 8

Asn Pro Asn Val Asp Pro Asn Ala Asn Pro Asn Ala Asn Pro Asn Ala
1               5                   10                  15

Asn Pro Asn Val Asp Pro Asn Ala
        20

<210> SEQ ID NO 9
<211> LENGTH: 18
<212> TYPE: PRT
<213> ORGANISM: Plasmodium falciparum

```
<400> SEQUENCE: 9

Asn Val Asp Pro Asn Ala Asn Pro Asn Ala Asn Pro Asn Ala Asn Pro
 1               5                  10                  15

Asn Val

<210> SEQ ID NO 10
<211> LENGTH: 20
<212> TYPE: PRT
<213> ORGANISM: Plasmodium falciparum

<400> SEQUENCE: 10

Asn Val Asp Pro Asn Ala Asn Pro Asn Ala Asn Pro Asn Ala Asn Pro
 1               5                  10                  15

Asn Val Asp Pro
            20

<210> SEQ ID NO 11
<211> LENGTH: 22
<212> TYPE: PRT
<213> ORGANISM: Plasmodium falciparum

<400> SEQUENCE: 11

Asn Val Asp Pro Asn Ala Asn Pro Asn Ala Asn Pro Asn Ala Asn Pro
 1               5                  10                  15

Asn Val Asp Pro Asn Ala
            20

<210> SEQ ID NO 12
<211> LENGTH: 16
<212> TYPE: PRT
<213> ORGANISM: Plasmodium falciparum

<400> SEQUENCE: 12

Asp Pro Asn Ala Asn Pro Asn Ala Asn Pro Asn Ala Asn Pro Asn Val
 1               5                  10                  15

<210> SEQ ID NO 13
<211> LENGTH: 18
<212> TYPE: PRT
<213> ORGANISM: Plasmodium falciparum

<400> SEQUENCE: 13

Asp Pro Asn Ala Asn Pro Asn Ala Asn Pro Asn Ala Asn Pro Asn Val
 1               5                  10                  15

Asp Pro

<210> SEQ ID NO 14
<211> LENGTH: 20
<212> TYPE: PRT
<213> ORGANISM: Plasmodium falciparum

<400> SEQUENCE: 14

Asp Pro Asn Ala Asn Pro Asn Ala Asn Pro Asn Ala Asn Pro Asn Val
 1               5                  10                  15

Asp Pro Asn Ala
            20

<210> SEQ ID NO 15
<211> LENGTH: 18
<212> TYPE: PRT
<213> ORGANISM: Plasmodium vivax
```

-continued

```
<400> SEQUENCE: 15

Asp Arg Ala Ala Gly Gln Pro Ala Gly Asp Arg Ala Asp Gly Gln Pro
1               5                   10                  15
Ala Gly

<210> SEQ ID NO 16
<211> LENGTH: 36
<212> TYPE: PRT
<213> ORGANISM: Plasmodium vivax

<400> SEQUENCE: 16

Ala Asn Gly Ala Gly Asn Gln Pro Gly Ala Asn Gly Ala Gly Asp Gln
1               5                   10                  15
Pro Gly Ala Asn Gly Ala Asp Asn Gln Pro Gly Ala Asn Gly Ala Asp
            20                  25                  30
Asp Gln Pro Gly
        35

<210> SEQ ID NO 17
<211> LENGTH: 18
<212> TYPE: PRT
<213> ORGANISM: Plasmodium vivax

<400> SEQUENCE: 17

Ala Asn Gly Ala Gly Asn Gln Pro Gly Ala Asn Gly Ala Gly Asp Gln
1               5                   10                  15
Pro Gly

<210> SEQ ID NO 18
<211> LENGTH: 18
<212> TYPE: PRT
<213> ORGANISM: Plasmodium vivax

<400> SEQUENCE: 18

Ala Asn Gly Ala Asp Asn Gln Pro Gly Ala Asn Gly Ala Asp Asp Gln
1               5                   10                  15
Pro Gly

<210> SEQ ID NO 19
<211> LENGTH: 18
<212> TYPE: PRT
<213> ORGANISM: Plasmodium vivax

<400> SEQUENCE: 19

Ala Asn Gly Ala Gly Asn Gln Pro Gly Ala Asn Gly Ala Asp Asn Gln
1               5                   10                  15
Pro Gly

<210> SEQ ID NO 20
<211> LENGTH: 18
<212> TYPE: PRT
<213> ORGANISM: Plasmodium vivax

<400> SEQUENCE: 20

Ala Asn Gly Ala Asp Asn Gln Pro Gly Ala Asn Gly Ala Asp Asp Gln
1               5                   10                  15
Pro Gly

<210> SEQ ID NO 21
<211> LENGTH: 22
```

```
<212> TYPE: PRT
<213> ORGANISM: Plasmodium vivax

<400> SEQUENCE: 21

Ala Pro Gly Ala Asn Gln Glu Gly Gly Ala Ala Pro Gly Ala Asn
  1               5                  10                  15

Gln Glu Gly Gly Ala Ala
            20

<210> SEQ ID NO 22
<211> LENGTH: 16
<212> TYPE: PRT
<213> ORGANISM: Plasmodium berghei

<400> SEQUENCE: 22

Asp Pro Pro Pro Pro Asn Pro Asn Asp Pro Pro Pro Asn Pro Asn
  1               5                  10                  15

<210> SEQ ID NO 23
<211> LENGTH: 24
<212> TYPE: PRT
<213> ORGANISM: Plasmodium yoelii

<400> SEQUENCE: 23

Gln Gly Pro Gly Ala Pro Gln Gly Pro Gly Ala Pro Gln Gly Pro Gly
  1               5                  10                  15

Ala Pro Gln Gly Pro Gly Ala Pro
            20

<210> SEQ ID NO 24
<211> LENGTH: 22
<212> TYPE: PRT
<213> ORGANISM: Plasmodium falciparum

<400> SEQUENCE: 24

Gly Ile Glu Tyr Leu Asn Lys Ile Gln Asn Ser Leu Ser Thr Glu Trp
  1               5                  10                  15

Ser Pro Cys Ser Val Thr
            20

<210> SEQ ID NO 25
<211> LENGTH: 19
<212> TYPE: PRT
<213> ORGANISM: Plasmodium vivax

<400> SEQUENCE: 25

Tyr Leu Asp Lys Val Arg Ala Thr Val Gly Thr Glu Trp Thr Pro Cys
  1               5                  10                  15

Ser Val Thr

<210> SEQ ID NO 26
<211> LENGTH: 20
<212> TYPE: PRT
<213> ORGANISM: Plasmodium yoelii

<400> SEQUENCE: 26

Glu Phe Val Lys Gln Ile Ser Ser Gln Leu Thr Glu Glu Trp Ser Gln
  1               5                  10                  15

Cys Ser Val Thr
            20

<210> SEQ ID NO 27
```

```
<211> LENGTH: 18
<212> TYPE: DNA
<213> ORGANISM: Artificial Sequence
<220> FEATURE:
<223> OTHER INFORMATION: Description of Artificial Sequence: plasmid
      pkk223

<400> SEQUENCE: 27
ggtgcatgca aggagatg                                              18

<210> SEQ ID NO 28
<211> LENGTH: 55
<212> TYPE: DNA
<213> ORGANISM: Artificial Sequence
<220> FEATURE:
<223> OTHER INFORMATION: Description of Artificial Sequence:pKK223

<400> SEQUENCE: 28
gcgaagcttc ggatcccatg gttttttcct ccttatgtga aattgttatc cgctc      55

<210> SEQ ID NO 29
<211> LENGTH: 24
<212> TYPE: DNA
<213> ORGANISM: Hepatitis B virus

<400> SEQUENCE: 29
ttgggccatg gacatcgacc ctta                                        24

<210> SEQ ID NO 30
<211> LENGTH: 29
<212> TYPE: DNA
<213> ORGANISM: Hepatitis B virus

<400> SEQUENCE: 30
gcggaattcc ttccaaatta acacccacc                                   29

<210> SEQ ID NO 31
<211> LENGTH: 38
<212> TYPE: DNA
<213> ORGANISM: Hepatitis B virus

<400> SEQUENCE: 31
cgcgaattca aaagagctc gatccagcgt ctagagac                          38

<210> SEQ ID NO 32
<211> LENGTH: 31
<212> TYPE: DNA
<213> ORGANISM: Hepatitis B virus

<400> SEQUENCE: 32
cgcaagctta acaacagta gtctccggaa g                                 31

<210> SEQ ID NO 33
<211> LENGTH: 42
<212> TYPE: DNA
<213> ORGANISM: Hepatitis B virus

<400> SEQUENCE: 33
cgcaagctta gagctcttga attccaacaa cagtagtctc cg                    42

<210> SEQ ID NO 34
<211> LENGTH: 39
<212> TYPE: DNA
<213> ORGANISM: Hepatitis B virus
```

<400> SEQUENCE: 34
cgcgaattca aaaagagctc ccagcgtcta gagacctag                                39

<210> SEQ ID NO 35
<211> LENGTH: 28
<212> TYPE: DNA
<213> ORGANISM: Hepatitis B virus

<400> SEQUENCE: 35
cgcgagctcc cagcgtctag agacctag                                           28

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence:pKK223-2

<400> SEQUENCE: 36
gtatcaggct gaaaatc                                                       17

<210> SEQ ID NO 37
<211> LENGTH: 19
<212> TYPE: PRT
<213> ORGANISM: Plasmodium falciparum

<400> SEQUENCE: 37

Ile Asn Ala Asn Pro Asn Ala Asn Pro Asn Ala Asn Pro Asn Ala Asn
 1               5                  10                  15

Pro Glu Leu

<210> SEQ ID NO 38
<211> LENGTH: 57
<212> TYPE: DNA
<213> ORGANISM: Plasmodium falciparum

<400> SEQUENCE: 38
aattaacgct aatccgaacg ctaatccgaa cgctaatccg aacgctaatc cggagct          57

<210> SEQ ID NO 39
<211> LENGTH: 49
<212> TYPE: DNA
<213> ORGANISM: Plasmodium falciparum

<400> SEQUENCE: 39
ccggattagc gttcggatta gcgttcggat tagcgttcgg attagcgtt                   49

<210> SEQ ID NO 40
<211> LENGTH: 31
<212> TYPE: PRT
<213> ORGANISM: Plasmodium falciparum

<400> SEQUENCE: 40

Ile Asn Ala Asn Pro Asn Val Asp Pro Asn Ala Asn Pro Asn Ala Asn
 1               5                  10                  15

Pro Asn Ala Asn Pro Asn Val Asp Pro Asn Ala Asn Pro Glu Leu
                20                  25                  30

<210> SEQ ID NO 41
<211> LENGTH: 93
<212> TYPE: DNA
<213> ORGANISM: Plasmodium falciparum

```
<400> SEQUENCE: 41
aattaacgct aatccgaacg ttgacccgaa cgctaatccg aacgctaatc cgaacgctaa    60
tccgaacgtt gacccgaacg ctaatccgga gct                                 93

<210> SEQ ID NO 42
<211> LENGTH: 91
<212> TYPE: DNA
<213> ORGANISM: Plasmodium falciparum

<400> SEQUENCE: 42
ggagctccgg attagcgttc gggtcaacgt tcggattagc gttcggatta gcgttcggat    60
tagcgttcgg gtcaacgttc ggattagcgt t                                   91

<210> SEQ ID NO 43
<211> LENGTH: 23
<212> TYPE: PRT
<213> ORGANISM: Plasmodium berghei

<400> SEQUENCE: 43

Ile Asn Ala Asn Pro Asn Val Asp Pro Asn Ala Asn Pro Asn Ala Asn
 1               5                  10                  15

Pro Asn Ala Asn Pro Glu Leu
            20

<210> SEQ ID NO 44
<211> LENGTH: 69
<212> TYPE: DNA
<213> ORGANISM: Plasmodium falciparum

<400> SEQUENCE: 44
aattaacgcg aatccgaacg tggatccgaa tgccaaccct aacgccaacc caaatgcgaa    60
cccagagct                                                            69

<210> SEQ ID NO 45
<211> LENGTH: 61
<212> TYPE: DNA
<213> ORGANISM: Plasmodium falciparum

<400> SEQUENCE: 45
ctgggttcgc atttggggttg gcgttagggt tggcattcgg atccacgttc ggattcgcgt    60
t                                                                    61

<210> SEQ ID NO 46
<211> LENGTH: 23
<212> TYPE: PRT
<213> ORGANISM: Plasmodium falciparum

<400> SEQUENCE: 46

Ile Asn Ala Asn Pro Asn Ala Asn Pro Asn Ala Asn Pro Asn Val Asp
 1               5                  10                  15

Pro Asn Ala Asn Pro Glu Leu
            20

<210> SEQ ID NO 47
<211> LENGTH: 69
<212> TYPE: DNA
<213> ORGANISM: Plasmodium falciparum

<400> SEQUENCE: 47
aattaacgcg aatccgaatg ccaaccctaa cgccaaccca acgtggatc cgaatgcgaa    60
```

```
cccagagct                                                              69

<210> SEQ ID NO 48
<211> LENGTH: 61
<212> TYPE: DNA
<213> ORGANISM: Plasmodium falciparum

<400> SEQUENCE: 48
ctgggttcgc attcggatcc acgtttgggt tggcgttagg gttggcattc ggattcgcgt      60
t                                                                      61

<210> SEQ ID NO 49
<211> LENGTH: 31
<212> TYPE: PRT
<213> ORGANISM: Plasmodium falciparum

<400> SEQUENCE: 49

Ile Asn Ala Asn Pro Asn Val Asp Pro Asn Ala Asn Pro Asn Ala Asn
 1               5                  10                  15
Pro Asn Ala Asn Pro Asn Val Asp Pro Asn Ala Asn Pro Glu Leu
             20                  25                  30

<210> SEQ ID NO 50
<211> LENGTH: 93
<212> TYPE: DNA
<213> ORGANISM: Plasmodium falciparum

<400> SEQUENCE: 50
aattaacgcg aatccgaacg tggatccaaa tgccaacccct aacgctaatc caaacgccaa     60
cccgaatgtt gaccccaatg ccaatccgga gct                                   93

<210> SEQ ID NO 51
<211> LENGTH: 85
<212> TYPE: DNA
<213> ORGANISM: Plasmodium falciparum

<400> SEQUENCE: 51
ccggattggc attggggtca acattcgggt tggcgtttgg attagcgtta gggttggcat      60
ttggatccac gttcggattc gcgtt                                            85

<210> SEQ ID NO 52
<211> LENGTH: 23
<212> TYPE: PRT
<213> ORGANISM: Plasmodium falciparum

<400> SEQUENCE: 52

Ile Asn Pro Asn Val Asp Pro Asn Ala Asn Pro Asn Ala Asn Pro Asn
 1               5                  10                  15
Ala Asn Pro Asn Val Glu Leu
             20

<210> SEQ ID NO 53
<211> LENGTH: 69
<212> TYPE: DNA
<213> ORGANISM: Plasmodium falciparum

<400> SEQUENCE: 53
aattaatccg aacgtggatc caaatgccaa ccctaacgct aatccaaacg ccaacccgaa      60
tgttgagct                                                              69
```

<210> SEQ ID NO 54
<211> LENGTH: 61
<212> TYPE: DNA
<213> ORGANISM: Plasmodium falciparum

<400> SEQUENCE: 54
caacattcgg gttggcgttt ggattagcgt tagggttggc atttggatcc acgttcggat    60
t                                                                   61

<210> SEQ ID NO 55
<211> LENGTH: 25
<212> TYPE: PRT
<213> ORGANISM: Plasmodium falciparum

<400> SEQUENCE: 55

Ile Asn Pro Asn Val Asp Pro Asn Ala Asn Pro Asn Ala Asn Pro Asn
 1               5                  10                  15

Ala Asn Pro Asn Val Asp Pro Glu Leu
            20                  25

<210> SEQ ID NO 56
<211> LENGTH: 75
<212> TYPE: DNA
<213> ORGANISM: Plasmodium falciparum

<400> SEQUENCE: 56
aattaatccg aacgtggatc caaatgccaa ccctaacgct aatccaaacg ccaacccgaa    60
tgttgaccct gagct                                                    75

<210> SEQ ID NO 57
<211> LENGTH: 67
<212> TYPE: DNA
<213> ORGANISM: Plasmodium falciparum

<400> SEQUENCE: 57
cagggtcaac attcgggttg gcgtttggat tagcgttagg gttggcattt ggatccacgt    60
tcggatt                                                             67

<210> SEQ ID NO 58
<211> LENGTH: 27
<212> TYPE: PRT
<213> ORGANISM: Plasmodium falciparum

<400> SEQUENCE: 58

Ile Asn Pro Asn Val Asp Pro Asn Ala Asn Pro Asn Ala Asn Pro Asn
 1               5                  10                  15

Ala Asn Pro Asn Val Asp Pro Asn Ala Glu Leu
            20                  25

<210> SEQ ID NO 59
<211> LENGTH: 81
<212> TYPE: DNA
<213> ORGANISM: Plasmodium falciparum

<400> SEQUENCE: 59
aattaatccg aacgtggatc caaatgccaa ccctaacgct aatccaaacg ccaacccgaa    60
tgttgaccct aatgctgagc t                                             81

<210> SEQ ID NO 60
<211> LENGTH: 73
<212> TYPE: DNA

<213> ORGANISM: Plasmodium falciparum

<400> SEQUENCE: 60
cagcattagg gtcaacattc gggttggcgt ttggattagc gttagggttg gcatttggat    60
ccacgttcgg att    73

<210> SEQ ID NO 61
<211> LENGTH: 21
<212> TYPE: PRT
<213> ORGANISM: Plasmodium falciparum

<400> SEQUENCE: 61

Ile Asn Val Asp Pro Asn Ala Asn Pro Asn Ala Asn Pro Asn Ala Asn
1               5                   10                  15

Pro Asn Val Glu Leu
            20

<210> SEQ ID NO 62
<211> LENGTH: 63
<212> TYPE: DNA
<213> ORGANISM: Plasmodium falciparum

<400> SEQUENCE: 62
aattaacgtg gatccaaatg ccaaccctaa cgctaatcca aacgccaacc cgaatgttga    60
gct    63

<210> SEQ ID NO 63
<211> LENGTH: 55
<212> TYPE: DNA
<213> ORGANISM: Plasmodium falciparum

<400> SEQUENCE: 63
caacattcgg gttggcgttt ggattagcgt tagggttggc atttggatcc acgtt    55

<210> SEQ ID NO 64
<211> LENGTH: 23
<212> TYPE: PRT
<213> ORGANISM: Plasmodium falciparum

<400> SEQUENCE: 64

Ile Asn Val Asp Pro Asn Ala Asn Pro Asn Ala Asn Pro Asn Ala Asn
1               5                   10                  15

Pro Asn Val Asp Pro Glu Leu
            20

<210> SEQ ID NO 65
<211> LENGTH: 69
<212> TYPE: DNA
<213> ORGANISM: Plasmodium falciparum

<400> SEQUENCE: 65
aattaacgtg gatccaaatg ccaaccctaa cgctaatcca aacgccaacc cgaatgttga    60
ccctgagct    69

<210> SEQ ID NO 66
<211> LENGTH: 61
<212> TYPE: DNA
<213> ORGANISM: Plasmodium falciparum

<400> SEQUENCE: 66
cagggtcaac attcgggttg gcgtttggat tagcgttagg gttggcattt ggatccacgt    60
t                                                                61

<210> SEQ ID NO 67
<211> LENGTH: 25
<212> TYPE: PRT
<213> ORGANISM: Plasmodium falciparum

<400> SEQUENCE: 67

Ile Asn Val Asp Pro Asn Ala Asn Pro Asn Ala Asn Pro Asn Ala Asn
 1               5                  10                  15

Pro Asn Val Asp Pro Asn Ala Glu Leu
            20                  25

<210> SEQ ID NO 68
<211> LENGTH: 75
<212> TYPE: DNA
<213> ORGANISM: Plasmodium falciparum

<400> SEQUENCE: 68
aattaacgtg gatccaaatg ccaaccctaa cgctaatcca aacgccaacc cgaatgttga     60
ccctaatgct gagct                                                     75

<210> SEQ ID NO 69
<211> LENGTH: 67
<212> TYPE: DNA
<213> ORGANISM: Plasmodium falciparum

<400> SEQUENCE: 69
cagcattagg gtcaacattc gggttggcgt ttggattagc gttagggttg gcatttggat     60
ccacgtt                                                              67

<210> SEQ ID NO 70
<211> LENGTH: 19
<212> TYPE: PRT
<213> ORGANISM: Plasmodium falciparum

<400> SEQUENCE: 70

Ile Asp Pro Asn Ala Asn Pro Asn Ala Asn Pro Asn Ala Asn Pro Asn
 1               5                  10                  15

Val Glu Leu

<210> SEQ ID NO 71
<211> LENGTH: 57
<212> TYPE: DNA
<213> ORGANISM: Plasmodium falciparum

<400> SEQUENCE: 71
aattgatcca aatgccaacc ctaacgctaa tccaaacgcc aacccgaatg ttgagct        57

<210> SEQ ID NO 72
<211> LENGTH: 49
<212> TYPE: DNA
<213> ORGANISM: Plasmodium falciparum

<400> SEQUENCE: 72
caacattcgg gttggcgttt ggattagcgt tagggttggc atttggatc                 49

<210> SEQ ID NO 73
<211> LENGTH: 21
<212> TYPE: PRT
<213> ORGANISM: Plasmodium falciparum

<400> SEQUENCE: 73

Ile Asp Pro Asn Ala Asn Pro Asn Ala Asn Pro Asn Ala Asn Pro Asn
 1               5                  10                  15
Val Asp Pro Glu Leu
            20

<210> SEQ ID NO 74
<211> LENGTH: 63
<212> TYPE: DNA
<213> ORGANISM: Plasmodium falciparum

<400> SEQUENCE: 74
aattgatcca aatgccaacc ctaacgctaa tccaaacgcc aacccgaatg ttgaccctga    60
gct                                                                 63

<210> SEQ ID NO 75
<211> LENGTH: 55
<212> TYPE: DNA
<213> ORGANISM: Plasmodium falciparum

<400> SEQUENCE: 75
cagggtcaac attcgggttg gcgtttggat tagcgttagg gttggcattt ggatc         55

<210> SEQ ID NO 76
<211> LENGTH: 23
<212> TYPE: PRT
<213> ORGANISM: Plasmodium falciparum

<400> SEQUENCE: 76

Ile Asp Pro Asn Ala Asn Pro Asn Ala Asn Pro Asn Ala Asn Pro Asn
 1               5                  10                  15
Val Asp Pro Asn Ala Glu Leu
            20

<210> SEQ ID NO 77
<211> LENGTH: 69
<212> TYPE: DNA
<213> ORGANISM: Plasmodium falciparum

<400> SEQUENCE: 77
aattgatcca aatgccaacc ctaacgctaa tccaaacgcc aacccgaatg ttgaccctaa    60
tgccgagct                                                           69

<210> SEQ ID NO 78
<211> LENGTH: 61
<212> TYPE: DNA
<213> ORGANISM: Plasmodium falciparum

<400> SEQUENCE: 78
cgccattagg gtcaacattc gggttggcgt ttggattagc gttagggttg gcatttggat    60
c                                                                   61

<210> SEQ ID NO 79
<211> LENGTH: 21
<212> TYPE: PRT
<213> ORGANISM: Plasmodium falciparum

<400> SEQUENCE: 79

Ile Glu Tyr Leu Asn Lys Ile Gln Asn Ser Leu Ser Thr Glu Trp Ser
 1               5                  10                  15

Pro Cys Ser Val Thr
            20

<210> SEQ ID NO 80
<211> LENGTH: 69
<212> TYPE: DNA
<213> ORGANISM: Plasmodium falciparum

<400> SEQUENCE: 80
aattgaatat ctgaacaaaa tccagaactc tctgtccacc gaatggtctc cgtgctccgt    60
tacctagta                                                           69

<210> SEQ ID NO 81
<211> LENGTH: 69
<212> TYPE: DNA
<213> ORGANISM: Plasmodium falciparum

<400> SEQUENCE: 81
agcttactag gtaacggagc acggagacca ttcggtggac agagagttct ggattttgtt    60
cagatattc                                                           69

<210> SEQ ID NO 82
<211> LENGTH: 24
<212> TYPE: PRT
<213> ORGANISM: Plasmodium vivax

<400> SEQUENCE: 82

Ile Pro Ala Gly Asp Arg Ala Asp Gly Gln Pro Ala Gly Asp Arg Ala
 1               5                  10                  15

Ala Gly Gln Pro Ala Gly Glu Leu
            20

<210> SEQ ID NO 83
<211> LENGTH: 72
<212> TYPE: DNA
<213> ORGANISM: Plasmodium vivax

<400> SEQUENCE: 83
aattccggct ggtgaccgtg cagatggcca gccagcgggt gaccgcgctg caggccagcc    60
ggctggcgag ct                                                       72

<210> SEQ ID NO 84
<211> LENGTH: 64
<212> TYPE: DNA
<213> ORGANISM: Plasmodium vivax

<400> SEQUENCE: 84
cgccagccgg ctggcctgca gcgcggtcac ccgctggctg gccatctgca cggtcaccag    60
ccgg                                                                64

<210> SEQ ID NO 85
<211> LENGTH: 21
<212> TYPE: PRT
<213> ORGANISM: Plasmodium vivax

<400> SEQUENCE: 85

Ile Asp Arg Ala Ala Gly Gln Pro Ala Gly Asp Arg Ala Asp Gly Gln
 1               5                  10                  15

Pro Ala Gly Glu Leu
            20

```
<210> SEQ ID NO 86
<211> LENGTH: 63
<212> TYPE: DNA
<213> ORGANISM: Plasmodium vivax

<400> SEQUENCE: 86
aattgacaga gcagccggac aaccagcagg cgatcgagca gacggacagc ccgcagggga    60
gct                                                                  63

<210> SEQ ID NO 87
<211> LENGTH: 55
<212> TYPE: DNA
<213> ORGANISM: Plasmodium vivax

<400> SEQUENCE: 87
cccctgcggg ctgtccgtct gctcgatcgc ctgctggttg tccggctgct ctgtc          55

<210> SEQ ID NO 88
<211> LENGTH: 21
<212> TYPE: PRT
<213> ORGANISM: Plasmodium falciparum

<400> SEQUENCE: 88

Ile Ala Asn Gly Ala Gly Asn Gln Pro Gly Ala Asn Gly Ala Gly Asp
 1               5                  10                  15

Gln Pro Gly Glu Leu
            20

<210> SEQ ID NO 89
<211> LENGTH: 63
<212> TYPE: DNA
<213> ORGANISM: Plasmodium vivax

<400> SEQUENCE: 89
aattgcgaac ggcgccggta atcagccggg ggcaaacggc gcgggtgatc aaccagggga    60
gct                                                                  63

<210> SEQ ID NO 90
<211> LENGTH: 55
<212> TYPE: DNA
<213> ORGANISM: Plasmodium vivax

<400> SEQUENCE: 90
cccctggttg atcacccgcg ccgtttgccc ccggctgatt accggcgccg ttcgc          55

<210> SEQ ID NO 91
<211> LENGTH: 21
<212> TYPE: PRT
<213> ORGANISM: Plasmodium vivax

<400> SEQUENCE: 91

Ile Ala Asn Gly Ala Asp Asn Gln Pro Gly Ala Asn Gly Ala Asp Asp
 1               5                  10                  15

Gln Pro Gly Glu Leu
            20

<210> SEQ ID NO 92
<211> LENGTH: 63
<212> TYPE: DNA
<213> ORGANISM: Plasmodium vivax
```

-continued

```
<400> SEQUENCE: 92
aattgcgaac ggcgccgata tcagccgggg tgcaaacggg gcggatgacc aaccaggcga    60
gct                                                                 63

<210> SEQ ID NO 93
<211> LENGTH: 55
<212> TYPE: DNA
<213> ORGANISM: Plasmodium vivax

<400> SEQUENCE: 93
cgcctggttg gtcatccgcc ccgtttgcac ccggctgatt atcggcgccg ttcgc         55

<210> SEQ ID NO 94
<211> LENGTH: 39
<212> TYPE: PRT
<213> ORGANISM: Plasmodium vivax

<400> SEQUENCE: 94
```

Ile Ala Asn Gly Ala Gly Asn Gln Pro Gly Ala Asn Gly Ala Gly Asp
 1               5                  10                  15

Gln Pro Gly Ala Asn Gly Ala Asp Asn Gln Pro Gly Ala Asn Gly Ala
             20                  25                  30

Asp Asp Gln Pro Gly Glu Leu
         35

```
<210> SEQ ID NO 95
<211> LENGTH: 117
<212> TYPE: DNA
<213> ORGANISM: Plasmodium vivax

<400> SEQUENCE: 95
aattgcgaac ggcgccggta atcagccggg agcaaacggc gcgggggatc aaccaggcgc    60
caatggtgca gacaaccagc ctggggcgaa tggagccgat gaccaacccg gcgagct      117

<210> SEQ ID NO 96
<211> LENGTH: 109
<212> TYPE: DNA
<213> ORGANISM: Plasmodium vivax

<400> SEQUENCE: 96
cgccgggttg gtcatcggct ccattcgccc caggctggtt gtctgcacca ttggcgcctg    60
gttgatcccc cgcgccgttt gctcccggct gattaccggc gccgttcgc              109

<210> SEQ ID NO 97
<211> LENGTH: 25
<212> TYPE: PRT
<213> ORGANISM: Plasmodium vivax

<400> SEQUENCE: 97
```

Ile Ala Pro Gly Ala Asn Gln Glu Gly Gly Ala Ala Ala Pro Gly Ala
 1               5                  10                  15

Asn Gln Glu Gly Gly Ala Ala Glu Leu
             20                  25

```
<210> SEQ ID NO 98
<211> LENGTH: 75
<212> TYPE: DNA
<213> ORGANISM: Plasmodium vivax

<400> SEQUENCE: 98
```

-continued

```
aattgcgccg ggcgccaacc aggaaggtgg ggctgcagcg ccaggagcca atcaagaagg    60
cggtgcagcg gagct                                                    75
```

<210> SEQ ID NO 99
<211> LENGTH: 67
<212> TYPE: DNA
<213> ORGANISM: Plasmodium vivax

<400> SEQUENCE: 99

```
ccgctgcacc gccttcttga ttggctcctg gcgctgcagc cccaccttcc tggttggcgc    60
ccggcgc                                                             67
```

<210> SEQ ID NO 100
<211> LENGTH: 21
<212> TYPE: PRT
<213> ORGANISM: Plasmodium vivax

<400> SEQUENCE: 100

```
Ile Glu Tyr Leu Asp Lys Val Arg Ala Thr Val Gly Thr Glu Trp Thr
  1               5                  10                  15

Pro Cys Ser Val Thr
              20
```

<210> SEQ ID NO 101
<211> LENGTH: 69
<212> TYPE: DNA
<213> ORGANISM: Plasmodium vinckei

<400> SEQUENCE: 101

```
aattgaatat ctggataaag tgcgtgcgac cgttggcacg gaatggactc cgtgcagcgt    60
gacctaata                                                           69
```

<210> SEQ ID NO 102
<211> LENGTH: 69
<212> TYPE: DNA
<213> ORGANISM: Plasmodium vivax

<400> SEQUENCE: 102

```
agcttattag gtcacgctcg acggagtcca ttccgtgcca acgtcgcac gcactttatc     60 cagatattc                                                           69
```

<210> SEQ ID NO 103
<211> LENGTH: 10
<212> TYPE: PRT
<213> ORGANISM: Plasmodium falciparum

<400> SEQUENCE: 103

```
Thr Val Ser Ala Pro Ser Trp Glu Thr Ser
  1               5                  10
```

<210> SEQ ID NO 104
<211> LENGTH: 42
<212> TYPE: DNA
<213> ORGANISM: Plasmodium falciparum

<400> SEQUENCE: 104

```
gccaagctta ctaggtaacg gaggccggag accattcggt gg                      42
```

<210> SEQ ID NO 105
<211> LENGTH: 6
<212> TYPE: PRT

```
<213> ORGANISM: Hepatitis B virus

<400> SEQUENCE: 105

Met Asp Ile Asp Pro Tyr
 1               5

<210> SEQ ID NO 106
<211> LENGTH: 8
<212> TYPE: PRT
<213> ORGANISM: Hepatitis B virus

<400> SEQUENCE: 106

Cys Val Val Thr Thr Glu Pro Leu
 1               5

<210> SEQ ID NO 107
<211> LENGTH: 37
<212> TYPE: DNA
<213> ORGANISM: Hepatitis B virus

<400> SEQUENCE: 107
cgcaagctta ctagcaaaca acagtagtct ccggaag                              37

<210> SEQ ID NO 108
<211> LENGTH: 7
<212> TYPE: PRT
<213> ORGANISM: Hepatitis B virus

<400> SEQUENCE: 108

Pro Leu Thr Ser Leu Ile Pro
 1               5

<210> SEQ ID NO 109
<211> LENGTH: 32
<212> TYPE: DNA
<213> ORGANISM: Hepatitis B virus

<400> SEQUENCE: 109
cgcaagctta cggaagtgtt gataggatag gg                                   32

<210> SEQ ID NO 110
<211> LENGTH: 8
<212> TYPE: PRT
<213> ORGANISM: Hepatitis B virus

<400> SEQUENCE: 110

Thr Ser Leu Ile Pro Ala Asn Pro
 1               5

<210> SEQ ID NO 111
<211> LENGTH: 34
<212> TYPE: DNA
<213> ORGANISM: Hepatitis B virus

<400> SEQUENCE: 111
cgcaagctta tgttgatagg atagggcat ttgg                                  34

<210> SEQ ID NO 112
<211> LENGTH: 7
<212> TYPE: PRT
<213> ORGANISM: Hepatica americana

<400> SEQUENCE: 112

Leu Ile Pro Ala Asn Pro Pro
```

```
        1               5

<210> SEQ ID NO 113
<211> LENGTH: 31
<212> TYPE: DNA
<213> ORGANISM: Hepatitis B virus

<400> SEQUENCE: 113
cgcaagctta taggataggg gcatttggtg g                              31

<210> SEQ ID NO 114
<211> LENGTH: 6
<212> TYPE: PRT
<213> ORGANISM: Hepatitis B virus

<400> SEQUENCE: 114

Ile Pro Ala Asn Pro Pro
 1               5

<210> SEQ ID NO 115
<211> LENGTH: 28
<212> TYPE: DNA
<213> ORGANISM: Hepatitis B virus

<400> SEQUENCE: 115
gcgaagctta gatagggca tttggtgg                                   28

<210> SEQ ID NO 116
<211> LENGTH: 6
<212> TYPE: PRT
<213> ORGANISM: Hepatitis B virus

<400> SEQUENCE: 116

Pro Ala Asn Pro Pro Arg
 1               5

<210> SEQ ID NO 117
<211> LENGTH: 28
<212> TYPE: DNA
<213> ORGANISM: Hepatitis B virus

<400> SEQUENCE: 117
cgcaagctta agggcattt ggtggtct                                   28

<210> SEQ ID NO 118
<211> LENGTH: 7
<212> TYPE: PRT
<213> ORGANISM: Hepatitis B virus

<400> SEQUENCE: 118

Cys Pro Ala Asn Pro Pro Arg
 1               5

<210> SEQ ID NO 119
<211> LENGTH: 31
<212> TYPE: DNA
<213> ORGANISM: Hepatitis B virus

<400> SEQUENCE: 119
gcgaagctta gcaaggggca tttggtggtc t                              31

<210> SEQ ID NO 120
<211> LENGTH: 7
<212> TYPE: PRT
```

```
<213> ORGANISM: Hepatitis B virus

<400> SEQUENCE: 120

Ala Asn Pro Pro Arg Tyr Ala
 1               5

<210> SEQ ID NO 121
<211> LENGTH: 30
<212> TYPE: DNA
<213> ORGANISM: Hepatitis B virus

<400> SEQUENCE: 121
gcgaagctta ggcatttggt ggtctatagc                                    30

<210> SEQ ID NO 122
<211> LENGTH: 8
<212> TYPE: PRT
<213> ORGANISM: Hepatitis B virus

<400> SEQUENCE: 122

Cys Ala Asn Pro Pro Arg Tyr Ala
 1               5

<210> SEQ ID NO 123
<211> LENGTH: 32
<212> TYPE: DNA
<213> ORGANISM: Hepatitis B virus

<400> SEQUENCE: 123
gcgaagctta gcaggcattt ggtggtctat aa                                 32

<210> SEQ ID NO 124
<211> LENGTH: 7
<212> TYPE: PRT
<213> ORGANISM: Hepatitis B virus

<400> SEQUENCE: 124

Asn Pro Pro Arg Tyr Ala Pro
     1               5

<210> SEQ ID NO 125
<211> LENGTH: 31
<212> TYPE: DNA
<213> ORGANISM: Hepatitis B virus

<400> SEQUENCE: 125
cgcaagctta atttggtggt ctataagctg g                                  31

<210> SEQ ID NO 126
<211> LENGTH: 8
<212> TYPE: PRT
<213> ORGANISM: Plasmodium falciparum

<400> SEQUENCE: 126

Asn Ala Asn Pro Asn Val Asp Pro
 1               5

<210> SEQ ID NO 127
<211> LENGTH: 6
<212> TYPE: PRT
<213> ORGANISM: Homo sapiens

<400> SEQUENCE: 127

Asn Tyr Lys Lys Pro Lys
```

-continued

```
            1               5

<210> SEQ ID NO 128
<211> LENGTH: 7
<212> TYPE: PRT
<213> ORGANISM: Homo sapiens

<400> SEQUENCE: 128

Lys Arg Gly Pro Arg Thr His
 1               5

<210> SEQ ID NO 129
<211> LENGTH: 21
<212> TYPE: PRT
<213> ORGANISM: Homo sapiens

<400> SEQUENCE: 129

Leu His Pro Asp Glu Thr Lys Asn Met Leu Glu Met Ile Phe Thr Pro
 1               5                   10                  15

Arg Asn Ser Asp Arg
            20

<210> SEQ ID NO 130
<211> LENGTH: 5
<212> TYPE: PRT
<213> ORGANISM: Human immunodeficiency virus type 1

<400> SEQUENCE: 130

Arg Ile Lys Gln Ile
 1               5

<210> SEQ ID NO 131
<211> LENGTH: 11
<212> TYPE: PRT
<213> ORGANISM: Human immunodeficiency virus type 1

<400> SEQUENCE: 131

Arg Ile Lys Gln Ile Gly Met Pro Gly Gly Lys
 1               5                   10

<210> SEQ ID NO 132
<211> LENGTH: 10
<212> TYPE: PRT
<213> ORGANISM: Human immunodeficiency virus type 1

<400> SEQUENCE: 132

Leu Leu Glu Leu Asp Lys Trp Ala Ser Leu
 1               5                   10

<210> SEQ ID NO 133
<211> LENGTH: 14
<212> TYPE: PRT
<213> ORGANISM: Human immunodeficiency virus type 1

<400> SEQUENCE: 133

Glu Gln Glu Leu Leu Glu Leu Asp Lys Trp Ala Ser Leu Trp
 1               5                   10

<210> SEQ ID NO 134
<211> LENGTH: 33
<212> TYPE: PRT
<213> ORGANISM: Human immunodeficiency virus type 1

<400> SEQUENCE: 134
```

```
Val Gln Gln Gln Asn Asn Leu Leu Arg Ala Ile Glu Ala Gln Gln His
 1               5                  10                  15

Leu Leu Gln Leu Thr Val Trp Gly Ile Lys Gln Leu Gln Ala Arg Ile
             20                  25                  30

Leu
```

<210> SEQ ID NO 135
<211> LENGTH: 16
<212> TYPE: PRT
<213> ORGANISM: Human immunodeficiency virus type 1

<400> SEQUENCE: 135

```
His Leu Leu Gln Leu Thr Val Trp Gly Ile Lys Gln Leu Gln Ala Arg
 1               5                  10                  15
```

<210> SEQ ID NO 136
<211> LENGTH: 36
<212> TYPE: PRT
<213> ORGANISM: Human immunodeficiency virus

<400> SEQUENCE: 136

```
Tyr Thr His Ile Ile Tyr Ser Leu Ile Glu Gln Ser Gln Asn Gln Gln
 1               5                  10                  15

Glu Lys Asn Glu Gln Glu Leu Leu Ala Leu Asp Lys Trp Ala Ser Leu
             20                  25                  30

Trp Asn Trp Phe
             35
```

<210> SEQ ID NO 137
<211> LENGTH: 26
<212> TYPE: PRT
<213> ORGANISM: Human immunodeficiency virus type 1

<400> SEQUENCE: 137

```
Tyr Thr His Ile Ile Tyr Ser Leu Ile Glu Gln Ser Gln Asn Gln Gln
 1               5                  10                  15

Glu Lys Asn Glu Gln Glu Leu Leu Glu Leu
             20                  25
```

<210> SEQ ID NO 138
<211> LENGTH: 19
<212> TYPE: PRT
<213> ORGANISM: Homo sapiens

<400> SEQUENCE: 138

```
Gly Arg Glu Arg Pro Arg Leu Ser Asp Arg Pro Gln Leu Pro Tyr
 1               5                  10                  15

Leu Glu Ala
```

<210> SEQ ID NO 139
<211> LENGTH: 20
<212> TYPE: PRT
<213> ORGANISM: Homo sapiens

<400> SEQUENCE: 139

```
Arg Glu Gln Arg Arg Phe Ser Val Ser Thr Leu Arg Asn Leu Gly Leu
 1               5                  10                  15

Gly Lys Lys Ser
             20
```

<210> SEQ ID NO 140
<211> LENGTH: 18

```
<212> TYPE: PRT
<213> ORGANISM: Plasmodium yoelii

<400> SEQUENCE: 140

Pro Asn Lys Leu Pro Arg Ser Thr Ala Val Val His Gln Leu Lys Arg
 1               5                  10                  15

Lys His

<210> SEQ ID NO 141
<211> LENGTH: 11
<212> TYPE: PRT
<213> ORGANISM: Plasmodium yoelii

<400> SEQUENCE: 141

Thr Ala Val Val His Gln Leu Lys Arg Lys His
 1               5                  10

<210> SEQ ID NO 142
<211> LENGTH: 22
<212> TYPE: PRT
<213> ORGANISM: Plasmodium vivax

<400> SEQUENCE: 142

Pro Ala Gly Asp Arg Ala Asp Gly Gln Pro Ala Gly Asp Arg Ala Ala
 1               5                  10                  15

Ala Gly Gln Pro Ala Gly
                20

<210> SEQ ID NO 143
<211> LENGTH: 12
<212> TYPE: PRT
<213> ORGANISM: Avian leukosis virus

<400> SEQUENCE: 143

Asn Gln Ser Trp Thr Met Val Ser Pro Ile Asn Val
 1               5                  10

<210> SEQ ID NO 144
<211> LENGTH: 16
<212> TYPE: PRT
<213> ORGANISM: Avian leukosis virus

<400> SEQUENCE: 144

Met Ile Lys Asn Gly Thr Lys Arg Thr Ala Val Thr Phe Gly Ser Val
 1               5                  10                  15

<210> SEQ ID NO 145
<211> LENGTH: 19
<212> TYPE: PRT
<213> ORGANISM: Foot-and-mouth disease virus

<400> SEQUENCE: 145

Pro Asn Leu Arg Gly Asp Leu Gln Val Leu Ala Gln Lys Val Ala Arg
 1               5                  10                  15

Thr Leu Pro

<210> SEQ ID NO 146
<211> LENGTH: 26
<212> TYPE: PRT
<213> ORGANISM: Foot-and-mouth disease virus

<400> SEQUENCE: 146

Arg Tyr Asn Arg Asn Ala Val Pro Asn Leu Arg Gly Asp Leu Gln Val
```

```
                    1               5                  10                  15
Leu Ala Gln Lys Val Ala Arg Thr Leu Pro
                    20                  25
```

<210> SEQ ID NO 147
<211> LENGTH: 34
<212> TYPE: PRT
<213> ORGANISM: Hepatitis B virus

<400> SEQUENCE: 147

```
Arg Arg Arg Gly Arg Ser Pro Arg Arg Thr Pro Ser Pro Arg Arg
 1               5                  10                  15

Arg Arg Ser Gln Ser Pro Arg Arg Arg Ser Gln Ser Arg Glu Ser
                20                  25                  30

Gln Cys
```

<210> SEQ ID NO 148
<211> LENGTH: 20
<212> TYPE: PRT
<213> ORGANISM: Plasmodium falciparum

<400> SEQUENCE: 148

```
Glu Tyr Leu Asn Lys Ile Gln Asn Ser Leu Ser Thr Glu Trp Ser Pro
 1               5                  10                  15

Cys Ser Val Thr
                20
```

<210> SEQ ID NO 149
<211> LENGTH: 20
<212> TYPE: PRT
<213> ORGANISM: Plasmodium falciparum

<400> SEQUENCE: 149

```
Glu Tyr Leu Asn Lys Ile Gln Asn Ser Leu Ser Thr Glu Trp Ser Pro
 1               5                  10                  15

Ala Ser Val Thr
                20
```

<210> SEQ ID NO 150
<211> LENGTH: 18
<212> TYPE: PRT
<213> ORGANISM: Plasmodium vivax

<400> SEQUENCE: 150

```
Asp Arg Ala Ala Gly Gln Pro Ala Gly Asp Arg Ala Asp Gly Gln Pro
 1               5                  10                  15

Ala Gly
```

<210> SEQ ID NO 151
<211> LENGTH: 36
<212> TYPE: PRT
<213> ORGANISM: Plasmodium vivax

<400> SEQUENCE: 151

```
Ala Asn Gly Ala Gly Asn Gln Pro Gly Ala Asn Gly Ala Gly Asp Gln
 1               5                  10                  15

Pro Gly Ala Asn Gly Ala Asp Asn Gln Pro Gly Ala Asn Gly Ala Asp
                20                  25                  30

Asp Gln Pro Gly
                35
```

-continued

<210> SEQ ID NO 152
<211> LENGTH: 9
<212> TYPE: PRT
<213> ORGANISM: Plasmodium vivax

<400> SEQUENCE: 152

Asp Arg Ala Ala Gly Gln Pro Ala Gly
1 5

<210> SEQ ID NO 153
<211> LENGTH: 9
<212> TYPE: PRT
<213> ORGANISM: Plasmodium vivax

<400> SEQUENCE: 153

Asp Arg Ala Asp Gly Gln Pro Ala Gly
1 5

<210> SEQ ID NO 154
<211> LENGTH: 9
<212> TYPE: PRT
<213> ORGANISM: Plasmodium vivax

<400> SEQUENCE: 154

Ala Asn Gly Ala Gly Asn Gln Pro Gly
1 5

<210> SEQ ID NO 155
<211> LENGTH: 9
<212> TYPE: PRT
<213> ORGANISM: Plasmodium vivax

<400> SEQUENCE: 155

Ala Asn Gly Ala Gly Asp Gln Pro Gly
1 5

<210> SEQ ID NO 156
<211> LENGTH: 9
<212> TYPE: PRT
<213> ORGANISM: Plasmodium vivax

<400> SEQUENCE: 156

Ala Asn Gly Ala Asp Asn Gln Pro Gly
1 5

<210> SEQ ID NO 157
<211> LENGTH: 9
<212> TYPE: PRT
<213> ORGANISM: Plasmodium vivax

<400> SEQUENCE: 157

Ala Asn Gly Ala Asp Asp Gln Pro Gly
1 5

<210> SEQ ID NO 158
<211> LENGTH: 11
<212> TYPE: PRT
<213> ORGANISM: Plasmodium vivax

<400> SEQUENCE: 158

Ala Pro Gly Ala Asn Gln Glu Gly Gly Ala Ala
1 5 10

<210> SEQ ID NO 159

```
<211> LENGTH: 21
<212> TYPE: PRT
<213> ORGANISM: Plasmodium vivax

<400> SEQUENCE: 159

Pro Ala Gly Asp Arg Ala Asp Gly Gln Pro Ala Gly Asp Arg Ala Ala
 1               5                  10                  15
Gly Gln Pro Ala Gly
            20

<210> SEQ ID NO 160
<211> LENGTH: 18
<212> TYPE: PRT
<213> ORGANISM: Plasmodium vivax

<400> SEQUENCE: 160

Ala Asn Gly Ala Gly Asn Gln Pro Gly Ala Asn Gly Ala Gly Asp Gln
 1               5                  10                  15
Pro Gly

<210> SEQ ID NO 161
<211> LENGTH: 19
<212> TYPE: PRT
<213> ORGANISM: Plasmodium vivax

<400> SEQUENCE: 161

Gln Ala Asn Gly Ala Asp Asn Gln Pro Gly Ala Asn Gly Ala Asp Asp
 1               5                  10                  15
Gln Pro Gly

<210> SEQ ID NO 162
<211> LENGTH: 44
<212> TYPE: DNA
<213> ORGANISM: Plasmodium vivax

<400> SEQUENCE: 162
cgcgaattca agcgaacggc gccgataatc agccggcggg tgca                    44

<210> SEQ ID NO 163
<211> LENGTH: 22
<212> TYPE: PRT
<213> ORGANISM: Plasmodium vivax

<400> SEQUENCE: 163

Ala Pro Gly Ala Asn Gln Glu Gly Gly Ala Ala Ala Pro Gly Ala Asn
 1               5                  10                  15
Gln Glu Gly Gly Ala Ala
            20

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: modified
      portion of Hepatitis B core

<400> SEQUENCE: 164

Cys Val Val Thr Thr Glu Pro
 1               5

<210> SEQ ID NO 165
<211> LENGTH: 42
```

-continued

<212> TYPE: DNA
<213> ORGANISM: Artificial Sequence
<220> FEATURE:
<223> OTHER INFORMATION: Description of Artificial Sequence: modified
      portion of Hepatitis B core

<400> SEQUENCE: 165
gcaagcttac tattgaattc cgcaaacaac agtagtctcc gg                    42

<210> SEQ ID NO 166
<211> LENGTH: 26
<212> TYPE: PRT
<213> ORGANISM: Artificial Sequence
<220> FEATURE:
<223> OTHER INFORMATION: Description of Artificial Sequence: modified
      portion of Hepatitis B core

<400> SEQUENCE: 166

Thr Thr Val Val Gly Ile Glu Tyr Leu Asn Lys Ile Gln Asn Ser Leu
 1               5                  10                  15

Ser Thr Glu Trp Ser Pro Cys Ser Val Thr
            20                  25

<210> SEQ ID NO 167
<211> LENGTH: 27
<212> TYPE: PRT
<213> ORGANISM: Artificial Sequence
<220> FEATURE:
<223> OTHER INFORMATION: Description of Artificial Sequence: modified
      portion of Hepatitis B core

<400> SEQUENCE: 167

Thr Thr Val Val Cys Gly Ile Glu Tyr Leu Asn Lys Ile Gln Asn Ser
 1               5                  10                  15

Leu Ser Thr Glu Trp Ser Pro Ala Ser Val Thr
            20                  25

<210> SEQ ID NO 168
<211> LENGTH: 217
<212> TYPE: PRT
<213> ORGANISM: Spermophilus variegatus

<400> SEQUENCE: 168

Met Tyr Leu Phe His Leu Cys Leu Val Phe Ala Cys Val Pro Cys Pro
 1               5                  10                  15

Thr Val Gln Ala Ser Lys Leu Cys Leu Gly Trp Leu Trp Asp Met Asp
            20                  25                  30

Ile Asp Pro Tyr Lys Glu Phe Gly Ser Ser Tyr Gln Leu Leu Asn Phe
        35                  40                  45

Leu Pro Leu Asp Phe Phe Pro Asp Leu Asn Ala Leu Val Asp Thr Ala
    50                  55                  60

Ala Ala Leu Tyr Glu Glu Glu Leu Thr Gly Arg Glu His Cys Ser Pro
65                  70                  75                  80

His His Thr Ala Ile Arg Gln Ala Leu Val Cys Trp Glu Glu Leu Thr
                85                  90                  95

Arg Leu Ile Thr Trp Met Ser Glu Asn Thr Thr Glu Glu Val Arg Arg
            100                 105                 110

Ile Ile Val Asp His Val Asn Asn Thr Trp Gly Leu Lys Val Arg Gln
        115                 120                 125

Thr Leu Trp Phe His Leu Ser Cys Leu Thr Phe Gly Gly His Thr Val
    130                 135                 140

```
Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                165                 170                 175

Val Ile Arg Arg Arg Gly Gly Ser Arg Ala Ala Arg Ser Pro Arg Arg
            180                 185                 190

Arg Thr Pro Ser Pro Arg Arg Arg Ser Gln Ser Pro Arg Arg Arg
        195                 200                 205

Arg Ser Gln Ser Pro Ala Ser Asn Cys
    210                 215

<210> SEQ ID NO 169
<211> LENGTH: 651
<212> TYPE: DNA
<213> ORGANISM: Spermophilus variegatus

<400> SEQUENCE: 169
atgtatcttt tcacctgtg ccttgttttt gcctgtgttc catgtcctac tgttcaagcc      60
tccaagctgt gccttggatg ctttgggac atggacatag atccctataa agaatttggt    120
tcttcttatc agttgttgaa ttttcttcct ttggactttt ttcctgatct caatgcattg    180
gtggacactg ctgctgctct ttatgaagaa gaattaacag gtagggagca ttgttctcct    240
catcatactg ctattagaca ggccttagtg tgttgggaag aattaactag attaattaca    300
tggatgagtg aaaatacaac agaagaagtt agaagaatta ttgttgatca tgtcaataat    360
acttggggac ttaaagtaag acagacttta tggtttcatt tatcatgtct acttttgga    420 caacacacag ttcaagaatt tttggttagt tttggagtat ggattagaac tccagctcct    480
tatagaccac ctaatgcacc cattttatca actcttccgg aacatacagt cattaggaga    540
agaggaggtt caagagctgc taggtccccc cgaagacgca ctccctctcc tcgcaggaga    600
aggtctcaat caccgcgtcg cagacgctct caatctccag cttccaactg c             651

<210> SEQ ID NO 170
<211> LENGTH: 183
<212> TYPE: PRT
<213> ORGANISM: Hepatitis B virus

<400> SEQUENCE: 170

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140
```

```
Glu Thr Thr Val Val Arg Arg Gly Arg Ser Pro Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 171
<211> LENGTH: 185
<212> TYPE: PRT
<213> ORGANISM: Hepatitis B virus

<400> SEQUENCE: 171

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Asn Asn Leu Gln Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Asp Arg Gly Arg Ser Pro Arg Arg Arg
145                 150                 155                 160

Arg Thr Pro Ser Pro Arg Arg Arg Ser Gln Ser Pro Arg Arg Arg Arg
                165                 170                 175

Arg Ser Gln Ser Arg Glu Ser Gln Cys
            180                 185

<210> SEQ ID NO 172
<211> LENGTH: 185
<212> TYPE: PRT
<213> ORGANISM: Hepatitis B virus

<400> SEQUENCE: 172

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Val Gly Leu Lys
                 85                  90                  95
```

-continued

```
Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Pro Ser Gln Ser Pro Arg Arg Arg
                165                 170                 175

Arg Ser Gln Ser Arg Glu Ser Gln Cys
            180                 185

<210> SEQ ID NO 173
<211> LENGTH: 183
<212> TYPE: PRT
<213> ORGANISM: Hepatitis B virus

<400> SEQUENCE: 173

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Arg Ser
                165                 170                 175

Gln Ser Arg Glu Ser Gln Cys
            180

<210> SEQ ID NO 174
<211> LENGTH: 183
<212> TYPE: PRT
<213> ORGANISM: Marmota monax

<400> SEQUENCE: 174

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45
```

```
Ser Pro His His Thr Ala Ile Arg Gln Ala Leu Val Cys Trp Asp Glu
 50                  55                  60

Leu Thr Lys Leu Ile Ala Trp Met Ser Ser Asn Ile Thr Ser Glu Gln
 65                  70                  75                  80

Val Arg Thr Ile Ile Val Asn His Val Asn Asp Thr Trp Gly Leu Lys
                 85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Cys
            180
```

<210> SEQ ID NO 175
<211> LENGTH: 549
<212> TYPE: DNA
<213> ORGANISM: Hepatitis B virus

<400> SEQUENCE: 175

```
atggacatcg acccttataa agaatttgga gctactgtgg agttactctc gtttttgcct      60
tctgacttct ttccttcagt acgagatctt ctagataccg cctcagctct gtatcgggaa    120
gccttagagt ctcctgagca ttgttcacct caccatactg cactcaggca agcaattctt    180
tgctgggggg aactaatgac tctagctacc tgggtgggtg ttaatttgga agatccagcg    240
tctagagacc tagtagtcag ttatgtcaac actaatatgg cctaaagtt caggcaactc     300
tgtggtttc acatttcttg tctcactttt ggaagagaaa cagttataga gtatttggtg     360
tctttcggag tgtggattcg cactcctcca gcttatagac caccaaatgc ccctatccta    420
tcaacacttc cggagactac tgttgttaga cgacgaggca ggtcccctag aagaagaact    480
ccctcgcctc gcagacgaag gtctcaatcg ccgcgtcgca agatctcca atctcgggaa     540
tctcaatgt                                                           549
```

<210> SEQ ID NO 176
<211> LENGTH: 555
<212> TYPE: DNA
<213> ORGANISM: Hepatitis B virus

<400> SEQUENCE: 176

```
atggacattg acccttataa agaatttgga gctactgtgg agttactctc gtttttgcct      60
tctgacttct ttccttccgt acgagatctc ctagacaccg cctcagctct gtatcgagaa    120
gccttagagt ctcctgagca ttgctcacct caccatactg cactcaggca agccattctc    180
tgctgggggg aattgatgac tctagctacc tgggtgggta ataatttgca agatccagca    240
tccagagatc tagtagtcaa ttatgttaat actaacatgg gtttaaagat caggcaacta    300
ttgtggtttc atatatcttg ccttactttt ggaagagaga ctgtacttga atatttggtc    360
tctttcggag tgtggattcg cactcctcca gcttatagac caccaaatgc ccctatctta    420
tcaacacttc cggaaactac tgttgttaga cgacgggacc gaggcaggtc ccctagaaga    480
```

-continued

```
agaactccct cgcctcgcag acgcagatct caatcgccgc gtcgcagaag atctcaatct    540
cgggaatctc aatgt                                                     555
```

<210> SEQ ID NO 177
<211> LENGTH: 555
<212> TYPE: DNA
<213> ORGANISM: Hepatitis B virus

<400> SEQUENCE: 177

```
atggacattg acccttataa agaatttgga gctactgtgg agttactctc gttttttgcct    60 tctgacttct ttccttccgt cagagatctc ctagacaccg cctcagctct gtatcgagaa   120
gccttagagt ctcctgagca ttgctcacct caccatactg cactcaggca agccattctc   180
tgctgggggg aattgatgac tctagctacc tgggtgggta ataatttgga agatccagca   240
tctagggatc ttgtagtaaa ttatgttaat actaacgtgg gtttaaagat caggcaacta   300
ttgtggtttc atatatcttg ccttactttt ggaagagaga ctgtacttga atatttggtc   360
tctttcggag tgtggattcg cactcctcca gcctatagac accaaatgc ccctatctta   420 tcaacacttc cggaaactac tgttgttaga cgacgggacc gaggcaggtc ccctagaaga   480
agaactccct cgcctcgcag acgcagatct ccatcgccgc gtcgcagaag atctcaatct   540
cgggaatctc aatgt                                                     555
```

<210> SEQ ID NO 178
<211> LENGTH: 549
<212> TYPE: DNA
<213> ORGANISM: Hepatitis B virus

<400> SEQUENCE: 178

```
atggacattg acccttataa agaatttgga gctactgtgg agttactctc gttttttgcct    60 tctgacttct ttccttccgt acgagatctt ctagataccg ccgcagctct gtatcgggat   120
gccttagagt ctcctgagca ttgttcacct caccatactg cactcaggca agcaattctt   180
tgctggggag acttaatgac tctagctacc tgggtgggta ctaatttaga agatccagca   240
tctagggacc tagtagtcag ttatgtcaac actaatgtgg gcctaaagtt cagacaatta   300
ttgtggtttc acatttcttg tctcactttt ggaagagaaa cggttctaga gtatttggtg   360
tcttttggag tgtggattcg cactcctcca gcttatagac accaaatgc ccctatccta   420 tcaacgcttc cggagactac tgttgttaga cgacgaggg gtcccctag aagaagaact   480 ccctcgcctc gcagacgaag atctcaatcg ccgcgtcgca gaagatctca atctcgggaa   540
tctcaatgt                                                            549
```

<210> SEQ ID NO 179
<211> LENGTH: 549
<212> TYPE: DNA
<213> ORGANISM: Marmota monax

<400> SEQUENCE: 179

```
atggacattg acccttataa agaatttgga gctactgtgg agttactctc gttttttgcct    60 tctgacttct ttccttccgt acgagatctt ctagataccg ccgcagctct gtatcgggat   120
gccttagagt ctcctgagca ttgttcacct caccatactg cactcaggca agcaattctt   180
tgctggggag acttaatgac tctagctacc tgggtgggta ctaatttaga agatccagca   240
tctagggacc tagtagtcag ttatgtcaac actaatgtgg gcctaaagtt cagacaatta   300
```

```
ttgtggtttc acatttcttg tctcactttt ggaagagaaa cggttctaga gtatttggtg      360
tcttttggag tgtggattcg cactcctcca gcttatagac caccaaatgc ccctatccta      420
tcaacgcttc cggagactac tgttgttaga cgacgaggca ggtcccctag aagaagaact      480
ccctcgcctc gcagacgaag atctcaatcg ccgcgtcgca aagatctca atctcgggaa      540 tctcaatgt                                                              549
```

<210> SEQ ID NO 180
<211> LENGTH: 51
<212> TYPE: DNA
<213> ORGANISM: plasmid pKK223

<400> SEQUENCE: 180

```
ttcacacagg aaacagaatt cccggggatc cgtcgacctg cagccaagct t              51
```

<210> SEQ ID NO 181
<211> LENGTH: 38
<212> TYPE: DNA
<213> ORGANISM: plasmid pKK223

<400> SEQUENCE: 181

```
ttcacataag gaggaaaaaa ccatgggatc cgaagctt                              38
```

<210> SEQ ID NO 182
<211> LENGTH: 16
<212> TYPE: PRT
<213> ORGANISM: Hepatitis B virus

<400> SEQUENCE: 182

```
Gly Ile Val Asn Leu Glu Asp Pro Ala Ser Arg Asp Leu Val Val Ser
  1               5                  10                  15
```

<210> SEQ ID NO 183
<211> LENGTH: 17
<212> TYPE: PRT
<213> ORGANISM: Hepatitis B virus

<400> SEQUENCE: 183

```
Gly Ile Val Asn Leu Glu Asp Pro Ala Ser Arg Asp Leu Val Val Ser
  1               5                  10                  15

Cys
```

<210> SEQ ID NO 184
<211> LENGTH: 4
<212> TYPE: PRT
<213> ORGANISM: Plasmodium falciparum

<400> SEQUENCE: 184

```
Asn Ala Asn Pro
  1
```

<210> SEQ ID NO 185
<211> LENGTH: 4
<212> TYPE: PRT
<213> ORGANISM: Plasmodium falciparum

<400> SEQUENCE: 185

```
Asn Val Asp Pro
  1
```

<210> SEQ ID NO 186
<211> LENGTH: 31

-continued

<212> TYPE: DNA
<213> ORGANISM: Hepatitis B virus

<400> SEQUENCE: 186
gcggaattcc atcttccaaa ttaacaccca c                     31